US007910348B2

(12) United States Patent
Wilting et al.

(10) Patent No.: US 7,910,348 B2
(45) Date of Patent: Mar. 22, 2011

(54) **POLYPEPTIDES OF *ALICYCLOBACILLUS* SP. HAVING GLUTAMIC PEPTIDASE ACTIVITY**

(75) Inventors: Reinhard Wilting, Farum (DK); Soren Flensted Lassen, Farum (DK); Peter Rahbek Ostergaard, Virum (DK)

(73) Assignee: Novozymes A/S, Bagsvaerd (DK)

( * ) Notice: Subject to any disclaimer, the term of this patent is extended or adjusted under 35 U.S.C. 154(b) by 78 days.

(21) Appl. No.: 12/185,413

(22) Filed: Aug. 4, 2008

(65) Prior Publication Data
US 2009/0092707 A1   Apr. 9, 2009

Related U.S. Application Data

(63) Continuation of application No. 11/636,950, filed on Dec. 11, 2006, now abandoned, which is a continuation-in-part of application No. 10/784,592, filed on Feb. 23, 2004, now abandoned.

(30) Foreign Application Priority Data

Jan. 6, 2004  (DK) .................................. 2004 00010
Feb. 4, 2004  (DK) .................................. 2004 00165

(51) Int. Cl.
C12N 9/48 (2006.01)
C07K 14/00 (2006.01)
A23L 1/305 (2006.01)
C11D 1/00 (2006.01)
C12Q 1/37 (2006.01)
C12P 21/00 (2006.01)

(52) U.S. Cl. ......... 435/212; 435/24; 435/69.1; 530/350; 426/63; 510/535

(58) Field of Classification Search .............. 435/24, 435/320.1, 69.1, 325, 252.3, 212, 220; 536/23.2; 530/350
See application file for complete search history.

(56) References Cited

FOREIGN PATENT DOCUMENTS

| WO | WO 01/77315 | 10/2001 |
|---|---|---|
| WO | WO 02/12463 | 2/2002 |
| WO | WO 2005/066339 | 7/2005 |

OTHER PUBLICATIONS

Inoue et al., J. Biol. Chem. 266:19484-19489, 1991.*
Witkowski et al., Biochemistry 38:11643-11650, 1999.*
Seffernick et al., J. Bacteriol. 183(8):2405-2410, 2001.*
Matzke et al., Fems Microbiology Letters, vol. 183, pp. 55-61 (2000).
Koivula et al., Journal of General Microbiology, vol. 139, pp. 2399-2407 (1993).
Bartolucci et al., Biochem J. vol. 328, pp. 277-285 (1997).
Tsuruoka et al., Applied and Environmental Microbiology, vol. 69, No. 1, pp. 162-169 (2003).
Eckert et al., Eur. J. Biochem, vol. 270, pp. 3593-3602 (2003).
Van Dijl et al., ASM Press, pp. 337-355 (2002).
Fleischmann et al, Science, vol. 269, Part 5223, pp. 496-512 (1995).
Jara et al., Mol Gen Genet, vol. 250, pp. 97-105 (1996).
Poussereau et al., Microbiology, vol. 147, pp. 717-726 (2001).
Fujinaga et al., PNAS, vol. 101, No. 10, pp. 3364-3369 (2004).
Sims et al., FEMS Microbiology Letters, vol. 239, pp. 95-101 (2004).
Summary for Family G1, (2005).
Summary For G01.001, (2005).
Branden et al, Introduction to Protein Structure, p. 247 (1991).
Partial translation of Journal Antibacterial Antifungal Agents, vol. 28, No. (8), pp. 499-508 (2000).
Goto et al., Extremophiles, vol. 6, pp. 333-340 (2002).
Huang et al., Journal Biological Chemistry vol. 275, No. (34), pp. 26607-26614 (2000).
Pettipher et al., Food Australia, vol. 52, No. (7), pp. 293-295 (2000).
Takahashi, 1995, Methods Enzyme, vol. 248, pp. 146-155 (1995).
Yoshimune et al., Journal Japan Soy Sauce Res. Inst, 29 (6), 235-239 (2003) Part trans.

* cited by examiner

*Primary Examiner* — Delia M Ramirez
(74) *Attorney, Agent, or Firm* — Kristin J. McNamara

(57) ABSTRACT

Disclosed are isolated polypeptides of *Alicyclobacillus* sp. having glutamic peptidase activity.

15 Claims, No Drawings

SEQUENCE LISTING

```
<160> NUMBER OF SEQ ID NOS: 55

<210> SEQ ID NO 1
<211> LENGTH: 2877
<212> TYPE: DNA
<213> ORGANISM: Alicyclobacillus sp.
<220> FEATURE:
<221> NAME/KEY: misc_feature
<222> LOCATION: (1)..(2877)
<223> OTHER INFORMATION: CDS
<220> FEATURE:
<221> NAME/KEY: misc_feature
<222> LOCATION: (1)..(72)
<223> OTHER INFORMATION: sig_peptide
<220> FEATURE:
<221> NAME/KEY: misc_feature
<222> LOCATION: (73)..(2877)
<223> OTHER INFORMATION: mat_peptide

<400> SEQUENCE: 1
ttgaagactc gatggtcagg tgcgctggct gtgctcatcg ccctcggaac gggtgcctcg      60
cccgcttggg ccagtgtcca cagcgcggcc acgcacgcaa aggcgcacgt cggcgtgcgc     120
gctgcggata tggccgcagc gtccatgtcg gccgagattc agattctgca cgacgcgctc     180
acggcttccg agctgtcgtc cgtccaggcc gcggcacagg ccgccgccaa cctgcctgcc     240
tccacgtggg tgagctggct gtatccgagc gcctcctcgc cgagcgccgc acagacgcag     300
acggcgcagg ccctgggcgc gctcctcacc ttggtcacgt atggcgccgt cgcagacgat     360
ggccaaaaca tcgcacagaa tttgcaaacc cttcagtcga cttcgccgct cttatcgccc     420
gcggccgtct cgatgttcta tcaaaacttc ttcgtgctcg tcgccaatc gtccaaatcc     480 gtgctttcgg gccaggcaac cacctccacc gccggccacg ccctcgccca agcggccgcg     540
ctgacgccac agctcgccgc gtacctgcgc caatccggtc tttcgccgga cgatctcgcc     600
cgcgcctacg tgagctttgc ctccgccgtg gattcgcagg gcgcggcgca aacggctctc     660
```

-continued

```
ctgacgcgca tctgcaccaa catcctgggc tttggcgcgc cgacctccac ggcgaccatc    720
accgtcaacg ccgcggcgaa ccttggacag gtgccgacca ccgcgtttgg cctgaacgcg    780
gccgtgtggg acagcggtct caactcccag accgtcatct ccgaggtgca agcgctccac    840
cccgccctca tccgctggcc cggaggctcc atctcggacg tgtacaattg ggagaccaac    900
acgcggaacg acggcggcta cgtgaatccc gacgacacgt ttgatcactt catgcagttt    960
gtgaatgccg tcggctccac gcctatcatc acggtcaact acggcaccgg cacgccacag   1020
ctcgccgccg actgggtgaa gtacgccgac gtgacccacc acgacaacgt catgtattgg   1080
gaaattggca acgagattta cggcaacggt tactacaacg caacgggtg ggaggcggac    1140 gatcacgccg tggccggcca gccgcaaaaa ggcaaccctg gtttaagccc gcaggcgtac   1200
gcgcaaaacg ccctgcagtt catcaaggcg atgcgcgccg aggacccgtc catcaagatt   1260
ggggccgtgc tcacgatgcc gtacaactgg ccgtggggcg cgaccgtgaa cggcaacgac   1320
gactggaata ccgtcgtcct gaaggcgctc gggccctaca tcgattttgt ggacgtgcac   1380
tggtaccccg agacgcccgg gcaggagacc gacgccggcc tgctcgccga cacagatcaa   1440
atccccgcca tggtggcgga gctcaagcgc gaagtgaaca cctacgccgg atcgaacgcg   1500
aagaacatcc aaatctttgt gaccgagacc aacagcgtat cgtacaaccc cggcgagcag   1560
tcgaccaacc tgcctgaagc gctcttcttg gcggacgatc tcaccgggtt catccaggcc   1620
ggcgcggcca acgtcgactg gtgggatctg ttcaacggcg ccgaggacaa ctacacaagc   1680
ccgagcctct acggcagaa cctgtttggc gattatggac tcttgtcctc cggccagacc   1740
acgcaaaacg gttggcagga ccgcccgcc aacacgccgc ttccgcccta caatggcttc   1800
cagctggtct cggatttcgc gcagcccggc gacacgatgc tcggctccac cacgtcgcag   1860
agcgccatcg acgtgcacgc cgtgcgcaag ccgaatggcg acatttcgct catgctcgtc   1920
aatcgcagcc catccgccat ctacagcgcc aacctgaacg tgctcgggtt cgggccgttt   1980
gtcgtgacac atgcgctcgc gtacggtgaa ggctcgagcc gcgtggcgcc catgccggtt   2040
cttcccgtcc ccggcgcgcc catcaagctc atgccctaca gcgggatcga tctcaccctg   2100
cacccgctca ttccggcgcc acacgccgcc gcgcaggtga ccgatacgct cacgctgtct   2160
tcgcccacgg tgacggccgg cggtgcggag acgctctccg cctcgttcca ggcggatcga   2220
ccggttcatc acgccacggt ggagctcgag ctgtatgact cgacgaacga tctcgtcgcc   2280
acccacaccg tctcggatgt cgatcttcag ccgggatcgg ccacaagcga gacgtggagt   2340
ttcaccgcac cggccgcgaa cggcaattac cgcgttgagg cgtttgtgtt tgacccggtg   2400
acgggcgcga cgtacgacgc ggacacgcag ggcgcggttc tgaccgtcaa ccagccgcct   2460
caggcgacct acgcgacat cgtgacgaaa gacacggtca tcacggtgaa cgggacgacg   2520
tacgacgttc cggcacctga tgcgggcggg cactatccgt cggggacgaa tatttcggtg   2580
gcacccgggg acacggtgac cgtgcagacg acgtttgtca acgtctcatc gacggacgcg   2640
ctgcagaacg ggctcatcga catggaagtg gacggatcga acggggccat cctgcagaaa   2700
tactggccga gcacgactct tttgcctggc caatcggaga cggtgacggc gacgtggcaa   2760
gtgcctgcga atgtggcggc cggaacgtac ccgctcaact tccaggcctt caacacgagc   2820
agctggacgg gaaactgtta cttcacaaac ggtggcgtgg tcaacttcgt gatcagc     2877
```

<210> SEQ ID NO 2
<211> LENGTH: 816
<212> TYPE: DNA
<213> ORGANISM: Alicyclobacillus sp.
<220> FEATURE:

```
<221> NAME/KEY: misc_feature
<222> LOCATION: (1)..(816)
<220> FEATURE:
<221> NAME/KEY: misc_feature
<222> LOCATION: (1)..(96)
<223> OTHER INFORMATION: sig_peptide
<220> FEATURE:
<221> NAME/KEY: misc_feature
<222> LOCATION: (97)..(816)
<223> OTHER INFORMATION: mat_peptide

<400> SEQUENCE: 2
atgaacggca cctcagtctg gaaagcgtca ggcatcgcag ccgcctcgtg cctgacagcc    60
gcggcacttc tcgcctggcc ccacgccaca tccacgttgg acgcgtcgcc cgccatcttc   120
cacgcgccgc ggcacgcgct ctcgcccaac accagcccga aaccgaacag cgtccaggca   180
cagaactttg gttggtcggc gtcgaactgg tcgggatatg ccgtgaccgg cagcacgtac   240
aacgacatca caggcagttg gattgtgcct gcggtgagcc catccaagag aagcacgtac   300
tcttcgagct ggatcggcat cgacgggttc aacaacagcg atctcattca aaccggcacg   360
gagcaggact atgtcaacgg tcacgcgcag tacgacgcct ggtgggaaat cctccccgcc   420
cccgagacgg tcatctcgaa catgaccatc gccccgggcg accggatgag cgcgcacatc   480
cacaacaacg gcaacggaac ctggacgatt acgttgacgg acgtgacccg caacgagacg   540
ttctccacca cgcagtcgta ctcgggccct ggctcgtcgg ccgagtggat ccaggaggcg   600
ccggagatcg gcggccggat cgccacgctc gccaactacg gcgagaccac gttcgatccc   660
ggcaccgtaa acgcggcaa cccaggtttt accctgtccg acgcgggcta catggtgcag   720
aacaacgcgg tcgtgtctgt gccgtccgca cccgactcgg ataccgacgg cttcaacgtg   780 gcctacgggct ccaaccagcc gagcccaccg gcctcc                          816

<210> SEQ ID NO 3
<211> LENGTH: 945
<212> TYPE: DNA
<213> ORGANISM: Alicyclobacillus sp.
<220> FEATURE:
<221> NAME/KEY: misc_feature
<222> LOCATION: (1)..(945)
<223> OTHER INFORMATION: CDS
<220> FEATURE:
<221> NAME/KEY: misc_feature
<222> LOCATION: (1)..(75)
<223> OTHER INFORMATION: sig_peptide
<220> FEATURE:
<221> NAME/KEY: misc_feature
<222> LOCATION: (76)..(945)
<223> OTHER INFORMATION: mat_peptide

<400> SEQUENCE: 3
atgagaagac gcatgtcagg ctttgcgacg ggccttggca tcgcggcggg gctcgccctc    60
agttccgccc tcgccgcgcc gttcttccac gccgggaacg cgtccgcggc gtcgacgatg   120
tcgatggcgc cgacgagcac catgggcgcc ctgcccgcgc ccgaaggcgt gccggacgca   180
ggcccgctgt cgatcacgcc cgaggtcatt cgccaacaac aggctgacgc tgtccgggtc   240
atggacgaag aaggcctgaa gccacagatc ctctccggcg acatcaagcg attcaccctc   300
accgcgagcc aggtgaactg gtatttgtac cccggcaaag cggtcgtcgc gtgcggctac   360 aacgccaag tgcctggccc ggtcctccgc gtgcgcgtgg gcgatcgcgt ccaaatcctc   420
ctgagaaacg agctgaacga gcccaccacg ctgcacatcg agggcctcga tctgccggcg   480
tcgcagttgg gaatcggaga cgtcaccgaa tcccccatcc ctccgggcgg cgaacgcctg   540
tacagcttca ccgtgacgcc acagatggtg ggcacccacc tgtacgagag cggcacggat   600
```

| | |
|---|---|
| atggccagcg agatcgaccc aaggactgca cggggtgctg ctcgtcgatc cggcccgggg | 660 |
| atccctttat ccccaggcga aggtggacgc gctcttcgag atcgacgcgt ggatggtgga | 720 |
| cggatcgacc accgaaaacg cgtttggcct ggacggcaag ccgtatcccg acgcgcccga | 780 |
| actgacggtg ccgtacggca gccgcgtggt gctgcgcatc gtcaacgcga gcgggatgtg | 840 |
| ctaccacgcc atgcacctgc acgagacgac gttttggctg ctggcggaag acgggcaccc | 900 |
| cctcgccaag ccgcggccga tgaacgtgct cgccatcgcg ccagg | 945 |

```
<210> SEQ ID NO 4
<211> LENGTH: 1878
<212> TYPE: DNA
<213> ORGANISM: Alicyclobacillus sp.
<220> FEATURE:
<221> NAME/KEY: misc_feature
<222> LOCATION: (1)..(1878)
<223> OTHER INFORMATION: CDS
<220> FEATURE:
<221> NAME/KEY: misc_feature
<222> LOCATION: (1)..(66)
<223> OTHER INFORMATION: sig_peptide
<220> FEATURE:
<221> NAME/KEY: misc_feature
<222> LOCATION: (67)..(567)
<223> OTHER INFORMATION: propeptid
<220> FEATURE:
<221> NAME/KEY: misc_feature
<222> LOCATION: (568)..(1878)
<223> OTHER INFORMATION: mat_peptide
```

<400> SEQUENCE: 4

| | |
|---|---|
| atgggcttgt ggaaacggct ggcgctcggc gtgcctgcgg cacttagcat gctcgcggtt | 60 |
| ggggtgcctg tgatgagcgc ggacaccgtg gaggctgcgc cgcttgcgaa tccttcaacg | 120 |
| gaaaatgcgc aggatatggg gccggcgagt gggagccaga cggtgacggc atccatcatt | 180 |
| ttgcgtgtgc agaatccgac ggcgctgcag aactacattc aagagacgga gacaccgggc | 240 |
| agtccgctgt accataagtt cttgacgacg gcgcagttcg ctcagcagta cgcgccttcg | 300 |
| gcggcgaccc ttcagcagat tgagcaggag cttcagggct atgggctcca ggtcgtgaat | 360 |
| gtcgacgcgg atcacctgga catgcaggtt cagggcacag ttcagcagtt tgacaacgcg | 420 |
| ttcaacaccg tgatcgacct gtttaaggca aacgggcaca tcttccgcgc gccgaagaag | 480 |
| ccgccgcaga tcccggtggc gcttctcacc aacgtgctcg ccgtggtggg actcgatacg | 540 |
| gcacaggcgg cgcagtcgct cacggtgaag acgccgaacg tcgcgggtgt gccttcgccc | 600 |
| aaggtggtgc ttccgcaggg aggcagcacg gcgacgggca cgccagggag ctacacggtt | 660 |
| ggggatacgg cgaatcgcta cgacatcaac ccactctatc agaagggtat cacgggcaag | 720 |
| ggcgagacca tcggcattgt gacgctgtcg agctttaatc cgcaggatgc ctacacctac | 780 |
| tggcagggca ttgggctgaa ggtggctcca aaccgcatcc agatggtgaa tgtggacggc | 840 |
| ggtggccaga tggatgatgg atcggtcgag acgacgctgg acgtggaaca gtcgggcggt | 900 |
| ttggcgccgg acgccaacgt cgtggtgtac gacgcgccga atacggatca gggcttcatc | 960 |
| gatgcgttct accaggcggt ctcggacaac caggcggatt ccctctcggt gagctgggga | 1020 |
| cagcctgaaa tcgattacct gccgcagatg aaccaaggcc agtcgtatgt ggatgagctc | 1080 |
| ctcgccttca cccaggcgtt catggaggcg gcggctcagg catttccat gtacgcggcc | 1140 |
| gcggggatt caggcgccta cgacacggcg cgcgacttcc cgccctccga tggcttcacc | 1200 |
| acgccgctca gcgtggactt tcccgcctcc gacccgtaca tcacggctgc ggaggcacg | 1260 |
| acggtaccgt tcaccgcaaa gttctcgctc ggcacggtca acatcacgca ggagcagccc | 1320 |

| | | | |
|---|---|---|---|
| tggtcgtggc | aataccttca | aaacctcggc | taccaagggc tcttctccgt gggcacaggc | 1380 |
| ggtggcgtga | gcgtcatctt | cccgcgcccg | tggtatcagc tcggcgtggg cggcatgcaa | 1440 |
| aatagcgcgg | ccaatcaggc | cttcaccgac | tcgcagggcg ttttgtacgg atcgcccttc | 1500 |
| acgtacaacc | tgccgagcaa | ttacgcgggc | cggaatctgc cggacatctc catggatgct | 1560 |
| gatccggaga | cgggctatct | ggtctactgg | agcgcgggcg gtggctggat tgcgggctac | 1620 |
| ggcgggacga | gcttcgtggc | gccgcagttg | aacggtatca cggcgctcat tgatcaggag | 1680 |
| gtccatgggc | gagtgggctt | cctcaatccg | ctgctgtaca ccctgttgac gcaaggggtc | 1740 |
| caaggtgggg | cgcagccgtt | ccacgacatc | acgacgggga caactggta ttggaatgcg | 1800 |
| gtgcctggtt | acgatccggc | ctcgggcgtg | ggcacgccgg acgtcgcgaa cttggcgcag | 1860 |
| gacatcgcat | cgctgaga | | | 1878 |

<210> SEQ ID NO 5
<211> LENGTH: 1599
<212> TYPE: DNA
<213> ORGANISM: Alicyclobacillus sp.
<220> FEATURE:
<221> NAME/KEY: misc_feature
<222> LOCATION: (1)..(1599)
<223> OTHER INFORMATION: CDS
<220> FEATURE:
<221> NAME/KEY: misc_feature
<222> LOCATION: (1)..(72)
<223> OTHER INFORMATION: sig_peptide
<220> FEATURE:
<221> NAME/KEY: misc_feature
<222> LOCATION: (73)..(1599)
<223> OTHER INFORMATION: mat_peptide

<400> SEQUENCE: 5

| | | | |
|---|---|---|---|
| atgcgagcgc | tcgcacattt | ggccattggc | gccatcgcgt ccggcgtttt cgctgcacct | 60 |
| gtcgcttttg | cctcgccggt | tcaggaacgc | gtggtggtgg cctcgcccga tccgcggacg | 120 |
| cgtagcgttc | acgcggatgg | cgaaatttca | ccgtcgcagc cgatgcactt ggtcattacg | 180 |
| cttcgcctgc | gccacgaggc | gcagctcgag | cagctgattc gagacctgta cacgccggga | 240 |
| tcgcccgatg | caggtcactt | cttgacgccc | gcggcgttta acgcggcgta tgcaccgacg | 300 |
| gctgaggacg | tgcaggccgt | ggtccagggg | ctgcgcgcat acggcctccg cgttgagccg | 360 |
| acggtaaatc | ccatggtgct | gaccgtgagt | ggacgggccc gcgacgtcga gcgagcgttt | 420 |
| ggcgtgcatg | agctccaatt | tgggcgcgga | gctggcgcat ggtacgcccc ggatggtgcg | 480 |
| gccacgctgc | ctgcaccgct | cgccgcgcgc | gtgtcggccg tggtaggcct gacgagcgac | 540 |
| gcgatggagc | gccacctcgt | cctggcgcac | gtcgcgccgg caggaggtgg ctacacgccc | 600 |
| gcgcaaattc | agcgcgccta | cgactatacg | ccgctctaca gccaatacat ggggcgcgga | 660 |
| caggtcattg | cggtggtgac | ttccggctcg | gtgctccgct ccgacctgct cgcgttcgat | 720 |
| cgcgccttcg | ggcttccgaa | tccggtggtg | cgccagcggg tgatcgacgg atcgtccacg | 780 |
| tctcccgacg | acgagaccac | cctcgactgc | gagtgggcgc atgccatcgc gccgacggca | 840 |
| tcgctcgccg | tgtacgaggc | cgctcaaccg | gacgcgcagt cgttcatcga tgcgtttgcc | 900 |
| caggtggcgg | cggacgatgg | cgcgcatgtg | tcacgacga gttggggagc gcccgagtcg | 960 |
| gagaccgacg | cggcgaccat | gcaggcggag | caccagatct tcatgcagat ggccgcccag | 1020 |
| gggcagagcg | tgttcgccgc | ggcgggcgac | agcggatcgt cggacggaac aagcgggacg | 1080 |
| gacgtcgact | atccgtcgtc | ggatccgtat | gtcaccgcgt gtggcgggac gaggctcgtt | 1140 |
| cttggtgcgg | gtgcaaagcg | gctgcaggag | acggcgtggg ccgacacggg cggcggcgcg | 1200 |

```
agctcggtgt acggagagcc gtggtggcaa tatggcccgg cgtgccgca gacgggctat    1260 cggcagacgt gcgacgtcgc cctgaacgcc gatccggcca cgggctacga tttcatctat    1320
gagggtcagt gggaggtggc cggggggacg agctttgtcg cgccgatgat ggccgcgacg    1380
tttgcgctca tcgaccaagc gcgtgccctc gaaggtaagc cacccgttgg gctcgcagac    1440
gtcggcatct atgcgatggc gcgcaacgcg tcctacgcgc cgtacgcatt ccacgacatc    1500
acggccggat cgaacggcgc gtacagcgcg ggcccgggat gggatcatcc aaccggcttt    1560
ggttccatcg acgcgtacta cttttttgcac gggctcgac                          1599
```

<210> SEQ ID NO 6
<211> LENGTH: 1233
<212> TYPE: DNA
<213> ORGANISM: Alicyclobacillus sp.
<220> FEATURE:
<221> NAME/KEY: misc_feature
<222> LOCATION: (1)..(1233)
<223> OTHER INFORMATION: CDS
<220> FEATURE:
<221> NAME/KEY: misc_feature
<222> LOCATION: (1)..(123)
<223> OTHER INFORMATION: sig_peptide
<220> FEATURE:
<221> NAME/KEY: misc_feature
<222> LOCATION: (124)..(1233)
<223> OTHER INFORMATION: mat_peptide

<400> SEQUENCE: 6

```
atgcggcgtc gacgttggga ttacgaggac tggccgagtg agaacaggcg tgtcggcgtg      60
tggctcgcga gcgggaccgc gctgcttgcc atctgctaca tcctcggcat ctggacgggt     120
gcggcgctca cgcgcggtca ttcccagacg accgtggaat acgttcctcc ccagacgggc     180
aacaccgcga gcacgtccgg atcgctcacg ccgatcccgg gcgtcgagga cacgaccata     240
gtgacgcaga tttataaccg agtgaaaaat agcatcttta ccattacggc cgtctccgga     300
ggcaagccga cgtcgagcga cgcagaagaa gatatcggca cggggttcct gatcgatcac     360
aacggcgatc tcttgaccaa cgcgcatgtc gtcggatcgg ccacaacggt ccaggtgtcc     420
ggggacaacc gccaattcgt cggccgcgtg attgacgccg accagctgga cgatctcgcc     480
atcgttcgca tcccggcgcc caaatcgctg gaaccgctgc cgttgggatc ggtgaagtcg     540
cttcagccgg gcagcctggt catcgccatc ggcaacccgt tgagctgac ctcgagcgtc      600 agctcgggca tcgtgagcgg actcaaccgg tcgatgtccg agtcgaacgg gcacgtgatg     660
aacggcatga tccagacgga cgcgccgctc aaccctggaa attcgggagg cccgctgctc     720
aacgcggcag acaggtcgt cggcatcaac acgctgatcg aaagccctat cgaggggtcc      780
atcggcattg gctttgccat tcctatcgac cggtttatcc agctcgagcc agaattgctc     840
gccggcaaac ccgtcgcgca cgcctggctc ggcatcgagg gaatggacat cgacaacctg     900
atgcgtcaag cgctgcactt gcctgtggcc tcggcgtct atgtgaccga agtgaccccg      960 ggcggcccg ccgcgaaagc ggggctgcgc ggagattcga acgcggccaa gttgaacagt     1020
ctaagccagt cggccaatcc gtacgcgctg ctcaagggga acgggacat catcgtcggg     1080 attgacggca agcaggtctc cagcatcgaa cagttgacgc aggatatcaa ccaagatcaa     1140
ccgggtcaga cggtggtgct caccgtgttg cgcgcaggca aaaaccctgca cgtgcgcgtc     1200 acgctcggga cctggccatc cagccaaaat ccg                                  1233
```

<210> SEQ ID NO 7
<211> LENGTH: 633

```
<212> TYPE: DNA
<213> ORGANISM: Alicyclobacillus sp.
<220> FEATURE:
<221> NAME/KEY: misc_feature
<222> LOCATION: (1)..(633)
<223> OTHER INFORMATION: CDS
<220> FEATURE:
<221> NAME/KEY: misc_feature
<222> LOCATION: (1)..(90)
<223> OTHER INFORMATION: sig_peptide
<220> FEATURE:
<221> NAME/KEY: misc_feature
<222> LOCATION: (91)..(633)
<223> OTHER INFORMATION: mat_peptide

<400> SEQUENCE: 7
atgcgcaggt cttggagcgt gctcatggcc gtttgcatgt cttggttggc ggtggggtgt      60
ggcacgcctg caaactcgtt gtcacaagcg accgctgcgc tggaaggca cgcgccgcac     120
cccctcgtgt ttcagaacct acaggtgcc atgaacgagg ggcaggatcc ccggtgggac     180
ccgaaagcgg ctcccacggg tgtctacgac gacgtgaccg tggtcacagc gagtggccga     240
caggaggtgc tctccgttcg ggatgcgccg ctcctgttcg cagcgtactg gtgccctcac     300
tgccagcgca cactgcagct tctcacgtcg attgaatcac gcctgaagca aaagcccatt     360
cttgtgaacg tcggctatcc tccgggcacg acactgcaga ccgcggcgcg catcgcgcgc     420
gaggagtctc aagttcttca cttggcgccg ttccaagagg tctttatctt gaatcctgat     480
gcagggatc gatacgcccc gctagggtac ccaacactcg cttttatcg cgccgggcga     540
gattggacgc tgtacggtga acatcgagcg tctatttggg aaaaggcct gtccgaatcg     600
acatcaaaag cgtacaatgg cagcgaggaa tca                                  633

<210> SEQ ID NO 8
<211> LENGTH: 798
<212> TYPE: DNA
<213> ORGANISM: Alicyclobacillus sp.
<220> FEATURE:
<221> NAME/KEY: misc_feature
<222> LOCATION: (1)..(798)
<223> OTHER INFORMATION: CDS
<220> FEATURE:
<221> NAME/KEY: misc_feature
<222> LOCATION: (1)..(87)
<223> OTHER INFORMATION: sig_peptide
<220> FEATURE:
<221> NAME/KEY: misc_feature
<222> LOCATION: (88)..(798)
<223> OTHER INFORMATION: mat_peptide

<400> SEQUENCE: 8
atggatgaga tgaacattcg atcttggtgt gtcgctgctt gtaccgtagc cttgacaagc      60
gccgtgggcg cgacgaccgc gttcgcgcag acggtgaccg tacaacccgg acaatcgctc     120
tggaccatcg cacgcgcaca cgggatgccc gttcagttgg tggcgtccgc caatccgcag     180
tacaatccgc tgaatctccc tgttggtgcg accgtcacac ttcccagtct caaggacgtg     240
gctgtgcagc cgggcgactc cctgtttctg atcggcaggc aatatggcgt gtcgctcgcc     300
gagatgttgg ccgcaaaccc gaacgtggat ccattgaatc tgcaagtggg ttcaagtgtg     360
cgtgttcccc ttgcatcatc ttcgaccaag agctccacag tttctgccca tgttgccgca     420
tccacgcccg aaaactccaa caacctgtac tggttggagc gcgtcattca cgcggaggcc     480
ggcggagaat cgctgcaggc acaaatcgcc gtggccgacg tcattctcca tcgcatggcc     540
gcgggtggat acgggagcac ggtgcaacaa gtggtcttcc aagtgagcga cgggcactac     600
caattcgaga gtgtcgcaaa cggttcgatt tacggtcagc cagacgcaca aaacgtgcag     660
```

```
gctgctctcg acgcgttgaa cggagacgat gtcgtcccag gcgcgttggt cttctacaac    720
cccgcgcaga cgccttccgg aagttgggtt tggcaacaac ctgtggtcgc tcatatcggt    780
catctcgtgt ttgcgaag                                                  798
```

<210> SEQ ID NO 9
<211> LENGTH: 2304
<212> TYPE: DNA
<213> ORGANISM: Alicyclobacillus sp.
<220> FEATURE:
<221> NAME/KEY: misc_feature
<222> LOCATION: (1)..(2304)
<223> OTHER INFORMATION: CDS
<220> FEATURE:
<221> NAME/KEY: misc_feature
<222> LOCATION: (1)..(78)
<223> OTHER INFORMATION: sig_peptide
<220> FEATURE:
<221> NAME/KEY: misc_feature
<222> LOCATION: (79)..(2304)
<223> OTHER INFORMATION: mat_peptide

<400> SEQUENCE: 9

```
gtgaagacgc atcgcctgct cgcggtcgcg gcactgcctg caacagtgct gttgacaacg     60
ccggcgcccg cgctggctga gacctcgagc tcgcagagcg cttcggcgcc gtcgctgaac    120
gtgccggtcg ctgccctgac cctcgcgggt gttcaatcgt atcccatgct gagctacgga    180
tccacgggcg tgtacgtgga aattttgcag aacgccctga tgccctgggc tatgacgtg     240 ggacaagcca gcgggctgtt cgacgccacc acgcaggccg aagtgaaggc ttttcagcag    300
gcgatgggcc tgcagacgga cggcattgtg gtcccctga cctgggggc tttggcgaag     360 gcggtggccg attatcgcca ggtgatgacc gtactctcca gtcgcagctc gctggttcag    420
caagtcgaat ggaagcgcat cgtatggaac ggcaggttga tttcgaagcc catcggcttc    480
acgtaccagg ggacagcgta catgcccatt tggtacgtca tgcaggcgct tagcaaggcg    540
ggcattgcga gcacgtggca gggaggggtt tggacgctca cgccgcccgg aggtcagacc    600
gtgaattacg gaaagatctc gtacgggccg ggcagtgcgg ccatcgccat cggccagacc    660
gtggtcgcca atgtgcccgc ggtggtgtac cctgatccgg catccggaaa gctcacgacc    720
ttcatgcctg tttggtacgt catgaacgcg ttgcagcggc tgggcatcgg ttcgacgtgg    780
cagggaaccg agtgggacat gaagccagct cccgtcgtga tcgagacggg cgatccgtcg    840
aacaacacca ccgggtcaga tcccgcgaac agcacgggca acggcaccgg gaactcgacg    900
ggcaacgcca cgggcgccgt gccaggcggc aataccgtga cgaacgtcac cacgggctcg    960
tccaacgtca ccggcaactc gacgggcaac agtttgggga actcgacggg caacagcttg   1020
ggcaacagca cgtcgaacgc gacgggcaat gccaccggca caccaccgg gaatgcgacc    1080 ggcaattcca cgggcacgag cagcgggtcg ttcacgaatg tcgacctgcg ctatccggcg    1140
ccgtccaaca tcaatgcgca gagcatcaac cagtttctgc tgcagaacag ctcgccgctc    1200
aatgggctgg gcaattcgtt catggacgcc cagaacctgt acagcgtcga cgccaactac    1260
cttgtctcgc acgccatcct cgagagtgcg tgggggcaaa gccaaattgc ccttcagaag    1320
aacaatctgt ttggctacgg cgcttacgat tcgaacccg acaggatgc gggcgtattc     1380 ccgagcgacg actacgccat ccgattcgag gcgtggaccg tgcgcatgaa ctacctcacg    1440
ccgggcgcga gcttgtacgt gacgccgacg ctcagcggaa tgaacgtgaa ctacgccaca    1500
gccaagacct gggcaagcgg cattgcgcc atcatgacga gtttgcgag ctccgtcgga     1560 tcgaacgtga atgcgtacgt gcagtacacg ccgtccaaca atccgcccgc tccgagatcg    1620
```

-continued

| | |
|---|---|
| acagcggaac cggtgtacta catgaacggc gcgcaagggg taacgcagca ggatccgtat | 1680 |
| tacccgaatg gcggcgttcc gtactacccg accatcgcgc agggtgagaa tcagcagttc | 1740 |
| tttggccagc taagtgtcgg cagcttcggt caacccgtgg tggaggttca gcagttcctg | 1800 |
| aaccggacca tcaacgcggg gctgaccgtg gacgggcagt ttggcccgct gacgcaggcc | 1860 |
| gcggtcgaga agttccagtc gcaggtcatg cacatgtcga acccgaacgg catttggacg | 1920 |
| ttcagcatgt gggtccagta catccagcct tctcagtcga acgccaatct catcccggct | 1980 |
| gggaccaccg tgaaaattga ccaggtcgcc gagggcatgg cgggcccgta cgtcgtgcct | 2040 |
| tggtaccacg tggtgggcta tggctgggtc gactcgcagt atatcaagtt gaccaacgtg | 2100 |
| tatcgcgtca ttgtgcagaa cccggccgga acggccacca ccattcccgt ctaccaggtg | 2160 |
| ggcaacctgt cttcggtatt gctcaatctg cacagcggag actgggtggt tgccaactca | 2220 |
| gcgcagccct cgggcggcgt gtacaccatt cagattgcgg ctcaggatcc accgtgtcga | 2280 |
| acggctacgc cgccgggacg ctct | 2304 |

<210> SEQ ID NO 10
<211> LENGTH: 1791
<212> TYPE: DNA
<213> ORGANISM: Alicyclobacillus sp.
<220> FEATURE:
<221> NAME/KEY: misc_feature
<222> LOCATION: (1)..(1791)
<223> OTHER INFORMATION: CDS
<220> FEATURE:
<221> NAME/KEY: misc_feature
<222> LOCATION: (1)..(147)
<223> OTHER INFORMATION: sig_peptide
<220> FEATURE:
<221> NAME/KEY: misc_feature
<222> LOCATION: (148)..(1791)
<223> OTHER INFORMATION: mat_peptide

<400> SEQUENCE: 10

| | |
|---|---|
| atgatggccc acgatagatt ggacaggcga gtgaatgaga ggaggcaagc catgcgacgc | 60 |
| gcggcaaaat gggcaatcgc ccttggcacg acggcagtgg tggctggtgt cagcagcgtg | 120 |
| ttcgcacttc gcagtgtgcg agaagcaaac ctgaatccca acgcccctct cgcgaacgtg | 180 |
| cccgggcctc agggcgccta tacgcccatc agccgcgttc agcccgtcgt tccgaaaaac | 240 |
| gcgcggatcg accactacac gctgacggcg gaatcccgca cactgaccgt cggcggccat | 300 |
| gccctgcaag ccatgacgtt caacggcacc gcgccagggc cgttgcttgt ggcccatcaa | 360 |
| ggcgacgtcg tgaaggtcac ggtgcacaac cgcctctccg tccctctgac cattcactgg | 420 |
| cacggcatcg cggtgcccgg cgcggaagac ggcgtccctg gtgtcacgca aaacccaatt | 480 |
| ccgcctggcg ggagctacac gtacgagttt caggttaacc agcccggaac gtactggtac | 540 |
| cactcgcacg aggcgagctt tgaagaggtg ggcctcgggt tgtacggcgc cttcgtcgtt | 600 |
| ctgcccaaac gggcggtcca tccggccgat cgcgactaca cgctcgtcct gcacgagtgg | 660 |
| ccgaccgcat ccaccgcgca gacgatgatg gcgaacctca aggctgggaa cttgggattc | 720 |
| tcagcgaaag gcgaatccgc aggcatgggc ggcatgggca tgcaacaaaa cggggacatg | 780 |
| aacggcatgg gcatgatggg cgcggcggac ggcacgggtc agggaggaaa tagcgcgagc | 840 |
| gacatcgcgc acgtgttgcc tggccccccg cttcaactga acgttttttc gccgaccgca | 900 |
| aacgattggg ctgcgcttga cgaaatggcg ggcatgtatg acgccttcac ggtgaatcag | 960 |
| aacgcgagcg gtacaacgct cttgccagcc aagccggaac agctcgttcg gcttcgcatc | 1020 |
| gtgaacagcg gcaacatgac acacctgttc acgctggtcg gcgcaccgtt tcgcgtcgtg | 1080 |

```
gcgctcgacg gccacgacat tgccaacccc ggttggatcc gcggcgtctt gcttcccgtc    1140
ggcgctgcag agcgatacga catcgaattt cgcgtgccaa agtccggggc cgcattcctt    1200
gtgtgcgccg atcccgacac gactgcacag cgcgagcttc gcgccgccat cggtctgccc    1260
gacgcctggt cacaattcaa ggagacggat gcagcgagcc ttgaacgagc gccgtggttc    1320
gactttacac actatggcag cggcaggctg cccggcgaag ccgtgttccg cctgcatcag    1380
gcgtatcagg tacgctacaa catgaagctc accgtcggca tgtcgatgaa cggcatggtg    1440
tacgccatca acggcaaggt ctttccgaac atcccgccca tcgtcgtgcg aaagggcgac    1500
gccgtcctgg tccacatcgt gaacgacagc ccctacattc acccgatgca tctgcacgga    1560
cacgactttc aagtgctgac gcgcgatggg aaacctgtct ccggaagccc catcttcctg    1620
gacaccttgg acgtgttccc cggcgagagc tacgacatcg cgtttcgcgc cgacaacccg    1680
ggtttatgga tgtttcactg tcacgatctc gaacacgccg cggccggtat ggacgtcatg    1740
gtccagtacg cgggcatccg cgatccctac ccgatgagcg agatgtcgga g             1791

<210> SEQ ID NO 11
<211> LENGTH: 735
<212> TYPE: DNA
<213> ORGANISM: Alicyclobacillus sp.
<220> FEATURE:
<221> NAME/KEY: misc_feature
<222> LOCATION: (1)..(735)
<223> OTHER INFORMATION: CDS
<220> FEATURE:
<221> NAME/KEY: misc_feature
<222> LOCATION: (1)..(87)
<223> OTHER INFORMATION: sig_peptide
<220> FEATURE:
<221> NAME/KEY: misc_feature
<222> LOCATION: (88)..(735)
<223> OTHER INFORMATION: mat_peptide

<400> SEQUENCE: 11
atgaaacgtc ggaccttgct tgcgggcatc acgctggcgg cgctcgtcgc ggtggcgggc     60
tgtggcacgc cggccggtaa caccgcctcg ccggacaaca cagcgaactt gtcgaacacg    120
aacgcgccgg acacgctgtc caatgaaacc ggccagacgc tcgatacggc caacccgccg    180
tacctgcaca cgtcgaccga gcagtggaag agcatgccga agatgttcat caaccccgaac   240 aagacctatg acgccattgt ccacaccaat tacgggacgt tcaccatcca gctgttcgcc    300
aaagacgcgc ccatcacggt gaacaacttc gtgttcctgg cagagcacaa cttctaccac    360
gattgcacgt tcttccgcat cgtgaagaac ttcgtgattc aaacgggcga tcctcgcaac    420
gacggtaccg gcggcccggg ctacaccatc ccagatgaac tcagccatca ggtgccattc    480
acgaagggca ttgtcgcgat ggccaacacg ggccagccgc acagggcgg aagccagttt    540 ttcatctgca cggccaatga cacgcaggtc ttccagccgc ccaacaatcg ctatacggaa    600
ttcggccgcg tgatctccgg aatggacgtg atcgacaaga ttgccgccat cccggtgacc    660 gaaaaccca tgacgcagga agacagctat cctctgaaga ctgcgtacat cgagtcgatt    720
caaattcaag aatcg                                                    735

<210> SEQ ID NO 12
<211> LENGTH: 1824
<212> TYPE: DNA
<213> ORGANISM: Alicyclobacillus sp.
<220> FEATURE:
<221> NAME/KEY: misc_feature
<222> LOCATION: (1)..(1824)
<223> OTHER INFORMATION: CDS
```

```
<220> FEATURE:
<221> NAME/KEY: misc_feature
<222> LOCATION: (1)..(81)
<223> OTHER INFORMATION: sig_peptide
<220> FEATURE:
<221> NAME/KEY: misc_feature
<222> LOCATION: (82)..(1824)
<223> OTHER INFORMATION: mat_peptide

<400> SEQUENCE: 12
gtgaagaagg gaaagagatg gtccgccgcg ctcgcgacgt ccgtggccct gtttgccacc      60
ctgtcgcccc aagcgctcgc cagcgacacc gtggttccgc aagtgaacac gctcacgccc     120
attcatcacc tcgtcgtcat cttcgacgag aacgtctcct ttgatcacta tttcgccacc     180
tatccgaacg ccgccaatcc agccggcgag ccgccctttt acgccgcgcc gggcaccccg     240
agcgtcaatg gcctgtccgg aagccttctc acgcacaatc ccaacggcgt gaatccgcag     300
cgcctcgacc gttcccaagc cgtgacgccg gacatgaacc acaactacac gccggagcag     360
caggccgtgg acggggccg catggataac tttatcaata cggtcggccg cggaaatccc      420
atcgatctcg actactacga cggaaacacg gtcaccgcgc tctggtatta cgcgcaacac     480
ttcgccttga cgacaacgc gtactgcacg cagtacggcc gtctacgcc tggcgccatc       540 aacctgattt cgggcgacac cgcgggagcg acggtttatt cttcaagtga gaccagcggc     600
gccgcacaag tcgtgccacc cggcagcaaa aactttccga atgccgtgac gccaaacggc     660
gtcgacatcg gcgacatcga tccctactac gacagcgcct ccaaaggcat gaccatggcg     720
atggccggca aaaacatcgg cgacctgtta acgcgaagg gggtcacctg gggctggttc      780
cagggcggct ttgcaaatcc gaacgccaag gacaacaata tcgccggcac agatgaaacc     840
accgattaca gcgcacacca tgagccgttc cagtattatg cgtctacggc aaatccgaat     900
catctgccgc ctacgagcgt ggcgatgatc gggcgcacgg atcaggcaaa ccaccagtac     960
gacatcacga atttcttcca gcattgcaa acggaaaaca tgcccgccgt gagtttcctg    1020
aaagctcccg aatacgaaga cggtcacgcc ggctattccg atcccctcga cgaacagcgc    1080
tggctggtcc agaccatcaa tcaaatcgag gcgtcgcccg attggtcctc caccgccatc    1140
atcatcacct atgacgactc ggatggttgg tacgatcacg tcatgcctcc gctcgtgaac    1200
ggatcgagcg acaaggccgt ggacgtgctc ggtggcacgc cggttctgca aaacgggacc    1260
gacagggcgg gctatggacc gcgggtgccg ttcctcgtca tctcgcccta cgccaaacac    1320
aattttgtcg ataacacgct catcgaccag acttccgttc tgcggttcat cgaggagaac    1380
tggggcctcg gctcgttggg cccagcgtcg tacgactcgc tcgccggatc gatcatgaac    1440
atgtttgact ggaacacgca gaacccgcct gtgtttctcg atccgacgac cggtgaaccc    1500
gtgtccccag atatgcagcc ggaggtcatt cgcggcacca cgtatctcag cctgaatcac    1560
tacgctcaaa acctcgatgt cgtgctgcaa acctctcggg ggatggcgcg gttctcctac    1620
gaggggcacg aggtcgagat cgacgagcgt tccgggcttg tccgggtcga tggcgaagcg    1680
gtccatctca aggcgcctct tgtgcgggtg gacggcgtat ggatggtgcc cgtagaggaa    1740
atggattcgc tcattggggc cacgctgcac acctacaccg acggtcatct cacctactat    1800
ctcttttctc cgcaagacgc ccat                                           1824

<210> SEQ ID NO 13
<211> LENGTH: 750
<212> TYPE: DNA
<213> ORGANISM: Alicyclobacillus sp.
<220> FEATURE:
<221> NAME/KEY: misc_feature
```

```
<222> LOCATION: (1)..(750)
<223> OTHER INFORMATION: CDS
<220> FEATURE:
<221> NAME/KEY: misc_feature
<222> LOCATION: (1)..(75)
<223> OTHER INFORMATION: sig_peptide
<220> FEATURE:
<221> NAME/KEY: misc_feature
<222> LOCATION: (76)..(750)
<223> OTHER INFORMATION: mat_peptide

<400> SEQUENCE: 13
atgctgagct tgtggaagcg aatccgaacg ggaacactct cacttctggc tgcatgcgcg     60
tgcgcgctgt cggcgatggg cgctggggca ggatgggtgc atgcggctga gtcccaagcg    120
caagccccaa gggccattta caaggtggac acgaaggaaa aggtggtcgc tctcacgttc    180
gacatctcat gggggcaccg cacgcccgaa ccggttctcg agacactcaa gaagtgcggc    240
gtgaccaagg cgacgttttt cctgagcggt ccttggacca tgcaccacgc ggacatcgca    300
aagaaaatca aggcgatggg ctacgaaatt ggcagccatg gtacctgca caaggactat     360 tccaattacc cggactcttg gattcgagaa caggcgatgc tcgcagacaa ggccattcaa    420
caggtcactg gggtcaagcc gaagctgttc aggacgccaa atggcgactt gaatccgcgc    480
gtcatccgct gcctgacgag catgggctac acggtggtcc aatggaacac cgattcgctt    540
gactggaaaa acccaggcgt cgacgcgatc gtcaaccgcg tcacgaagcg cgtggtgcct    600
ggcgatatca tcctgatgca cgcgagcgac tcgtccaaac agattgtgga ggccctgccg    660
cgcatcattg aatcgcttcg gcagcagggc taccggttcg tcaccgtctc cgagctgttg    720
gcgggcgcca gcgttcaatc caaggtccag                                     750

<210> SEQ ID NO 14
<211> LENGTH: 972
<212> TYPE: DNA
<213> ORGANISM: Alicyclobacillus sp.
<220> FEATURE:
<221> NAME/KEY: misc_feature
<222> LOCATION: (1)..(972)
<223> OTHER INFORMATION: CDS
<220> FEATURE:
<221> NAME/KEY: misc_feature
<222> LOCATION: (1)..(63)
<223> OTHER INFORMATION: sig_peptide
<220> FEATURE:
<221> NAME/KEY: misc_feature
<222> LOCATION: (64)..(972)
<223> OTHER INFORMATION: mat_peptide

<400> SEQUENCE: 14
atgcggaaga cggctgcagg cgcgtgcgcc ctggcgctga tggggggtctt gggcggttgg    60 gcgggcgcgg ccggcacggc ggtgaacgcg cacgcgccgg cggcgtcggc gccaagtgtt    120
tcggcacatg tgtgggaaga agtcagccgc acgtggggaa cgcttcccgt cgatgcccgc    180
cacgacggcg tgtggcacaa catccccggt ttgtcaggct ttgcgctcga cacggcggcg    240
agcgagcgcg agaccgcgcg cgcgccatgac ggcgcgctcc acctggtatg gcgaaccctt    300
ccgccgaagc gaagactcgg agacctttcg cccgacgtga tttaccgcgg ccccgcgcag    360
gagaagtcgg tggcgctgat ggtgaatgtg tcctggggcg atgcgtacgt gcccaggatg    420
cttgaggtgc tgcgcagcgc gcacgtgaag gccacgtttt tcgtggacgg cgcgtttgcg    480
aagaagttcc ccgatctcgt ccgcgcgatg gcgcgagacg ggcacgcggt cgagtcccac    540
ggctttggac acccagactt tcgccggctg agcgacgcga agctcgccgc ccagcttgac    600
gagacgaatc gagtgctcgc cggcatcacg ggcaaggttc cacggctcat cgcgcctccg    660
```

```
gccggatcgt atgatgcgcg cctggctccg ctggcgcatt cgcggcgcat gtacgccatc      720
ctgtggaccg cggataccgt ggactggaaa aacccgcctg cggatgtcat cgtccaacgc      780
gttcagcgcg gtgcggaacc cggcgcgttg atcctgatgc atcccacggc gcccacggcg      840
gaggccctgc ctgatgtgat ccgctggctc gaggggcacg gttatcggct gaaaacggtg      900
gaggacgtga tcgacgaacg cccagcggtc acccctccga cgacgctggc gaacgagacg      960
ttccacagcg cg                                                         972

<210> SEQ ID NO 15
<211> LENGTH: 642
<212> TYPE: DNA
<213> ORGANISM: Alicyclobacillus sp.
<220> FEATURE:
<221> NAME/KEY: misc_feature
<222> LOCATION: (1)..(642)
<223> OTHER INFORMATION: CDS
<220> FEATURE:
<221> NAME/KEY: misc_feature
<222> LOCATION: (1)..(87)
<223> OTHER INFORMATION: sig_peptide
<220> FEATURE:
<221> NAME/KEY: misc_feature
<222> LOCATION: (88)..(642)
<223> OTHER INFORMATION: mat_peptide

<400> SEQUENCE: 15
atgatgcgtt ggaattggaa ggttgctgtg ggatcgttgg cgttggccgc actgggcgca       60
ggggcggcgg tgtcgccggt gtttgcggcg gcgaagtcgt cgaaggccgc gcagtcccac      120
gcagaggcga gcgcggcagt cgtgatggct gggaagctgt acggcaacat tccgaacgtc      180
accattcgcg gcgtggaagc tgggaaggcg ccgtgggtcg tggacggatc gtaccagctg      240
aagagcaacc tgttcacggc gagtgggaag tggctcatca ttccgaagca gggctatatg      300
gagaacggtc agccggttcc ggccaaaatt ggcggcacga cgaacaacat tccggccgtc      360
ggggccgaaa tcacgtttgc aaacgcggcg cccattgtgt tgccgccggt caagctgtcg      420
agccaaggtg acttctcgtt ccacgacgcc atccagtggc cgaagggtgc cgcgcagccg      480
gtcatcctga ttgggcccga agaacggt cagctcgtcg cgtggtttgc ggcgtcggac        540
ttcctcgccg actacggcca ggcgacgggc atgggcggcg gatgggtgaa cgcggcgcat      600
ccagagactc ccgtgcggca cacccacctc gcttcgaaga ag                        642

<210> SEQ ID NO 16
<211> LENGTH: 771
<212> TYPE: DNA
<213> ORGANISM: Alicyclobacillus sp.
<220> FEATURE:
<221> NAME/KEY: misc_feature
<222> LOCATION: (1)..(771)
<223> OTHER INFORMATION: CDS
<220> FEATURE:
<221> NAME/KEY: misc_feature
<222> LOCATION: (1)..(63)
<223> OTHER INFORMATION: sig_peptide
<220> FEATURE:
<221> NAME/KEY: misc_feature
<222> LOCATION: (64)..(771)
<223> OTHER INFORMATION: mat_peptide

<400> SEQUENCE: 16
atgaactggg cgcgtgtcgg cgcgtgggta tccacctggc tggtggctac ggcgcttgga       60
gctggctgtg ggacggcttc gcaagagcat ccgtccaaca cctccacgtc agatcaccgc      120
gttgcgcccg cggcgccagg cggctccgcc tcgatgcaaa accggcatat tctgcaggag      180
```

```
ccgctgccgc gtggcgtgaa aacggaaacg gatttgtaca actggctttt atggcagaga      240
ctcgccgaga tcaacaatcc ggcgcagggt gaaatctgcc tggacgccgc atgcaagatt      300
gcggccaccg tcttttctgg cccggccaag gccgcggccg gcacgcctgt cactctggtg      360
gcgttttcgc cgcgggcggg ttggcaggtg ctcgtgggtc cgctgcccca gtcggacaac      420
cctccgcgtc aagcacaatc catcacaggc cagtctgcgc gactacccgc gcaaagaggg      480
cgtatgcgtc gttcaaaccc acgaaatcga ctggtactgg attcaggacg dacacctgca      540
gctgatgcgt cagccgcgcg catgacgcgt cagctaaggc gatccgccag ctcgacgaac      600
gcgtcgagat cgcgcagggc aaagtcgatg gcgcgctgcc aaaagtcagg ttgcgtgaga      660
tccgcaccga tgtgttttg ggccagatcc tcgacccgca tgcgaccggt gtcgcgaagc      720
aacgccacat acttgtccgc aaatcccgtg ccttccgctg aggccatggc a               771
```

<210> SEQ ID NO 17
<211> LENGTH: 3390
<212> TYPE: DNA
<213> ORGANISM: Alicyclobacillus sp.
<220> FEATURE:
<221> NAME/KEY: misc_feature
<222> LOCATION: (1)..(3390)
<223> OTHER INFORMATION: CDS
<220> FEATURE:
<221> NAME/KEY: misc_feature
<222> LOCATION: (1)..(72)
<223> OTHER INFORMATION: sig_peptide
<220> FEATURE:
<221> NAME/KEY: misc_feature
<222> LOCATION: (73)..(3390)
<223> OTHER INFORMATION: mat_peptide

<400> SEQUENCE: 17

```
ttgaaacgca cactgagtgg cattgcttca gctgcaattg ttctgggtgc gattagcccg       60
atggcgtttg cgcagaccct cgtccagcggt ctcacgccgg ccggtcagtt gcctatcgtc     120
gtcaatggac aggttctgtc gaacccgtat gagatggtgg gcatggactc cggcaacaag     180
acgggcttct tcccgattta ctactttgac caggcgcttg aaaagattgg catcacggcg     240
acctggaatg gtgcaacccca cacctgggcg ctgacggact ccaacgtcaa tgcttcgaac     300
gtccaagtcg cgggtggtat gggcacgggg aacaccacgg tgaccctgaa cggcacgccg     360
attaagatgt tctacaccca ggttgcgaag gacccggcgg gtggcccggt cacgacgtat     420
atgccgattt actatatcaa caacatcctg agtgcgcttg ggatccatgg aacctttagc     480
ggacagacgg gtctcaacat taccaccggg cagacgcttg ccggtagcct gagtgccatc     540
acggtgacgg gggcgacgag cggtacgggg acctcttcga gcccggctgt ggcgttgaat     600
aacggcaagg ttacgctctc gacgactctg acggattcga atggcaatcc gattggcaac     660
gcggcggtca ccttcaactt ctctgaatat ggtgcgctgc cttcgaatgc gccgacggtc     720
accaatgcgt cgggtgcgac aattccggcg accaccggct cgacggctta tcagtacacg     780
gtctacacca actccagcgg tgtggcttcg atcacggtgt ctgggcccgt tggcttgacc     840
tacgcatacc aggtgactgc gacggcgccg atcagcaatg cagcaatca aatgattagc      900 agccagccgg cgtatgtcga gtttgtcgcc aacaaccagg cgggtattgc gccgtacggc      960
acggcttctc aaccgtactc ggcttcgctg gtaccgcag ttcccatcac ggtgattttg     1020
ccgccgggtg cgaacggtca gccgcaggcg aatgtgctcg tgaccctgtc gctgagcaac     1080
ccgaatggtg gcaccaacta tgcatacttc accaactcgt cgggtgcgaa tctgggcacg     1140
caaatccagg tgacgaccaa ctcgtcgggt gtggcgcaag cgtgggtcag cgacgcgaac     1200
```

```
gcgcagcctg ttgtcgtgac ggccaatgtg tcgaatgcga ccaatgtcag caacacttcg   1260
gtgagcacct acctgaactt tggtcaggca ggcgtgccag catcgatcgc caattacaac   1320
gatccgtatt cggctttggt ggccaacggt cagcagccgc tcgccggtac gacggtgacg   1380
attacgggta cgctcgtaga cgctgcaggc aacccggtgg ccaacggtca ggtgcttgta   1440
accggctcgt cgtccagcgg cgacttcggc tatgtcacga cgtccaacgg caagagcacg   1500
acgaccgact ccccgagcgt gggtacgttg cagcctggtc agcctgtgag ctccgcgctg   1560
ggtgacgtca tcacggcgga tgcgaacggc aacttctcgt tgcaagtcac agacacgcag   1620
aacgagcaag ccagcctgac gttctactcg gtgagcaacg gggtcattag cccggtgggg   1680
gtcattaaga ccgacacgct gaaattcgca gtgaacaatc agctgtcgac cattgcgctg   1740
ggtgcgacgg acgctcaagc ggacggcaac cagtacacga atctgacggg tctcacgggt   1800
tcggacaatg cgccggtgcc ggtgtatgtg gatccgcaga atccgtcggg cacaatggtg   1860
accaatcaga gcatcaccta tacgctcagc gtcagcagcg gcgacatcgt gggcattggc   1920
tctggtgcgt atctggcgcc gaccaatgcg aacaacagca cgattccgat caacagcggc   1980
aacggcctca gctccgtcca ggtcacggtc acggcattgg gcaacaacca ataccagatc   2040
tcggtgcccg gtcagcaagg cgtgttgacg acctcgtcgc ctgactttac ggtgctggtg   2100
aaaggctcga cggttcgac gaagctgacg gtcagctccg gctcactctc gtcgacggca   2160
accatcacct tcacgtcgag caacccgacg gtggtggcta gcctgacgcc agtttcctcg   2220
gtgttggcgg ctggtcagaa cgagacggtc accttcaccg tggaagatgc agatggcaat   2280
ccggtgagcg gtaatacgca ggttgccatc acggcgcatg acagcaatga tccgttgtgg   2340
atcaccgcag tgaatggcac aaacttgagc gagtatgaga cgattaatgg tgctgcaacg   2400
tctgtcagca cgccgattcc gctcggtacg agttcgtatg caacctctgg tggttctacg   2460
ctctacccgg cttacacgaa cagcgggtac tttaagaatg gtgtgagcat cagcggtgtc   2520
gtatcgtggg atggtacggt gggcgatcca atctacgtca ccaccaactc gcaaggccaa   2580
gtcacgctga ccttgcaaaa cggcaacgtg acctattttg acggaaacaa caccacgttg   2640
tcgaatggca tcagcgttgc cggtacgagc ggaagtgaag ggttctacac atattcgagc   2700
gataccgcag cgacacgtc ggatcttaca aatatgggcg tgttggtcat tggtcaagcc   2760
aatggtgacg cttcaacgtc gctcggaacg atttacatcg gcagtggtgg tgctacgcag   2820
acaccggccg ccttcaccta cgtggatgcc aataaccact cttacacgta ctcgaacacg   2880
agcgatacat ttacggtatc tagcacccag agtgttagcg gtggcaacta tgcgatcaca   2940
agcttcacgc cagttggagg tactgcaact tctacaatcc cgagtggcgt gagcgtaaat   3000
agctcgacgg gtacggtttc ggtgtcccaa aacgctgcag tcggtacgta caccgtgagc   3060
tattacctga acggcgtcac tgaatccact ggcacgttca aggtgtactc cggcagcggt   3120
gtggctccta cagagatcac tggctcgtca gtgacggttc ctgctgcaac gtactcgggt   3180
acgttgaaaag tcacggtaag caacggtggt tcgccgctgt acgtgaacgt taccgctgga   3240
gaatcggcca atgcggtggc tgcagctatt tacaacgcgc ttgtcaatgc caatatcagc   3300
ggagatacct tctctgtttc gggttcgaca gtcagcgtga ccgctgcgag cggttcgccc   3360
acgctcacag ttgtcgatgc gaccaatttc                                    3390
```

<210> SEQ ID NO 18
<211> LENGTH: 744
<212> TYPE: DNA
<213> ORGANISM: Alicyclobacillus sp.

```
<220> FEATURE:
<221> NAME/KEY: misc_feature
<222> LOCATION: (1)..(744)
<223> OTHER INFORMATION: CDS
<220> FEATURE:
<221> NAME/KEY: misc_feature
<222> LOCATION: (1)..(123)
<223> OTHER INFORMATION: sig_peptide
<220> FEATURE:
<221> NAME/KEY: misc_feature
<222> LOCATION: (124)..(744)
<223> OTHER INFORMATION: mat_peptide

<400> SEQUENCE: 18
```

| | | | | | |
|---|---|---|---|---|---|
| gtgcgaatta | tgaaagtttt | gggatggatt | ttggtaccgt | atatcatgct | gtttattcag | 60 |
| tgggggcgaa | tgaacagaat | tctgcgtttt | gccggttcat | tgtgggcatt | aattgtcttc | 120 |
| gcgaacacgg | tgtatatgat | tcgaggaaac | acaccgcgga | acgcatcaac | ggtaagcgct | 180 |
| acaacttctt | tggttaattc | gacgaatagt | tcacaggtag | caaagcaaga | gcaaaactcg | 240 |
| agtacgtctc | ccgctcataa | gtctacgaac | tcattgcaac | atgcgcaaca | tcaagctgct | 300 |
| acgacttcat | cttctcagtc | gaagttacga | tatatcccgt | tcacacata | cgggaaggta | 360 |
| ggagacttgg | aaattagagt | taactccctg | cagcaagtta | agagtgtggg | gtacgacggg | 420 |
| ataggtgaaa | ccgcaaatgg | tgcgttttgg | gttatcaaca | tcaccataag | aaatgacgga | 480 |
| tccactccta | tggaggtcgt | tgatggcata | ttccatttgc | agaacttaaa | cgggaacgtt | 540 |
| tatcagccgg | attctactgc | tgagatatat | gcaaatacaa | attcagggac | tattccgacc | 600 |
| gacctcaacc | ctggtgtgtc | catgacgaca | aatctcgtat | ttgatatgcc | ggattttatg | 660 |
| acatatggtc | acgtcgggca | gcattactca | cttgtcgctt | ccatgggttt | cttcgggtca | 720 |
| gatgaaacga | cgtatgctct | tccg | | | | 744 |

```
<210> SEQ ID NO 19
<211> LENGTH: 516
<212> TYPE: DNA
<213> ORGANISM: Alicyclobacillus sp.
<220> FEATURE:
<221> NAME/KEY: misc_feature
<222> LOCATION: (1)..(516)
<223> OTHER INFORMATION: CDS
<220> FEATURE:
<221> NAME/KEY: misc_feature
<222> LOCATION: (1)..(75)
<223> OTHER INFORMATION: sig_peptide
<220> FEATURE:
<221> NAME/KEY: misc_feature
<222> LOCATION: (76)..(516)
<223> OTHER INFORMATION: mat_peptide

<400> SEQUENCE: 19
```

| | | | | | |
|---|---|---|---|---|---|
| atgaaccgca | aatccatgtt | gtctgtgttg | ggtgtggcag | ccgcagtagc | cctgatggtg | 60 |
| acgggctgtg | gcacggccaa | cagcacgaac | aacacggcgt | cgagcggtgc | ggccagcaca | 120 |
| gccgtcacgg | tgaagcacga | gcacaagggg | gccaatgctt | cgaagacaga | gacgaagcag | 180 |
| accgaagcga | agtcgtcgaa | caaggctgga | gaaacggcga | agtcgtcggt | gaagctcacg | 240 |
| gccccggtgg | caggcgcgac | ggtgacggcc | ggcggcacgc | tgaaggtgag | cggccaagtg | 300 |
| tcgtcgaacc | tcgcgaagaa | ggacgtgcaa | attacgttga | caaatagcgc | gaagaaggtg | 360 |
| ctcgtgcagc | agatcgtcgg | tacgaatagc | accggcgcat | tcgtggacac | gctcaagctt | 420 |
| ccaaagtacc | ttgggaaagc | cggaagcgac | ctgacgctgt | cggtgtccgt | cgttggcgaa | 480 |
| aatggagtcg | taagcaccct | tgtcgctgca | cgtgaag | | | 516 |

```
<210> SEQ ID NO 20
<211> LENGTH: 726
<212> TYPE: DNA
<213> ORGANISM: Alicyclobacillus sp.
<220> FEATURE:
<221> NAME/KEY: misc_feature
<222> LOCATION: (1)..(726)
<223> OTHER INFORMATION: CDS
<220> FEATURE:
<221> NAME/KEY: misc_feature
<222> LOCATION: (1)..(90)
<223> OTHER INFORMATION: sig_peptide
<220> FEATURE:
<221> NAME/KEY: misc_feature
<222> LOCATION: (91)..(726)
<223> OTHER INFORMATION: mat_peptide

<400> SEQUENCE: 20
atgaggcgcg cggttcgtat actagctgcg ctactgtttg gctggcgac    ggtaacagcc      60 acattgatgt tcgtgcctca ggcaagagcg gccacggtga caggagcgtt ggcgcaatcg     120
caagtggtgt ccattacggg cggctacaac acgacgacac agatgtatga gcagacgggt     180
cagcaaaccg tcgttacgaa ttggacctttt tctcttcaac aaactgtcaa ccaaaacaac     240
gagaatccgt cctacgctca atgcacagtc ttggcgggaa accagcaggt aacgtgcacg     300
tcggacgcta cgaataacgg tgcaatttgc acatcccccct atcctggagc tattgacaag     360
caatgcacga acctgattgg gttcactgga acatatcag tgagttcgca aaacggcaat      420
ccaacgttca cttttctct tccgagcatc gacccgagta ccatgaagcc agttgggatc     480
tttgtgacgc tgagacgat ctatggtcag atgggaacag gtccgaaag ttatttaagc       540 tcaggtcaat ctggaggatg gtcatttaac ttttccaacg tctcagatcc tcaagattgg     600 tatttctcc ttgagttttt ggcgaatcca attgtcgcgg ccattgctgt gcccaccact      660
caaacggttc cgattatag ctgggtcacc accacggttt ggcacccccgt tcaaatttcc     720 tacagc                                                                    726

<210> SEQ ID NO 21
<211> LENGTH: 540
<212> TYPE: DNA
<213> ORGANISM: Alicyclobacillus sp.
<220> FEATURE:
<221> NAME/KEY: misc_feature
<222> LOCATION: (1)..(540)
<223> OTHER INFORMATION: CDS
<220> FEATURE:
<221> NAME/KEY: misc_feature
<222> LOCATION: (1)..(72)
<223> OTHER INFORMATION: sig_peptide
<220> FEATURE:
<221> NAME/KEY: misc_feature
<222> LOCATION: (73)..(540)
<223> OTHER INFORMATION: mat_peptide

<400> SEQUENCE: 21
gtggttcgga tgcgcaagcg gttgggactt gttctgagta tggtgacatc tgtgttggtt       60
ggatgtggcg cttcacatcc gtctccattg aaccaagaca atctttgtt gacgtggaac      120 gctgctaaac acgaggtgcg gtggaaagtg gtcgccggcg acggacgcgc aaacggcggt     180
atgaacttcg atggctatgc caatggcagt atgacactgg tcgtgccgat gggtggcgc      240 gtcgtgatcg actttgacaa tgccagttttg atgccgcaca gcgcgatggt ggtgccttac    300
ggagatcgcg aacgctccaa cttgacgca acgatggttg cgtttccagg cgcagaaacg      360
cccaatccgt cacagggaga ccctcaaggg acgcatcggg atgtcatctt cactgctgcg     420
aaggtgggaa cgtatgccct cgtctgcggg gtcccgggtc acgcgctggc gggaatgtgg     480
```

```
gatcagcttg tggtgtccga tgaagcgaaa cacccgtccc ttcgcgtgca acgcgactca    540
```

<210> SEQ ID NO 22
<211> LENGTH: 1431
<212> TYPE: DNA
<213> ORGANISM: Alicyclobacillus sp.
<220> FEATURE:
<221> NAME/KEY: misc_feature
<222> LOCATION: (1)..(1431)
<223> OTHER INFORMATION: CDS
<220> FEATURE:
<221> NAME/KEY: misc_feature
<222> LOCATION: (1)..(75)
<223> OTHER INFORMATION: sig_peptide
<220> FEATURE:
<221> NAME/KEY: misc_feature
<222> LOCATION: (76)..(1431)
<223> OTHER INFORMATION: mat_peptide

<400> SEQUENCE: 22

```
atggcggttc gtagagcgtg gcttctggcg cccttgtgcg cgagcagtct ggtcgtcccg     60
gcctcggtgc aggccggatt ggcccaggga catggcagct tttcgacggt tcgcgtgtcc    120
gtggggacgt cgagttccct gtccgtcccc gcgctgattc agggaaacga aacgtacatt    180
ccgctgtggg acctcatgca ggtgctccat cagctcggct tcaccgcgac gtgggcgaag    240
ggccaattca gcgtttcggc cccgccatcg gtgccgatgg acgaggcgcc tgggccagcg    300
ggcaaaggcg gggcgctcgt ggtgctcgac gggcaagtcg tggaacaggt gccgacggtc    360
atcgccacgc caccggggc ggccaccct gaggtgtttc tgccgctcac gaacgcggag    420
gagatcctcg gtcggttggg cattcaggcc agcgcgaccg gcaatcaggt gaacctcgac    480
gcgtcggctg tgccccaggc gcttcccaac cagcaggtgg ctgtgtggaa cgtgcttgcc    540
gctgttgcgt ccgatctcgg cgtgtcgacc gcgccagccg ggccgagtcc ctacgccgac    600
ttgccgacag cctcgccggc gtggggcgcg gtggaggcgg ccattcgtct gggctggtat    660
tcgcccttat ccgcgtcgtc atccggcgcg tttcaaccca tcacgtgggc gcaaacggca    720
tccattctgt ggaatgcgct cggcatttca cagcaggacg cggcgtacca gccaggcgga    780
tcgccgacgg cgtgggcgag cgcccttggc cttgttccag aaaactggga tccagcgtcg    840
tacatgaccg cgcaggaatt ggacaccttg gcgtcgaatt tgcacgaatg tctgcaagga    900
gatgtcgaaa cgggcgccaa cacgtggcgg ctctggtatc cgccggctga cgaagtggag    960
gctaccctcc agtcgggagg cgggcagtcg ctgttcacct cgaccgctga cgcgcaggcc   1020
gccatctcgt cagcctacca attcttcaat cagcttgtgg tcacaagagt cggccaaggg   1080
tatgtcgtca ccgttccctc tgtgcctgag ggatatgggt ttgccacctt ttctgcgctc   1140
ggcggtgtgg cttaccagac gacacccggc ggtccgtgga cggtcgtgcc cgtgctggac   1200
acgcgcgacg tctccatccc ggccaagggc cgtctcagtg tcaaggttcc cgcgcagggc   1260
atcaccatca cgtggaatca gatgatgcca tcgctgggcg aacggtggc catgggcgcg   1320
ctccaggtgt cgcctggacc cagcgggcct tcggtcgagc gcttgaatat cgtcacaccg   1380
aacttacctc cggtccttcc gtcgtccgtc acttctacgc aaccgcagtc a            1431
```

<210> SEQ ID NO 23
<211> LENGTH: 1020
<212> TYPE: DNA
<213> ORGANISM: Alicyclobacillus sp.
<220> FEATURE:
<221> NAME/KEY: misc_feature
<222> LOCATION: (1)..(1020)
<223> OTHER INFORMATION: CDS

```
<220> FEATURE:
<221> NAME/KEY: misc_feature
<222> LOCATION: (1)..(57)
<223> OTHER INFORMATION: sig_peptide
<220> FEATURE:
<221> NAME/KEY: misc_feature
<222> LOCATION: (58)..(1020)
<223> OTHER INFORMATION: mat_peptide

<400> SEQUENCE: 23
gtgaatcgac agtggaggct agcggtggcg acttctgccg tcgcggccag cctcgcgggg      60
tgtggagcac cggacctcgc ggcgatgcgc ccgacggtcc aaaagtctgc ggtactcgtg     120
gaggtcgtgg gcgcgccgcc gtttgcgccc tcagcttcac aactgggaac ggcaggggcc     180
acctccgtcg aggtggttca cgttgcccct ggcgaatggc agtctgtcgc ggcccacgca     240
ttggcgaagg gcaattgaca gggggtcatg gtcgtgtgcg acgacgcgaa cgccgtcgcg     300
tctggcctca accaacttgc tgccgaccat cccgacgttc gctttctcgt ggtcagcaac     360
tggccggctt cgcaaatcac ctccggaaac gtggaagacg tcgcacagga tcctgtggcc     420
gtcgcttaca gcattggcgc gctgtgcgga gactggatcg cgagctcaac gtcgacgagc     480
ggagcggtat acagcggcgt gcccagcatc gtctacgcgc cgcgcggtgc gaccgtggct     540
gaacaaaaag ccttcttcac gggtctgtat caggcgaacc ccaatgtccg ggtcgtcgcg     600
cttccgcagc ccgctgcgca gagcctgtcg agctatgggt acgcggtgga tttgggtgtg     660
gtaggcgggt ctcctgcggc aggggaactg tcggcgcttc gcagtgccgc cccgcctgg      720 gctgcttttg gaacgtcgcc gatcgctggc tttgcgattt ctcctggcca tctgtcgtcg     780
tcggaggccg tgcaagcatt ccaggcgctc gtgtcgccgg acgcgtggca ctcgggtgag     840
catctcgtgc tcgacttgtc ttcggtggcc ttcgacgaca gcaggtgcc cgcgaccgtc      900 atcgcggcgt gggccaagct ggaggtcaac gcgatcgcgg ctgcagcgca atcgaacgcg     960
gccttcgcgt cactgccgcc gagcgtgcgc tcggacctcg ccaatgcgtt tcatttgtca    1020

<210> SEQ ID NO 24
<211> LENGTH: 1023
<212> TYPE: DNA
<213> ORGANISM: Alicyclobacillus sp.
<220> FEATURE:
<221> NAME/KEY: misc_feature
<222> LOCATION: (1)..(1023)
<223> OTHER INFORMATION: CDS
<220> FEATURE:
<221> NAME/KEY: misc_feature
<222> LOCATION: (1)..(87)
<223> OTHER INFORMATION: sig_peptide
<220> FEATURE:
<221> NAME/KEY: misc_feature
<222> LOCATION: (88)..(1023)
<223> OTHER INFORMATION: mat_peptide

<400> SEQUENCE: 24
atggtcatgc gcactcggtg gattcgatgg atggctttgg ctctcgcagt ctgtgtctgg      60
ctcagcccgt ttcccttctc gtggggcgcg acgagcctcg acgctgatct tccacaaccc     120
acgattccgc catccgcgtg gagcaacctc aatcaggact ggaaggacct tcagcgcttg     180
gcgcaaaaca cagtgccgcc ctcgaaagag agcagccaga cccacgcgcc cacacacaag     240
tcatcgcaac cgcctgccca gtcccgcaa gggccgctcg tcggggtcgg cgatacgggc       300
gaagcggccc ggtggttaaa cgaagccttg gccgtgctcg gctatttgcc gccgtcttc      360 tctcccgcgg cgcagacgtc cacccgtcag gtgcggctcg cactcgcggc gagcgccgag     420
catcagacgc tcgtgcccat cccaggctcg tttcaacttc tgtatcacgc gccaagctcg     480
```

| | |
|---|---|
| tgggtggcgc tctggtccgc cgacgaagac acgccgatca cggagggcgc cgtcatggcg | 540 |
| tttgaagcac aacatcacct gggcgtggat ggcattgccg ggccggacgt cattcatgcg | 600 |
| ctggcgcagg ccctcgccgg caatgagacg gcagaaaagg cgccctacag ctacatcctg | 660 |
| gtgaccacgt cgttgcccga gacgctcgaa ctctgggtga atggccagct tgtcctcaaa | 720 |
| tcgctgtgca acacaggcat cgcgcagtca cccacgccgt atggcacgta cggcgtctac | 780 |
| gtgcagtaca cgtcgcagga aatgaagggc aaggatccgg acggcacgcc ctacgacgat | 840 |
| cccggcgttc catgggtgag ctacttctac aaaggttgcg cggtccacgg tttcctgcgg | 900 |
| gcaaagtacg gctttcccca gagcctcggt tgcgtggaac tgccgtatgc cgcggccaaa | 960 |
| acggtgttct cctatacgca catcggcacg cttgtcaccg tcaccgcctc cccgctttcc | 1020 |
| gcg | 1023 |

<210> SEQ ID NO 25
<211> LENGTH: 1197
<212> TYPE: DNA
<213> ORGANISM: Alicyclobacillus sp.
<220> FEATURE:
<221> NAME/KEY: misc_feature
<222> LOCATION: (1)..(1197)
<223> OTHER INFORMATION: CDS
<220> FEATURE:
<221> NAME/KEY: misc_feature
<222> LOCATION: (1)..(84)
<223> OTHER INFORMATION: sig_peptide
<220> FEATURE:
<221> NAME/KEY: misc_feature
<222> LOCATION: (85)..(1197)
<223> OTHER INFORMATION: mat_peptide

<400> SEQUENCE: 25

| | |
|---|---|
| atggataggc tgctgaacaa caaggtggcg cttcgcctga ccgcgctcgt cctcgcgtgc | 60 |
| attctctggc tcgccgtgca cgcggagcag gggtcggggt cctccgcgtc cacgggagtg | 120 |
| accgagtcgt tcgagctgcc ggtgcgggtg gaaacctcgg ccgacgaggt gttggtgtct | 180 |
| caagttccga ccatcaccgc ccgggtgacg acgaacctgt tgagcctgcc gacgctggcc | 240 |
| tcggatatga tgaaagccga gatcgtcgcg gacgccgaaa atctgggccc gggcacgtac | 300 |
| acgttgcacg tggcggccgt caacatgcct gcaggggtgc gatcgtacac gctaacgcct | 360 |
| tccaccatca cggtgacgtt ggagcccaaa gtgacggtgg agcgaacggt gcgggtgaac | 420 |
| gtggtcggca cgccagggca gggatatgtc ctcggcaagc ccgagctcgg cgcggggggtc | 480 |
| gtcgaggtct cgggcgccga atccagtgtg caggccgtgg ccgaggtggc gggcgtcgtg | 540 |
| gacgcgagcg gcctgtcgca gacggcgacc aagctcgtcg agttgttgcc gcttgaccaa | 600 |
| gcgggcaagg cggtgccggg tgtgacggtc acgccatccg cgatttcggt cacgctgccg | 660 |
| atcacgtccg ccaatcaggc ggtgaagctg acgcctgcgg tcaccggcag ccctgcgcct | 720 |
| ggatacgccg tcgcctcggt gcacctggag cccgcgagcg ctgtggaaca ggggctagcg | 780 |
| gccagccagc ttccgcagcg cgggctcctc gtgcccatcg acgtcactgg attgaaccgg | 840 |
| cccacgacgg tgtcggtccc ggtgccgctt ttgccgggga tgacgagcgt ttcgcccacg | 900 |
| gcagtgacgg ccgtgatcga cgtggagccg tccgccgtct acaccgtttc gaacgtcccg | 960 |
| gtggccatca cgggcgcgac gggtgtcaag ctggtgacgc tcggaccgt gaatgtcacg | 1020 |
| gtgacgggga tcgaggccga cgtgcgcgcg gtggagaggg atccggccgc ggtgcaggcg | 1080 |
| tttgtggacg cgaccgggtt gacacatggc tcggcgacgc tgcccgattc aaattcgtct | 1140 |
| gctgtcctgt ctcttgtgat ccggccacgg gaaaggcgta agcgaacaca tgtagtg | 1197 |

<210> SEQ ID NO 26
<211> LENGTH: 959
<212> TYPE: PRT
<213> ORGANISM: Alicyclobacillus sp.
<220> FEATURE:
<221> NAME/KEY: SIGNAL
<222> LOCATION: (1)..(24)
<220> FEATURE:
<221> NAME/KEY: mat_peptide
<222> LOCATION: (25)..(959)
<223> OTHER INFORMATION: acid endoglucanase or acid cellulase

<400> SEQUENCE: 26

```
Met Lys Thr Arg Trp Ser Gly Ala Leu Ala Val Leu Ile Ala Leu Gly
            -20                 -15                 -10

Thr Gly Ala Ser Pro Ala Trp Ala Ser Val His Ser Ala Ala Thr His
         -5                  -1   1               5

Ala Lys Ala His Val Gly Val Arg Ala Ala Asp Met Ala Ala Ala Ser
         10                  15                  20

Met Ser Ala Glu Ile Gln Ile Leu His Asp Ala Leu Thr Ala Ser Glu
 25                  30                  35                  40

Leu Ser Ser Val Gln Ala Ala Gln Ala Ala Asn Leu Pro Ala
                 45                  50                  55

Ser Thr Trp Val Ser Trp Leu Tyr Pro Ser Ala Ser Pro Ser Ala
                 60                  65                  70

Ala Gln Thr Gln Thr Ala Gln Ala Leu Gly Ala Leu Leu Thr Leu Val
         75                  80                  85

Thr Tyr Gly Ala Val Ala Asp Asp Gly Gln Asn Ile Ala Gln Asn Leu
 90                  95                 100

Gln Thr Leu Gln Ser Thr Ser Pro Leu Leu Ser Pro Ala Ala Val Ser
105                 110                 115                 120

Met Phe Tyr Gln Asn Phe Phe Val Leu Gly Gln Ser Ser Lys Ser
                125                 130                 135

Val Leu Ser Gly Gln Ala Thr Thr Ser Thr Ala Gly His Ala Leu Ala
                140                 145                 150

Gln Ala Ala Leu Thr Pro Gln Leu Ala Ala Tyr Leu Arg Gln Ser
        155                 160                 165

Gly Leu Ser Pro Asp Asp Leu Ala Arg Ala Tyr Val Ser Phe Ala Ser
        170                 175                 180

Ala Val Asp Ser Gln Gly Ala Ala Gln Thr Ala Leu Leu Thr Arg Ile
185                 190                 195                 200

Cys Thr Asn Ile Leu Gly Phe Gly Ala Pro Thr Ser Thr Ala Thr Ile
                205                 210                 215

Thr Val Asn Ala Ala Ala Asn Leu Gly Gln Val Pro Thr Thr Ala Phe
                220                 225                 230

Gly Leu Asn Ala Ala Val Trp Asp Ser Gly Leu Asn Ser Gln Thr Val
        235                 240                 245

Ile Ser Glu Val Gln Ala Leu His Pro Ala Leu Ile Arg Trp Pro Gly
250                 255                 260

Gly Ser Ile Ser Asp Val Tyr Asn Trp Glu Thr Asn Thr Arg Asn Asp
265                 270                 275                 280

Gly Gly Tyr Val Asn Pro Asp Asp Thr Phe Asp His Phe Met Gln Phe
                285                 290                 295

Val Asn Ala Val Gly Ser Thr Pro Ile Ile Thr Val Asn Tyr Gly Thr
                300                 305                 310

Gly Thr Pro Gln Leu Ala Ala Asp Trp Val Lys Tyr Ala Asp Val Thr
```

```
            315                 320                 325
His His Asp Asn Val Met Tyr Trp Glu Ile Gly Asn Glu Ile Tyr Gly
    330                 335                 340

Asn Gly Tyr Tyr Asn Gly Asn Gly Trp Glu Ala Asp Asp His Ala Val
345                 350                 355                 360

Ala Gly Gln Pro Gln Lys Gly Asn Pro Gly Leu Ser Pro Gln Ala Tyr
                365                 370                 375

Ala Gln Asn Ala Leu Gln Phe Ile Lys Ala Met Arg Ala Glu Asp Pro
            380                 385                 390

Ser Ile Lys Ile Gly Ala Val Leu Thr Met Pro Tyr Asn Trp Pro Trp
        395                 400                 405

Gly Ala Thr Val Asn Gly Asn Asp Asp Trp Asn Thr Val Val Leu Lys
    410                 415                 420

Ala Leu Gly Pro Tyr Ile Asp Phe Val Asp Val His Trp Tyr Pro Glu
425                 430                 435                 440

Thr Pro Gly Gln Glu Thr Asp Ala Gly Leu Leu Ala Asp Thr Asp Gln
                445                 450                 455

Ile Pro Ala Met Val Ala Glu Leu Lys Arg Glu Val Asn Thr Tyr Ala
            460                 465                 470

Gly Ser Asn Ala Lys Asn Ile Gln Ile Phe Val Thr Glu Thr Asn Ser
        475                 480                 485

Val Ser Tyr Asn Pro Gly Glu Gln Ser Thr Asn Leu Pro Glu Ala Leu
    490                 495                 500

Phe Leu Ala Asp Asp Leu Thr Gly Phe Ile Gln Ala Gly Ala Ala Asn
505                 510                 515                 520

Val Asp Trp Trp Asp Leu Phe Asn Gly Ala Glu Asp Asn Tyr Thr Ser
                525                 530                 535

Pro Ser Leu Tyr Gly Gln Asn Leu Phe Gly Asp Tyr Gly Leu Leu Ser
            540                 545                 550

Ser Gly Gln Thr Thr Gln Asn Gly Trp Gln Pro Pro Ala Asn Thr
        555                 560                 565

Pro Leu Pro Pro Tyr Asn Gly Phe Gln Leu Val Ser Asp Phe Ala Gln
    570                 575                 580

Pro Gly Asp Thr Met Leu Gly Ser Thr Thr Ser Gln Ser Ala Ile Asp
585                 590                 595                 600

Val His Ala Val Arg Lys Pro Asn Gly Asp Ile Ser Leu Met Leu Val
                605                 610                 615

Asn Arg Ser Pro Ser Ala Ile Tyr Ser Ala Asn Leu Asn Val Leu Gly
            620                 625                 630

Phe Gly Pro Phe Val Val Thr His Ala Leu Ala Tyr Gly Glu Gly Ser
        635                 640                 645

Ser Arg Val Ala Pro Met Pro Val Leu Pro Val Pro Gly Ala Pro Ile
650                 655                 660

Lys Leu Met Pro Tyr Ser Gly Ile Asp Leu Thr Leu His Pro Leu Ile
665                 670                 675                 680

Pro Ala Pro His Ala Ala Gln Val Thr Asp Thr Leu Thr Leu Ser
                685                 690                 695

Ser Pro Thr Val Thr Ala Gly Gly Ala Glu Thr Leu Ser Ala Ser Phe
            700                 705                 710

Gln Ala Asp Arg Pro Val His His Ala Thr Val Glu Leu Glu Leu Tyr
        715                 720                 725

Asp Ser Thr Asn Asp Leu Val Ala Thr His Thr Val Ser Asp Val Asp
    730                 735                 740
```

Leu Gln Pro Gly Ser Ala Thr Ser Glu Thr Trp Ser Phe Thr Ala Pro
745                 750                 755                 760

Ala Ala Asn Gly Asn Tyr Arg Val Glu Ala Phe Val Phe Asp Pro Val
            765                 770                 775

Thr Gly Ala Thr Tyr Asp Ala Asp Thr Gln Gly Ala Val Leu Thr Val
            780                 785                 790

Asn Gln Pro Pro Gln Ala Thr Tyr Gly Asp Ile Val Thr Lys Asp Thr
        795                 800                 805

Val Ile Thr Val Asn Gly Thr Thr Tyr Asp Val Pro Ala Pro Asp Ala
    810                 815                 820

Gly Gly His Tyr Pro Ser Gly Thr Asn Ile Ser Val Ala Pro Gly Asp
825                 830                 835                 840

Thr Val Thr Val Gln Thr Thr Phe Val Asn Val Ser Ser Thr Asp Ala
            845                 850                 855

Leu Gln Asn Gly Leu Ile Asp Met Glu Val Asp Gly Ser Asn Gly Ala
            860                 865                 870

Ile Leu Gln Lys Tyr Trp Pro Ser Thr Thr Leu Leu Pro Gly Gln Ser
        875                 880                 885

Glu Thr Val Thr Ala Thr Trp Gln Val Pro Ala Asn Val Ala Ala Gly
    890                 895                 900

Thr Tyr Pro Leu Asn Phe Gln Ala Phe Asn Thr Ser Ser Trp Thr Gly
905                 910                 915                 920

Asn Cys Tyr Phe Thr Asn Gly Gly Val Val Asn Phe Val Ile Ser
            925                 930                 935

<210> SEQ ID NO 27
<211> LENGTH: 272
<212> TYPE: PRT
<213> ORGANISM: Alicyclobacillus sp.
<220> FEATURE:
<221> NAME/KEY: SIGNAL
<222> LOCATION: (1)..(32)
<220> FEATURE:
<221> NAME/KEY: mat_peptide
<222> LOCATION: (33)..(272)
<223> OTHER INFORMATION: aspartyl protease

<400> SEQUENCE: 27

Met Asn Gly Thr Ser Val Trp Lys Ala Ser Gly Ile Ala Ala Ser
        -30                 -25                 -20

Cys Leu Thr Ala Ala Ala Leu Leu Ala Trp Pro His Ala Thr Ser Thr
    -15                 -10                  -5                  -1

Leu Asp Ala Ser Pro Ala Ile Phe His Ala Pro Arg His Ala Leu Ser
1                   5                  10                  15

Pro Asn Thr Ser Pro Lys Pro Asn Ser Val Gln Ala Gln Asn Phe Gly
            20                  25                  30

Trp Ser Ala Ser Asn Trp Ser Gly Tyr Ala Val Thr Gly Ser Thr Tyr
            35                  40                  45

Asn Asp Ile Thr Gly Ser Trp Ile Val Pro Ala Val Ser Pro Ser Lys
        50                  55                  60

Arg Ser Thr Tyr Ser Ser Ser Trp Ile Gly Ile Asp Gly Phe Asn Asn
65                  70                  75                  80

Ser Asp Leu Ile Gln Thr Gly Thr Glu Gln Asp Tyr Val Asn Gly His
            85                  90                  95

Ala Gln Tyr Asp Ala Trp Trp Glu Ile Leu Pro Ala Pro Glu Thr Val
            100                 105                 110

Ile Ser Asn Met Thr Ile Ala Pro Gly Asp Arg Met Ser Ala His Ile
            115                 120                 125

His Asn Asn Gly Asn Gly Thr Trp Thr Ile Thr Leu Thr Asp Val Thr
    130                 135                 140

Arg Asn Glu Thr Phe Ser Thr Thr Gln Ser Tyr Ser Gly Pro Gly Ser
145                 150                 155                 160

Ser Ala Glu Trp Ile Gln Glu Ala Pro Glu Ile Gly Gly Arg Ile Ala
                165                 170                 175

Thr Leu Ala Asn Tyr Gly Glu Thr Thr Phe Asp Pro Gly Thr Val Asn
                180                 185                 190

Gly Gly Asn Pro Gly Phe Thr Leu Ser Asp Ala Gly Tyr Met Val Gln
            195                 200                 205

Asn Asn Ala Val Val Ser Val Pro Ser Ala Pro Asp Ser Asp Thr Asp
    210                 215                 220

Gly Phe Asn Val Ala Tyr Gly Ser Asn Gln Pro Ser Pro Pro Ala Ser
225                 230                 235                 240

<210> SEQ ID NO 28
<211> LENGTH: 315
<212> TYPE: PRT
<213> ORGANISM: Alicyclobacillus sp.
<220> FEATURE:
<221> NAME/KEY: SIGNAL
<222> LOCATION: (1)..(25)
<220> FEATURE:
<221> NAME/KEY: mat_peptide
<222> LOCATION: (26)..(315)
<223> OTHER INFORMATION: multi copper oxidase

<400> SEQUENCE: 28

Met Arg Arg Met Ser Gly Phe Ala Thr Gly Leu Gly Ile Ala Ala
-25                 -20                 -15                 -10

Gly Leu Ala Leu Ser Ser Ala Leu Ala Ala Pro Phe Phe His Ala Gly
            -5              -1   1               5

Asn Ala Ser Ala Ala Ser Thr Met Ser Met Ala Pro Thr Ser Thr Met
            10                  15                  20

Gly Ala Leu Pro Ala Pro Glu Gly Val Pro Asp Ala Gly Pro Leu Ser
            25                  30                  35

Ile Thr Pro Glu Val Ile Arg Gln Gln Gln Ala Asp Ala Val Arg Val
40                  45                  50                  55

Met Asp Glu Glu Gly Leu Lys Pro Gln Ile Leu Ser Gly Asp Ile Lys
                60                  65                  70

Arg Phe Thr Leu Thr Ala Ser Gln Val Asn Trp Tyr Leu Tyr Pro Gly
            75                  80                  85

Lys Ala Val Val Ala Cys Gly Tyr Asn Gly Gln Val Pro Gly Pro Val
                90                  95                  100

Leu Arg Val Arg Val Gly Asp Arg Val Gln Ile Leu Leu Arg Asn Glu
            105                 110                 115

Leu Asn Glu Pro Thr Thr Leu His Ile Gln Gly Leu Asp Leu Pro Ala
120                 125                 130                 135

Ser Gln Leu Gly Ile Gly Asp Val Thr Glu Ser Pro Ile Pro Pro Gly
                140                 145                 150

Gly Glu Arg Leu Tyr Ser Phe Thr Val Thr Pro Gln Met Val Gly Thr
            155                 160                 165

His Leu Tyr Glu Ser Gly Thr Asp Met Ala Ser Glu Ile Asp Pro Arg
            170                 175                 180

Thr Ala Arg Gly Ala Ala Arg Arg Ser Gly Pro Gly Ile Pro Leu Ser
            185                 190                 195

Pro Gly Glu Gly Gly Arg Ala Leu Arg Asp Arg Arg Val Asp Gly Gly

```
                     200                 205                 210                 215
Arg Ile Asp His Arg Lys Arg Val Trp Pro Gly Arg Gln Ala Val Ser
                    220                 225                 230

Arg Arg Ala Arg Thr Asp Gly Ala Val Arg Gln Pro Arg Gly Ala Ala
                    235                 240                 245

His Arg Gln Arg Glu Arg Asp Val Leu Pro Arg His Ala Pro Ala Arg
                    250                 255                 260

Asp Asp Val Leu Ala Ala Gly Gly Arg Arg Ala Pro Pro Arg Gln Ala
                    265                 270                 275

Ala Ala Asp Glu Arg Ala Arg His Arg Ala Arg
280                 285                 290

<210> SEQ ID NO 29
<211> LENGTH: 626
<212> TYPE: PRT
<213> ORGANISM: Alicyclobacillus sp.
<220> FEATURE:
<221> NAME/KEY: SIGNAL
<222> LOCATION: (1)..(32)
<220> FEATURE:
<221> NAME/KEY: PROPEP
<222> LOCATION: (33)..(189)
<220> FEATURE:
<221> NAME/KEY: mat_peptide
<222> LOCATION: (190)..(626)
<223> OTHER INFORMATION: serine-carboxyl protease

<400> SEQUENCE: 29

Met Gly Leu Trp Lys Arg Leu Ala Leu Gly Val Pro Ala Ala Leu
                -185                -180                -175

Ser Met Leu Ala Val Gly Val Pro Val Met Ser Ala Asp Thr Val
                -170                -165                -160

Glu Ala Ala Pro Leu Ala Asn Pro Ser Thr Glu Asn Ala Gln Asp
                -155                -150                -145

Met Gly Pro Ala Ser Gly Ser Gln Thr Val Thr Ala Ser Ile Ile
                -140                -135                -130

Leu Arg Val Gln Asn Pro Thr Ala Leu Gln Asn Tyr Ile Gln Glu
                -125                -120                -115

Thr Glu Thr Pro Gly Ser Pro Leu Tyr His Lys Phe Leu Thr Thr
                -110                -105                -100

Ala Gln Phe Ala Gln Gln Tyr Ala Pro Ser Ala Ala Thr Leu Gln Gln
                    -95                 -90                 -85

Ile Glu Gln Glu Leu Gln Gly Tyr Gly Leu Gln Val Val Asn Val Asp
                    -80                 -75                 -70

Ala Asp His Leu Asp Met Gln Val Gly Thr Val Gln Gln Phe Asp
        -65                 -60                 -55

Asn Ala Phe Asn Thr Val Ile Asp Leu Phe Lys Ala Asn Gly His Ile
    -50                 -45                 -40

Phe Arg Ala Pro Lys Lys Pro Pro Gln Ile Pro Val Ala Leu Leu Thr
-35                 -30                 -25                 -20

Asn Val Leu Ala Val Val Gly Leu Asp Thr Ala Gln Ala Ala Gln Ser
                    -15                 -10                 -5

Leu Thr Val Lys Thr Pro Asn Val Ala Gly Val Pro Ser Pro Lys Val
        -1  1                   5                  10

Val Leu Pro Gln Gly Gly Ser Thr Ala Thr Gly Thr Pro Gly Ser Tyr
            15                  20                  25

Thr Val Gly Asp Thr Ala Asn Arg Tyr Asp Ile Asn Pro Leu Tyr Gln
30                  35                  40                  45
```

```
Lys Gly Ile Thr Gly Lys Gly Glu Thr Ile Gly Ile Val Thr Leu Ser
                 50                   55                  60

Ser Phe Asn Pro Gln Asp Ala Tyr Thr Tyr Trp Gln Gly Ile Gly Leu
                65                  70                  75

Lys Val Ala Pro Asn Arg Ile Gln Met Val Asn Val Asp Gly Gly
            80                  85                  90

Gln Met Asp Asp Gly Ser Val Glu Thr Thr Leu Asp Val Glu Gln Ser
         95                 100                 105

Gly Gly Leu Ala Pro Asp Ala Asn Val Val Tyr Asp Ala Pro Asn
110             115                 120                 125

Thr Asp Gln Gly Phe Ile Asp Ala Phe Tyr Gln Ala Val Ser Asp Asn
                130                 135                 140

Gln Ala Asp Ser Leu Ser Val Ser Trp Gly Gln Pro Glu Ile Asp Tyr
            145                 150                 155

Leu Pro Gln Met Asn Gln Gly Gln Ser Tyr Val Asp Glu Leu Leu Ala
                160                 165                 170

Phe Thr Gln Ala Phe Met Glu Ala Ala Gln Gly Ile Ser Met Tyr
    175                 180                 185

Ala Ala Ala Gly Asp Ser Gly Ala Tyr Asp Thr Ala Arg Asp Phe Pro
190                 195                 200                 205

Pro Ser Asp Gly Phe Thr Thr Pro Leu Ser Val Asp Phe Pro Ala Ser
                210                 215                 220

Asp Pro Tyr Ile Thr Ala Ala Gly Gly Thr Thr Val Pro Phe Thr Ala
            225                 230                 235

Lys Phe Ser Leu Gly Thr Val Asn Ile Thr Gln Glu Gln Pro Trp Ser
    240                 245                 250

Trp Gln Tyr Leu Gln Asn Leu Gly Tyr Gln Gly Leu Phe Ser Val Gly
    255                 260                 265

Thr Gly Gly Gly Val Ser Val Ile Phe Pro Arg Pro Trp Tyr Gln Leu
270                 275                 280                 285

Gly Val Gly Gly Met Gln Asn Ser Ala Ala Asn Gln Ala Phe Thr Asp
                290                 295                 300

Ser Gln Gly Val Leu Tyr Gly Ser Pro Phe Thr Tyr Asn Leu Pro Ser
            305                 310                 315

Asn Tyr Ala Gly Arg Asn Leu Pro Asp Ile Ser Met Asp Ala Asp Pro
    320                 325                 330

Glu Thr Gly Tyr Leu Val Tyr Trp Ser Ala Gly Gly Trp Ile Ala
    335                 340                 345

Gly Tyr Gly Gly Thr Ser Phe Val Ala Pro Gln Leu Asn Gly Ile Thr
350                 355                 360                 365

Ala Leu Ile Asp Gln Glu Val His Gly Arg Val Gly Phe Leu Asn Pro
                370                 375                 380

Leu Leu Tyr Thr Leu Thr Gln Gly Val Gln Gly Ala Gln Pro
            385                 390                 395

Phe His Asp Ile Thr Thr Gly Asn Asn Trp Tyr Trp Asn Ala Val Pro
        400                 405                 410

Gly Tyr Asp Pro Ala Ser Gly Val Gly Thr Pro Asp Val Ala Asn Leu
    415                 420                 425

Ala Gln Asp Ile Ala Ser Leu Arg
430                 435

<210> SEQ ID NO 30
<211> LENGTH: 533
<212> TYPE: PRT
<213> ORGANISM: Alicyclobacillus sp.
```

```
<220> FEATURE:
<221> NAME/KEY: SIGNAL
<222> LOCATION: (1)..(24)
<220> FEATURE:
<221> NAME/KEY: mat_peptide
<222> LOCATION: (25)..(534)
<223> OTHER INFORMATION: serine-carboxyl protease

<400> SEQUENCE: 30
```

Met Arg Ala Leu Ala His Leu Ala Ile Gly Ala Ile Ala Ser Gly Val
         -20                 -15                 -10

Phe Ala Ala Pro Val Ala Phe Ala Ser Pro Val Gln Glu Arg Val Val
         -5              -1   1               5

Val Ala Ser Pro Asp Pro Arg Thr Arg Ser Val His Ala Asp Gly Glu
         10              15               20

Ile Ser Pro Ser Gln Pro Met His Leu Val Ile Thr Leu Arg Leu Arg
 25                  30              35                   40

His Glu Ala Gln Leu Glu Gln Leu Ile Arg Asp Leu Tyr Thr Pro Gly
             45              50                  55

Ser Pro Asp Ala Gly His Phe Leu Thr Pro Ala Ala Phe Asn Ala Ala
             60              65                  70

Tyr Ala Pro Thr Ala Glu Asp Val Gln Ala Val Val Gln Gly Leu Arg
             75              80                  85

Ala Tyr Gly Leu Arg Val Glu Pro Thr Val Asn Pro Met Val Leu Thr
     90              95                  100

Val Ser Gly Arg Ala Arg Asp Val Glu Arg Ala Phe Gly Val His Glu
 105             110                  115                 120

Leu Gln Phe Gly Arg Gly Ala Gly Ala Trp Tyr Ala Pro Asp Gly Ala
                 125             130                  135

Ala Thr Leu Pro Ala Pro Leu Ala Ala Arg Val Ser Ala Val Val Gly
                 140              145                 150

Leu Thr Ser Asp Ala Met Glu Arg His Leu Val Leu Ala His Val Ala
             155             160                  165

Pro Ala Gly Gly Gly Tyr Thr Pro Ala Gln Ile Gln Arg Ala Tyr Asp
 170                 175                  180

Tyr Thr Pro Leu Tyr Ser Gln Tyr Met Gly Arg Gly Gln Val Ile Ala
 185                 190                  195                 200

Val Val Thr Ser Gly Ser Val Leu Arg Ser Asp Leu Leu Ala Phe Asp
                 205             210                  215

Arg Ala Phe Gly Leu Pro Asn Pro Val Val Arg Gln Arg Val Ile Asp
                 220             225                  230

Gly Ser Ser Thr Ser Pro Asp Asp Glu Thr Thr Leu Asp Cys Glu Trp
             235             240                  245

Ala His Ala Ile Ala Pro Thr Ala Ser Leu Ala Val Tyr Glu Ala Ala
     250                 255                  260

Gln Pro Asp Ala Gln Ser Phe Ile Asp Ala Phe Ala Gln Val Ala Ala
 265             270                  275                  280

Asp Asp Gly Ala His Val Val Thr Thr Ser Trp Gly Ala Pro Glu Ser
                 285             290                  295

Glu Thr Asp Ala Ala Thr Met Gln Ala Glu His Gln Ile Phe Met Gln
                 300             305                  310

Met Ala Ala Gln Gly Gln Ser Val Phe Ala Ala Gly Asp Ser Gly
                 315             320                  325

Ser Ser Asp Gly Thr Ser Gly Thr Asp Val Asp Tyr Pro Ser Ser Asp
 330                 335                  340

Pro Tyr Val Thr Ala Cys Gly Gly Thr Arg Leu Val Leu Gly Ala Gly

```
                345                 350                 355                 360
Ala Lys Arg Leu Gln Glu Thr Ala Trp Ala Asp Thr Gly Gly Gly Ala
                    365                 370                 375

Ser Ser Val Tyr Gly Glu Pro Trp Trp Gln Tyr Gly Pro Gly Val Pro
                    380                 385                 390

Gln Thr Gly Tyr Arg Gln Thr Cys Asp Val Ala Leu Asn Ala Asp Pro
                    395                 400                 405

Ala Thr Gly Tyr Asp Phe Ile Tyr Glu Gly Gln Trp Glu Val Ala Gly
            410                 415                 420

Gly Thr Ser Phe Val Ala Pro Met Met Ala Ala Thr Phe Ala Leu Ile
425                 430                 435                 440

Asp Gln Ala Arg Ala Leu Glu Gly Lys Pro Pro Val Gly Leu Ala Asp
                    445                 450                 455

Val Gly Ile Tyr Ala Met Ala Arg Asn Ala Ser Tyr Ala Pro Tyr Ala
            460                 465                 470

Phe His Asp Ile Thr Ala Gly Ser Asn Gly Ala Tyr Ser Ala Gly Pro
            475                 480                 485

Gly Trp Asp His Pro Thr Gly Phe Gly Ser Ile Asp Ala Tyr Tyr Phe
490                 495                 500

Leu His Gly Leu Asp
505

<210> SEQ ID NO 31
<211> LENGTH: 360
<212> TYPE: PRT
<213> ORGANISM: Alicyclobacillus sp.
<220> FEATURE:
<221> NAME/KEY: SIGNAL
<222> LOCATION: (1)..(41)
<220> FEATURE:
<221> NAME/KEY: mat_peptide
<222> LOCATION: (42)..(411)
<223> OTHER INFORMATION: protease or a HtrA-like serine protease

<400> SEQUENCE: 31

Met Arg Arg Arg Arg Trp Asp Tyr Glu Asp Trp Pro Ser Glu Asn Arg
    -40                 -35                 -30

Arg Val Gly Val Trp Leu Ala Ser Gly Thr Ala Leu Leu Ala Ile Cys
-25                 -20                 -15                 -10

Tyr Ile Leu Gly Ile Trp Thr Gly Ala Ala Leu Thr Arg Gly His Ser
                -5                  -1  1               5

Gln Thr Thr Val Glu Tyr Val Pro Pro Gln Thr Gly Asn Thr Ala Ser
            10                  15                  20

Thr Ser Gly Ser Leu Thr Pro Ile Pro Gly Val Glu Asp Thr Thr Ile
        25                  30                  35

Val Thr Gln Ile Tyr Asn Arg Val Lys Asn Ser Ile Phe Thr Ile Thr
40                  45                  50                  55

Ala Val Ser Gly Gly Lys Pro Thr Ser Ser Asp Ala Glu Glu Asp Ile
                    60                  65                  70

Gly Thr Gly Phe Leu Ile Asp His Asn Gly Asp Leu Leu Thr Asn Ala
            75                  80                  85

His Val Val Gly Ser Ala Thr Thr Val Gln Val Ser Gly Asp Asn Arg
        90                  95                  100

Gln Phe Val Gly Arg Val Ile Asp Ala Asp Gln Leu Asp Asp Leu Ala
        105                 110                 115

Ile Val Arg Ile Pro Ala Pro Lys Ser Leu Glu Pro Leu Pro Leu Gly
120                 125                 130                 135
```

```
Ser Val Lys Ser Leu Gln Pro Gly Ser Leu Ile Ala Ile Gly Asn
            140                 145                 150

Pro Phe Glu Leu Thr Ser Ser Val Ser Ser Gly Ile Val Ser Gly Leu
                155                 160                 165

Asn Arg Ser Met Ser Glu Ser Asn Gly His Val Met Asn Gly Met Ile
            170                 175                 180

Gln Thr Asp Ala Pro Leu Asn Pro Gly Asn Ser Gly Gly Pro Leu Leu
        185                 190                 195

Asn Ala Ala Gly Gln Val Val Gly Ile Asn Thr Leu Ile Glu Ser Pro
200                 205                 210                 215

Ile Glu Gly Ser Ile Gly Ile Gly Phe Ala Ile Pro Ile Asp Arg Phe
                220                 225                 230

Ile Gln Leu Glu Pro Glu Leu Leu Ala Gly Lys Pro Val Ala His Ala
            235                 240                 245

Trp Leu Gly Ile Glu Gly Met Asp Ile Asp Asn Leu Met Arg Gln Ala
        250                 255                 260

Leu His Leu Pro Val Ala Ser Gly Val Tyr Val Thr Glu Val Thr Pro
    265                 270                 275

Gly Gly Pro Ala Ala Lys Ala Gly Leu Arg Gly Asp Ser Asn Ala Ala
280                 285                 290                 295

Lys Leu Asn Ser Leu Ser Gln Ser Ala Asn Pro Tyr Ala Leu Leu Lys
                300                 305                 310

Gly Asn Gly Asp Ile Ile Val Gly
            315

<210> SEQ ID NO 32
<211> LENGTH: 211
<212> TYPE: PRT
<213> ORGANISM: Alicyclobacillus sp.
<220> FEATURE:
<221> NAME/KEY: SIGNAL
<222> LOCATION: (1)..(30)
<220> FEATURE:
<221> NAME/KEY: mat_peptide
<222> LOCATION: (31)..(212)
<223> OTHER INFORMATION: disulfide isomerase

<400> SEQUENCE: 32

Met Arg Arg Ser Trp Ser Val Leu Met Ala Val Cys Met Ser Trp Leu
-30                 -25                 -20                 -15

Ala Val Gly Cys Gly Thr Pro Ala Asn Ser Leu Ser Gln Ala Thr Ala
            -10                 -5                  -1   1

Ala Ser Gly Arg His Ala Pro His Pro Leu Val Phe Gln Asn Leu Thr
        5                   10                  15

Gly Ala Met Asn Glu Gly Gln Asp Pro Arg Trp Asp Pro Lys Ala Ala
    20                  25                  30

Pro Thr Gly Val Tyr Asp Asp Val Thr Val Thr Ala Ser Gly Arg
35                  40                  45                  50

Gln Glu Val Leu Ser Val Arg Asp Ala Pro Leu Leu Phe Ala Ala Tyr
                55                  60                  65

Trp Cys Pro His Cys Gln Arg Thr Leu Gln Leu Leu Thr Ser Ile Glu
            70                  75                  80

Ser Arg Leu Lys Gln Lys Pro Ile Leu Val Asn Val Gly Tyr Pro Pro
        85                  90                  95

Gly Thr Thr Leu Gln Thr Ala Ala Arg Ile Ala Arg Glu Glu Ser Gln
    100                 105                 110

Val Leu His Leu Ala Pro Phe Gln Glu Val Phe Ile Leu Asn Pro Asp
115                 120                 125                 130
```

```
Ala Gly Asp Arg Tyr Ala Pro Leu Gly Tyr Pro Thr Leu Ala Phe Tyr
            135                 140                 145

Arg Ala Gly Arg Asp Trp Thr Leu Tyr Gly Glu His Arg Ala Ser Ile
            150                 155                 160

Trp Glu Lys Ala Leu Ser Glu Ser Thr Ser Lys Ala Tyr Asn Gly Ser
            165                 170                 175

Glu Glu Ser
    180

<210> SEQ ID NO 33
<211> LENGTH: 266
<212> TYPE: PRT
<213> ORGANISM: Alicyclobacillus sp.
<220> FEATURE:
<221> NAME/KEY: SIGNAL
<222> LOCATION: (1)..(29)
<220> FEATURE:
<221> NAME/KEY: mat_peptide
<222> LOCATION: (30)..(266)
<223> OTHER INFORMATION: gamma-D-glutamyl-L-diamino acid endopeptidase

<400> SEQUENCE: 33

Met Asp Glu Met Asn Ile Arg Ser Trp Cys Val Ala Ala Cys Thr Val
            -25                 -20                 -15

Ala Leu Thr Ser Ala Val Gly Ala Thr Thr Ala Phe Ala Gln Thr Val
            -10                  -5                  -1   1

Thr Val Gln Pro Gly Gln Ser Leu Trp Thr Ile Ala Arg Ala His Gly
      5                  10                  15

Met Pro Val Gln Leu Val Ala Ser Ala Asn Pro Gln Tyr Asn Pro Leu
 20                  25                  30                  35

Asn Leu Pro Val Gly Ala Thr Val Thr Leu Pro Ser Leu Lys Asp Val
                 40                  45                  50

Ala Val Gln Pro Gly Asp Ser Leu Phe Leu Ile Gly Arg Gln Tyr Gly
             55                  60                  65

Val Ser Leu Ala Glu Met Leu Ala Ala Asn Pro Asn Val Asp Pro Leu
             70                  75                  80

Asn Leu Gln Val Gly Ser Ser Val Arg Val Pro Leu Ala Ser Ser Ser
 85                  90                  95

Thr Lys Ser Ser Thr Val Ser Ala His Val Ala Ala Ser Thr Pro Glu
100                 105                 110                 115

Asn Ser Asn Asn Leu Tyr Trp Leu Glu Arg Val Ile His Ala Glu Ala
            120                 125                 130

Gly Gly Glu Ser Leu Gln Ala Gln Ile Ala Val Ala Asp Val Ile Leu
            135                 140                 145

His Arg Met Ala Ala Gly Gly Tyr Gly Ser Thr Val Gln Gln Val Val
            150                 155                 160

Phe Gln Val Ser Asp Gly His Tyr Gln Phe Glu Ser Val Ala Asn Gly
            165                 170                 175

Ser Ile Tyr Gly Gln Pro Asp Ala Gln Asn Val Gln Ala Ala Leu Asp
180                 185                 190                 195

Ala Leu Asn Gly Asp Asp Val Val Pro Gly Ala Leu Val Phe Tyr Asn
                200                 205                 210

Pro Ala Gln Thr Pro Ser Gly Ser Trp Val Trp Gln Pro Val Val
            215                 220                 225

Ala His Ile Gly His Leu Val Phe Ala Lys
            230                 235
```

```
<210> SEQ ID NO 34
<211> LENGTH: 768
<212> TYPE: PRT
<213> ORGANISM: Alicyclobacillus sp.
<220> FEATURE:
<221> NAME/KEY: SIGNAL
<222> LOCATION: (1)..(26)
<220> FEATURE:
<221> NAME/KEY: mat_peptide
<222> LOCATION: (27)..(768)
<223> OTHER INFORMATION: endo-beta-N-acetylglucosaminidase

<400> SEQUENCE: 34
```

| Met | Lys | Thr | His | Arg | Leu | Leu | Ala | Val | Ala | Ala | Leu | Pro | Ala | Thr | Val |
|---|---|---|---|---|---|---|---|---|---|---|---|---|---|---|---|
| -25 | | | | -20 | | | | | -15 | | | | | | |

| Leu | Leu | Thr | Thr | Pro | Ala | Pro | Ala | Leu | Ala | Glu | Thr | Ser | Ser | Ser | Gln |
|---|---|---|---|---|---|---|---|---|---|---|---|---|---|---|---|
| -10 | | | | -5 | | | | | -1 | 1 | | | | 5 | |

| Ser | Ala | Ser | Ala | Pro | Ser | Leu | Asn | Val | Pro | Val | Ala | Ala | Leu | Thr | Leu |
|---|---|---|---|---|---|---|---|---|---|---|---|---|---|---|---|
| | | | 10 | | | | | 15 | | | | | 20 | | |

| Ala | Gly | Val | Gln | Ser | Tyr | Pro | Met | Leu | Ser | Tyr | Gly | Ser | Thr | Gly | Val |
|---|---|---|---|---|---|---|---|---|---|---|---|---|---|---|---|
| | | | | 25 | | | | | 30 | | | | | 35 | |

| Tyr | Val | Glu | Ile | Leu | Gln | Asn | Ala | Leu | Asn | Ala | Leu | Gly | Tyr | Asp | Val |
|---|---|---|---|---|---|---|---|---|---|---|---|---|---|---|---|
| | 40 | | | | | 45 | | | | | 50 | | | | |

| Gly | Gln | Ala | Ser | Gly | Leu | Phe | Asp | Ala | Thr | Thr | Gln | Ala | Glu | Val | Lys |
|---|---|---|---|---|---|---|---|---|---|---|---|---|---|---|---|
| 55 | | | | | 60 | | | | | 65 | | | | | 70 |

| Ala | Phe | Gln | Gln | Ala | Met | Gly | Leu | Gln | Thr | Asp | Gly | Ile | Val | Gly | Pro |
|---|---|---|---|---|---|---|---|---|---|---|---|---|---|---|---|
| | | | | 75 | | | | | 80 | | | | | 85 | |

| Leu | Thr | Trp | Gly | Ala | Leu | Ala | Lys | Ala | Val | Ala | Asp | Tyr | Arg | Gln | Val |
|---|---|---|---|---|---|---|---|---|---|---|---|---|---|---|---|
| | | | 90 | | | | | 95 | | | | | 100 | | |

| Met | Thr | Val | Leu | Ser | Ser | Arg | Ser | Ser | Leu | Val | Gln | Gln | Val | Glu | Trp |
|---|---|---|---|---|---|---|---|---|---|---|---|---|---|---|---|
| | | 105 | | | | | 110 | | | | | 115 | | | |

| Lys | Arg | Ile | Val | Trp | Asn | Gly | Arg | Leu | Ile | Ser | Lys | Pro | Ile | Gly | Phe |
|---|---|---|---|---|---|---|---|---|---|---|---|---|---|---|---|
| | 120 | | | | | 125 | | | | | 130 | | | | |

| Thr | Tyr | Gln | Gly | Thr | Ala | Tyr | Met | Pro | Ile | Trp | Tyr | Val | Met | Gln | Ala |
|---|---|---|---|---|---|---|---|---|---|---|---|---|---|---|---|
| 135 | | | | | 140 | | | | | 145 | | | | | 150 |

| Leu | Ser | Lys | Ala | Gly | Ile | Ala | Ser | Thr | Trp | Gln | Gly | Gly | Val | Trp | Thr |
|---|---|---|---|---|---|---|---|---|---|---|---|---|---|---|---|
| | | | | 155 | | | | | 160 | | | | | 165 | |

| Leu | Thr | Pro | Pro | Gly | Gly | Gln | Thr | Val | Asn | Tyr | Gly | Lys | Ile | Ser | Tyr |
|---|---|---|---|---|---|---|---|---|---|---|---|---|---|---|---|
| | | | 170 | | | | | 175 | | | | | 180 | | |

| Gly | Pro | Gly | Ser | Ala | Ala | Ile | Ala | Ile | Gly | Gln | Thr | Val | Val | Ala | Asn |
|---|---|---|---|---|---|---|---|---|---|---|---|---|---|---|---|
| | | 185 | | | | | 190 | | | | | 195 | | | |

| Val | Pro | Ala | Val | Val | Tyr | Pro | Asp | Pro | Ala | Ser | Gly | Lys | Leu | Thr | Thr |
|---|---|---|---|---|---|---|---|---|---|---|---|---|---|---|---|
| | 200 | | | | | 205 | | | | | 210 | | | | |

| Phe | Met | Pro | Val | Trp | Tyr | Val | Met | Asn | Ala | Leu | Gln | Arg | Leu | Gly | Ile |
|---|---|---|---|---|---|---|---|---|---|---|---|---|---|---|---|
| 215 | | | | | 220 | | | | | 225 | | | | | 230 |

| Gly | Ser | Thr | Trp | Gln | Gly | Thr | Glu | Trp | Asp | Met | Lys | Pro | Ala | Pro | Val |
|---|---|---|---|---|---|---|---|---|---|---|---|---|---|---|---|
| | | | | 235 | | | | | 240 | | | | | 245 | |

| Val | Ile | Glu | Thr | Gly | Asp | Pro | Ser | Asn | Asn | Thr | Gly | Ser | Asp | Pro |
|---|---|---|---|---|---|---|---|---|---|---|---|---|---|---|
| | | | 250 | | | | | 255 | | | | | 260 | |

| Ala | Asn | Ser | Thr | Gly | Asn | Gly | Thr | Gly | Asn | Ser | Thr | Gly | Asn | Ala | Thr |
|---|---|---|---|---|---|---|---|---|---|---|---|---|---|---|---|
| | | | 265 | | | | | 270 | | | | | 275 | | |

| Gly | Ala | Val | Pro | Gly | Gly | Asn | Thr | Val | Thr | Asn | Val | Thr | Thr | Gly | Ser |
|---|---|---|---|---|---|---|---|---|---|---|---|---|---|---|---|
| | | 280 | | | | | 285 | | | | | 290 | | | |

| Ser | Asn | Val | Thr | Gly | Asn | Ser | Thr | Gly | Asn | Ser | Leu | Gly | Asn | Ser | Thr |
|---|---|---|---|---|---|---|---|---|---|---|---|---|---|---|---|
| 295 | | | | | 300 | | | | | 305 | | | | | 310 |

| Gly | Asn | Ser | Leu | Gly | Asn | Ser | Thr | Ser | Asn | Ala | Thr | Gly | Asn | Ala | Thr |
|---|---|---|---|---|---|---|---|---|---|---|---|---|---|---|---|
| | | | | 315 | | | | | 320 | | | | | 325 | |

-continued

Gly Asn Thr Thr Gly Asn Ala Thr Gly Asn Ser Thr Gly Thr Ser Ser
             330                 335                 340

Gly Ser Phe Thr Asn Val Asp Leu Arg Tyr Pro Ala Pro Ser Asn Ile
         345                 350                 355

Asn Ala Gln Ser Ile Asn Gln Phe Leu Leu Gln Asn Ser Ser Pro Leu
     360                 365                 370

Asn Gly Leu Gly Asn Ser Phe Met Asp Ala Gln Asn Leu Tyr Ser Val
375                 380                 385                 390

Asp Ala Asn Tyr Leu Val Ser His Ala Ile Leu Glu Ser Ala Trp Gly
                 395                 400                 405

Gln Ser Gln Ile Ala Leu Gln Lys Asn Asn Leu Phe Gly Tyr Gly Ala
             410                 415                 420

Tyr Asp Ser Asn Pro Gly Gln Asp Ala Gly Val Phe Pro Ser Asp Asp
         425                 430                 435

Tyr Ala Ile Arg Phe Glu Ala Trp Thr Val Arg Met Asn Tyr Leu Thr
     440                 445                 450

Pro Gly Ala Ser Leu Tyr Val Thr Pro Thr Leu Ser Gly Met Asn Val
455                 460                 465                 470

Asn Tyr Ala Thr Ala Lys Thr Trp Ala Ser Gly Ile Ala Ala Ile Met
                 475                 480                 485

Thr Gln Phe Ala Ser Ser Val Gly Ser Asn Val Asn Ala Tyr Val Gln
             490                 495                 500

Tyr Thr Pro Ser Asn Asn Pro Pro Ala Pro Arg Ser Thr Ala Glu Pro
         505                 510                 515

Val Tyr Tyr Met Asn Gly Ala Gln Gly Val Thr Gln Gln Asp Pro Tyr
     520                 525                 530

Tyr Pro Asn Gly Gly Val Pro Tyr Tyr Pro Thr Ile Ala Gln Gly Glu
535                 540                 545                 550

Asn Gln Gln Phe Phe Gly Gln Leu Ser Val Gly Ser Phe Gly Gln Pro
                 555                 560                 565

Val Val Glu Val Gln Gln Phe Leu Asn Arg Thr Ile Asn Ala Gly Leu
             570                 575                 580

Thr Val Asp Gly Gln Phe Gly Pro Leu Thr Gln Ala Ala Val Glu Lys
         585                 590                 595

Phe Gln Ser Gln Val Met His Met Ser Asn Pro Asn Gly Ile Trp Thr
     600                 605                 610

Phe Ser Met Trp Val Gln Tyr Ile Gln Pro Ser Gln Ser Asn Ala Asn
615                 620                 625                 630

Leu Ile Pro Ala Gly Thr Thr Val Lys Ile Asp Gln Val Ala Glu Gly
                 635                 640                 645

Met Ala Gly Pro Tyr Val Val Pro Trp Tyr His Val Val Gly Tyr Gly
             650                 655                 660

Trp Val Asp Ser Gln Tyr Ile Lys Leu Thr Asn Val Tyr Arg Val Ile
         665                 670                 675

Val Gln Asn Pro Ala Gly Thr Ala Thr Thr Ile Pro Val Tyr Gln Val
     680                 685                 690

Gly Asn Leu Ser Ser Val Leu Leu Asn Leu His Ser Gly Asp Trp Val
695                 700                 705                 710

Val Ala Asn Ser Ala Gln Pro Ser Gly Gly Val Tyr Thr Ile Gln Ile
                 715                 720                 725

Ala Ala Gln Asp Pro Pro Cys Arg Thr Ala Thr Pro Pro Gly Arg Ser
             730                 735                 740

<210> SEQ ID NO 35

```
<211> LENGTH: 597
<212> TYPE: PRT
<213> ORGANISM: Alicyclobacillus sp.
<220> FEATURE:
<221> NAME/KEY: SIGNAL
<222> LOCATION: (1)..(49)
<220> FEATURE:
<221> NAME/KEY: mat_peptide
<222> LOCATION: (50)..(597)
<223> OTHER INFORMATION: multi copper oxidase
<220> FEATURE:
<221> NAME/KEY: MISC_FEATURE
<222> LOCATION: (139)..(139)
<223> OTHER INFORMATION: putative copper binding site
<220> FEATURE:
<221> NAME/KEY: MISC_FEATURE
<222> LOCATION: (141)..(141)
<223> OTHER INFORMATION: putative copper binding site
<220> FEATURE:
<221> NAME/KEY: MISC_FEATURE
<222> LOCATION: (181)..(181)
<223> OTHER INFORMATION: putative copper binding site
<220> FEATURE:
<221> NAME/KEY: MISC_FEATURE
<222> LOCATION: (183)..(183)
<223> OTHER INFORMATION: putative copper binding site
<220> FEATURE:
<221> NAME/KEY: MISC_FEATURE
<222> LOCATION: (514)..(514)
<223> OTHER INFORMATION: putative copper binding site
<220> FEATURE:
<221> NAME/KEY: MISC_FEATURE
<222> LOCATION: (566)..(566)
<223> OTHER INFORMATION: putative copper binding site

<400> SEQUENCE: 35

Met Met Ala His Asp Arg Leu Asp Arg Arg Val Asn Glu Arg Arg Gln
            -45                 -40                 -35

Ala Met Arg Arg Ala Ala Lys Trp Ala Ile Ala Leu Gly Thr Thr Ala
        -30                 -25                 -20

Val Val Ala Gly Val Ser Ser Val Phe Ala Leu Arg Ser Val Arg Glu
    -15                 -10                  -5

Ala Asn Leu Asn Pro Asn Ala Pro Leu Ala Asn Val Pro Gly Pro Gln
 -1   1               5                  10                  15

Gly Ala Tyr Thr Pro Ile Ser Ala Leu Gln Pro Val Val Pro Lys Asn
                 20                  25                  30

Ala Arg Ile Asp His Tyr Thr Leu Thr Ala Glu Ser Arg Thr Leu Thr
             35                  40                  45

Val Gly Gly His Ala Leu Gln Ala Met Thr Phe Asn Gly Thr Ala Pro
         50                  55                  60

Gly Pro Leu Leu Val Ala His Gln Gly Asp Val Val Lys Val Thr Val
     65                  70                  75

His Asn Arg Leu Ser Val Pro Leu Thr Ile His Trp His Gly Ile Ala
 80                  85                  90                  95

Val Pro Gly Ala Glu Asp Gly Val Pro Gly Val Thr Gln Asn Pro Ile
                100                 105                 110

Pro Pro Gly Gly Ser Tyr Thr Tyr Glu Phe Gln Val Asn Gln Pro Gly
                115                 120                 125

Thr Tyr Trp Tyr His Ser His Glu Ala Ser Phe Glu Glu Val Gly Leu
            130                 135                 140

Gly Leu Tyr Gly Ala Phe Val Leu Pro Lys Arg Ala Val His Pro
        145                 150                 155

Ala Asp Arg Asp Tyr Thr Leu Val Leu His Glu Trp Pro Thr Ala Ser
160                 165                 170                 175

Thr Ala Gln Thr Met Met Ala Asn Leu Lys Ala Gly Asn Leu Gly Phe
```

```
                        180                 185                 190
Ser Ala Lys Gly Glu Ser Ala Gly Met Gly Gly Met Gly Met Gln Gln
                195                 200                 205

Asn Gly Asp Met Asn Gly Met Gly Met Met Gly Ala Ala Asp Gly Thr
            210                 215                 220

Gly Gln Gly Gly Asn Ser Ala Ser Asp Ile Ala His Val Leu Pro Gly
        225                 230                 235

Pro Pro Leu Gln Leu Asn Gly Phe Ser Pro Thr Ala Asn Asp Trp Ala
240                 245                 250                 255

Ala Leu Asp Glu Met Ala Gly Met Tyr Asp Ala Phe Thr Val Asn Gln
                260                 265                 270

Asn Ala Ser Gly Thr Thr Leu Leu Pro Ala Lys Pro Gly Gln Leu Val
            275                 280                 285

Arg Leu Arg Ile Val Asn Ser Gly Asn Met Thr His Leu Phe Thr Leu
        290                 295                 300

Val Gly Ala Pro Phe Arg Val Val Ala Leu Asp Gly His Asp Ile Ala
    305                 310                 315

Asn Pro Gly Trp Ile Arg Gly Val Leu Leu Pro Val Gly Ala Ala Glu
320                 325                 330                 335

Arg Tyr Asp Ile Glu Phe Arg Val Pro Lys Ser Gly Ala Ala Phe Leu
                340                 345                 350

Val Cys Ala Asp Pro Asp Thr Thr Ala Gln Arg Glu Leu Arg Ala Ala
            355                 360                 365

Ile Gly Leu Pro Asp Ala Trp Ser Gln Phe Lys Glu Thr Asp Ala Ala
        370                 375                 380

Ser Leu Glu Arg Ala Pro Trp Phe Asp Phe Thr His Tyr Gly Ser Gly
    385                 390                 395

Arg Leu Pro Gly Glu Ala Val Phe Arg Leu His Gln Ala Tyr Gln Val
400                 405                 410                 415

Arg Tyr Asn Met Lys Leu Thr Val Gly Met Ser Met Asn Gly Met Val
                420                 425                 430

Tyr Ala Ile Asn Gly Lys Val Phe Pro Asn Ile Pro Pro Ile Val Val
            435                 440                 445

Arg Lys Gly Asp Ala Val Leu Val His Ile Val Asn Asp Ser Pro Tyr
        450                 455                 460

Ile His Pro Met His Leu His Gly His Asp Phe Gln Val Leu Thr Arg
    465                 470                 475

Asp Gly Lys Pro Val Ser Gly Ser Pro Ile Phe Leu Asp Thr Leu Asp
480                 485                 490                 495

Val Phe Pro Gly Glu Ser Tyr Asp Ile Ala Phe Arg Ala Asp Asn Pro
                500                 505                 510

Gly Leu Trp Met Phe His Cys His Asp Leu Glu His Ala Ala Ala Gly
            515                 520                 525

Met Asp Val Met Val Gln Tyr Ala Gly Ile Arg Asp Pro Tyr Pro Met
        530                 535                 540

Ser Glu Met Ser Glu
    545

<210> SEQ ID NO 36
<211> LENGTH: 245
<212> TYPE: PRT
<213> ORGANISM: Alicyclobacillus sp.
<220> FEATURE:
<221> NAME/KEY: SIGNAL
<222> LOCATION: (1)..(29)
<220> FEATURE:
```

```
<221> NAME/KEY: mat_peptide
<222> LOCATION: (30)..(246)
<223> OTHER INFORMATION: peptidyl-prolyl-isomerase

<400> SEQUENCE: 36
```

Met Lys Arg Arg Thr Leu Leu Ala Gly Ile Thr Leu Ala Ala Leu Val
            -25                 -20                 -15

Ala Val Ala Gly Cys Gly Thr Pro Ala Gly Asn Thr Ala Ser Pro Asp
        -10                 -5                  -1   1

Asn Thr Ala Asn Leu Ser Asn Thr Asn Ala Pro Asp Thr Leu Ser Asn
         5                  10                  15

Glu Thr Gly Gln Thr Leu Asp Thr Ala Asn Pro Pro Tyr Leu His Thr
 20                  25                  30                  35

Ser Thr Glu Gln Trp Lys Ser Met Pro Lys Met Phe Ile Asn Pro Asn
                 40                  45                  50

Lys Thr Tyr Asp Ala Ile Val His Thr Asn Tyr Gly Thr Phe Thr Ile
             55                  60                  65

Gln Leu Phe Ala Lys Asp Ala Pro Ile Thr Val Asn Asn Phe Val Phe
             70                  75                  80

Leu Ala Glu His Asn Phe Tyr His Asp Cys Thr Phe Phe Arg Ile Val
 85                  90                  95

Lys Asn Phe Val Ile Gln Thr Gly Asp Pro Arg Asn Asp Gly Thr Gly
100                 105                 110                 115

Gly Pro Gly Tyr Thr Ile Pro Asp Glu Leu Ser His Gln Val Pro Phe
                120                 125                 130

Thr Lys Gly Ile Val Ala Met Ala Asn Thr Gly Gln Pro His Thr Gly
            135                 140                 145

Gly Ser Gln Phe Phe Ile Cys Thr Ala Asn Asp Thr Gln Val Phe Gln
            150                 155                 160

Pro Pro Asn Asn Arg Tyr Thr Glu Phe Gly Arg Val Ile Ser Gly Met
165                 170                 175

Asp Val Ile Asp Lys Ile Ala Ala Ile Pro Val Thr Glu Asn Pro Met
180                 185                 190                 195

Thr Gln Glu Asp Ser Tyr Pro Leu Lys Thr Ala Tyr Ile Glu Ser Ile
                200                 205                 210

Gln Ile Gln Glu Ser
            215

```
<210> SEQ ID NO 37
<211> LENGTH: 608
<212> TYPE: PRT
<213> ORGANISM: Alicyclobacillus sp.
<220> FEATURE:
<221> NAME/KEY: SIGNAL
<222> LOCATION: (1)..(27)
<220> FEATURE:
<221> NAME/KEY: mat_peptide
<222> LOCATION: (28)..(608)
<223> OTHER INFORMATION: acid phosphatase or a phytase or a
      phospholipase C

<400> SEQUENCE: 37
```

Met Lys Lys Gly Lys Arg Trp Ser Ala Ala Leu Ala Thr Ser Val Ala
            -25                 -20                 -15

Leu Phe Ala Thr Leu Ser Pro Gln Ala Leu Ala Ser Asp Thr Val Val
-10                 -5                  -1   1               5

Pro Gln Val Asn Thr Leu Thr Pro Ile His His Leu Val Val Ile Phe
                10                  15                  20

Asp Glu Asn Val Ser Phe Asp His Tyr Phe Ala Thr Tyr Pro Asn Ala 25                  30                  35

Ala Asn Pro Ala Gly Glu Pro Pro Phe Tyr Ala Ala Pro Gly Thr Pro
            40                  45                  50

Ser Val Asn Gly Leu Ser Gly Ser Leu Leu Thr His Asn Pro Asn Gly
        55                  60                  65

Val Asn Pro Gln Arg Leu Asp Arg Ser Gln Ala Val Thr Pro Asp Met
70                  75                  80                  85

Asn His Asn Tyr Thr Pro Glu Gln Gln Ala Val Asp Gly Gly Arg Met
                90                  95                 100

Asp Asn Phe Ile Asn Thr Val Gly Arg Gly Asn Pro Ile Asp Leu Asp
               105                 110                 115

Tyr Tyr Asp Gly Asn Thr Val Thr Ala Leu Trp Tyr Ala Gln His
           120                 125                 130

Phe Ala Leu Asn Asp Asn Ala Tyr Cys Thr Gln Tyr Gly Pro Ser Thr
               135                 140                 145

Pro Gly Ala Ile Asn Leu Ile Ser Gly Asp Thr Ala Gly Ala Thr Val
150                 155                 160                 165

Tyr Ser Ser Ser Glu Thr Ser Gly Ala Ala Gln Val Val Pro Pro Gly
                170                 175                 180

Ser Lys Asn Phe Pro Asn Ala Val Thr Pro Asn Gly Val Asp Ile Gly
                185                 190                 195

Asp Ile Asp Pro Tyr Tyr Asp Ser Ala Ser Lys Gly Met Thr Met Ala
           200                 205                 210

Met Ala Gly Lys Asn Ile Gly Asp Leu Leu Asn Ala Lys Gly Val Thr
        215                 220                 225

Trp Gly Trp Phe Gln Gly Gly Phe Ala Asn Pro Asn Ala Lys Asp Asn
230                 235                 240                 245

Asn Ile Ala Gly Thr Asp Glu Thr Thr Asp Tyr Ser Ala His His Glu
                250                 255                 260

Pro Phe Gln Tyr Tyr Ala Ser Thr Ala Asn Pro Asn His Leu Pro Pro
           265                 270                 275

Thr Ser Val Ala Met Ile Gly Arg Thr Asp Gln Ala Asn His Gln Tyr
        280                 285                 290

Asp Ile Thr Asn Phe Phe Gln Ala Leu Gln Asn Gly Asn Met Pro Ala
    295                 300                 305

Val Ser Phe Leu Lys Ala Pro Glu Tyr Glu Asp Gly His Ala Gly Tyr
310                 315                 320                 325

Ser Asp Pro Leu Asp Glu Gln Arg Trp Leu Val Gln Thr Ile Asn Gln
                330                 335                 340

Ile Glu Ala Ser Pro Asp Trp Ser Ser Thr Ala Ile Ile Thr Tyr
           345                 350                 355

Asp Asp Ser Asp Gly Trp Tyr Asp His Val Met Pro Pro Leu Val Asn
           360                 365                 370

Gly Ser Ser Asp Lys Ala Val Asp Val Leu Gly Gly Thr Pro Val Leu
        375                 380                 385

Gln Asn Gly Thr Asp Arg Ala Gly Tyr Gly Pro Arg Val Pro Phe Leu
390                 395                 400                 405

Val Ile Ser Pro Tyr Ala Lys His Asn Phe Val Asp Asn Thr Leu Ile
               410                 415                 420

Asp Gln Thr Ser Val Leu Arg Phe Ile Glu Glu Asn Trp Gly Leu Gly
           425                 430                 435

Ser Leu Gly Pro Ala Ser Tyr Asp Ser Leu Ala Gly Ser Ile Met Asn
        440                 445                 450

```
Met Phe Asp Trp Asn Thr Gln Asn Pro Pro Val Phe Leu Asp Pro Thr
455                 460                 465

Thr Gly Glu Pro Val Ser Pro Asp Met Gln Pro Glu Val Ile Arg Gly
470                 475                 480                 485

Thr Thr Tyr Leu Ser Leu Asn His Tyr Ala Gln Asn Leu Asp Val Val
                490                 495                 500

Leu Gln Thr Ser Arg Gly Met Ala Arg Phe Ser Tyr Glu Gly His Glu
            505                 510                 515

Val Glu Ile Asp Glu Arg Ser Gly Leu Val Arg Val Asp Gly Glu Ala
        520                 525                 530

Val His Leu Lys Ala Pro Leu Val Arg Val Asp Gly Val Trp Met Val
    535                 540                 545

Pro Val Glu Glu Met Asp Ser Leu Ile Gly Ala Thr Leu His Thr Tyr
550                 555                 560                 565

Thr Asp Gly His Leu Thr Tyr Tyr Leu Phe Ser Pro Gln Asp Ala His
                570                 575                 580

<210> SEQ ID NO 38
<211> LENGTH: 250
<212> TYPE: PRT
<213> ORGANISM: Alicyclobacillus sp.
<220> FEATURE:
<221> NAME/KEY: SIGNAL
<222> LOCATION: (1)..(25)
<220> FEATURE:
<221> NAME/KEY: mat_peptide
<222> LOCATION: (26)..(251)
<223> OTHER INFORMATION: polysaccharide deacetylase or a xylan
      deacetylase

<400> SEQUENCE: 38

Met Leu Ser Leu Trp Lys Arg Ile Arg Thr Gly Thr Leu Ser Leu Leu
-25                 -20                 -15                 -10

Ala Ala Cys Ala Cys Ala Leu Ser Ala Met Gly Ala Gly Ala Gly Trp
            -5                  -1  1               5

Val His Ala Ala Glu Ser Gln Ala Gln Ala Pro Arg Ala Ile Tyr Lys
                10                  15                  20

Val Asp Thr Lys Glu Lys Val Val Ala Leu Thr Phe Asp Ile Ser Trp
25                  30                  35

Gly His Arg Thr Pro Glu Pro Val Leu Glu Thr Leu Lys Lys Cys Gly
40                  45                  50                  55

Val Thr Lys Ala Thr Phe Phe Leu Ser Gly Pro Trp Thr Met His His
                60                  65                  70

Ala Asp Ile Ala Lys Lys Ile Lys Ala Met Gly Tyr Glu Ile Gly Ser
            75                  80                  85

His Gly Tyr Leu His Lys Asp Tyr Ser Asn Tyr Pro Asp Ser Trp Ile
        90                  95                  100

Arg Glu Gln Ala Met Leu Ala Asp Lys Ala Ile Gln Gln Val Thr Gly
105                 110                 115

Val Lys Pro Lys Leu Phe Arg Thr Pro Asn Gly Asp Leu Asn Pro Arg
120                 125                 130                 135

Val Ile Arg Cys Leu Thr Ser Met Gly Tyr Thr Val Val Gln Trp Asn
                140                 145                 150

Thr Asp Ser Leu Asp Trp Lys Asn Pro Gly Val Asp Ala Ile Val Asn
            155                 160                 165

Arg Val Thr Lys Arg Val Val Pro Gly Asp Ile Ile Leu Met His Ala
        170                 175                 180

Ser Asp Ser Ser Lys Gln Ile Val Glu Ala Leu Pro Arg Ile Ile Glu
```

```
            185                 190                 195
Ser Leu Arg Gln Gln Gly Tyr Arg Phe Val Thr Val Ser Glu Leu Leu
200                 205                 210                 215

Ala Gly Ala Ser Val Gln Ser Lys Val Gln
                220                 225

<210> SEQ ID NO 39
<211> LENGTH: 324
<212> TYPE: PRT
<213> ORGANISM: Alicyclobacillus sp.
<220> FEATURE:
<221> NAME/KEY: SIGNAL
<222> LOCATION: (1)..(21)
<220> FEATURE:
<221> NAME/KEY: mat_peptide
<222> LOCATION: (22)..(324)
<223> OTHER INFORMATION: polysaccharide deacetylase or a xylan
      deacetylase

<400> SEQUENCE: 39

Met Arg Lys Thr Ala Ala Gly Ala Cys Ala Leu Ala Leu Met Gly Val
                -20                 -15                 -10

Leu Gly Gly Trp Ala Gly Ala Ala Gly Thr Ala Val Asn Ala His Ala
 -5              -1   1               5                  10

Pro Ala Ala Ser Ala Pro Ser Val Ser Ala His Val Trp Glu Glu Val
                 15                  20                  25

Ser Arg Thr Trp Gly Thr Leu Pro Val Asp Ala Arg His Asp Gly Val
             30                  35                  40

Trp His Asn Ile Pro Gly Leu Ser Gly Phe Ala Leu Asp Thr Ala Ala
         45                  50                  55

Ser Glu Arg Glu Thr Ala Arg Arg His Asp Gly Ala Leu His Leu Val
 60              65                  70                  75

Trp Arg Thr Leu Pro Pro Lys Arg Arg Leu Gly Asp Leu Ser Pro Asp
                 80                  85                  90

Val Ile Tyr Arg Gly Pro Ala Gln Glu Lys Ser Val Ala Leu Met Val
             95                 100                 105

Asn Val Ser Trp Gly Asp Ala Tyr Val Pro Arg Met Leu Glu Val Leu
            110                 115                 120

Arg Ser Ala His Val Lys Ala Thr Phe Phe Val Asp Gly Ala Phe Ala
            125                 130                 135

Lys Lys Phe Pro Asp Leu Val Arg Ala Met Ala Arg Asp Gly His Ala
140                 145                 150                 155

Val Glu Ser His Gly Phe Gly His Pro Asp Phe Arg Arg Leu Ser Asp
                160                 165                 170

Ala Lys Leu Ala Ala Gln Leu Asp Glu Thr Asn Arg Val Leu Ala Gly
            175                 180                 185

Ile Thr Gly Lys Val Pro Arg Leu Ile Ala Pro Pro Ala Gly Ser Tyr
            190                 195                 200

Asp Ala Arg Leu Ala Pro Leu Ala His Ser Arg Arg Met Tyr Ala Ile
            205                 210                 215

Leu Trp Thr Ala Asp Thr Val Asp Trp Lys Asn Pro Pro Ala Asp Val
220                 225                 230                 235

Ile Val Gln Arg Val Gln Arg Gly Ala Glu Pro Gly Ala Leu Ile Leu
                240                 245                 250

Met His Pro Thr Ala Pro Thr Ala Glu Ala Leu Pro Asp Val Ile Arg
            255                 260                 265

Trp Leu Glu Gly His Gly Tyr Arg Leu Lys Thr Val Glu Asp Val Ile
            270                 275                 280
```

Asp Glu Arg Pro Ala Val Thr Pro Pro Thr Thr Leu Ala Asn Glu Thr
    285                 290                 295

Phe His Ser Ala
300

<210> SEQ ID NO 40
<211> LENGTH: 214
<212> TYPE: PRT
<213> ORGANISM: Alicyclobacillus sp.
<220> FEATURE:
<221> NAME/KEY: SIGNAL
<222> LOCATION: (1)..(29)
<220> FEATURE:
<221> NAME/KEY: mat_peptide
<222> LOCATION: (30)..(214)
<223> OTHER INFORMATION: sulfite oxidase

<400> SEQUENCE: 40

Met Met Arg Trp Asn Trp Lys Val Ala Val Gly Ser Leu Ala Leu Ala
            -25                 -20                 -15

Ala Leu Gly Ala Gly Ala Ala Val Ser Pro Val Phe Ala Ala Ala Lys
        -10                  -5              -1   1

Ser Ser Lys Ala Ala Gln Ser His Ala Glu Ala Ser Ala Ala Val Val
      5                  10                  15

Met Ala Gly Lys Leu Tyr Gly Asn Ile Pro Asn Val Thr Ile Arg Gly
 20                  25                  30                  35

Val Glu Ala Gly Lys Ala Pro Trp Val Val Asp Gly Ser Tyr Gln Leu
                 40                  45                  50

Lys Ser Asn Leu Phe Thr Ala Ser Gly Lys Trp Leu Ile Ile Pro Lys
             55                  60                  65

Gln Gly Tyr Met Glu Asn Gly Gln Pro Val Pro Ala Lys Ile Gly Gly
         70                  75                  80

Thr Thr Asn Asn Ile Pro Ala Val Gly Ala Glu Ile Thr Phe Ala Asn
     85                  90                  95

Ala Ala Pro Ile Val Leu Pro Pro Val Lys Leu Ser Ser Gln Gly Asp
100                 105                 110                 115

Phe Ser Phe His Asp Ala Ile Gln Trp Pro Lys Gly Ala Ala Gln Pro
                120                 125                 130

Val Ile Leu Ile Gly Pro Glu Lys Asn Gly Gln Leu Val Ala Trp Phe
            135                 140                 145

Ala Ala Ser Asp Phe Leu Ala Asp Tyr Gly Gln Ala Thr Gly Met Gly
        150                 155                 160

Gly Gly Trp Val Asn Ala Ala His Pro Glu Thr Pro Val Arg His Thr
    165                 170                 175

His Leu Ala Ser Lys Lys
180             185

<210> SEQ ID NO 41
<211> LENGTH: 257
<212> TYPE: PRT
<213> ORGANISM: Alicyclobacillus sp.
<220> FEATURE:
<221> NAME/KEY: SIGNAL
<222> LOCATION: (1)..(21)
<220> FEATURE:
<221> NAME/KEY: mat_peptide
<222> LOCATION: (22)..(257)
<223> OTHER INFORMATION: functional polypeptide

<400> SEQUENCE: 41

Met Asn Trp Ala Arg Val Gly Ala Trp Val Ser Thr Trp Leu Val Ala

```
                -20              -15              -10
Thr Ala Leu Gly Ala Gly Cys Gly Thr Ala Ser Gln Glu His Pro Ser
 -5              -1  1               5                      10

Asn Thr Ser Thr Ser Asp His Arg Val Ala Pro Ala Ala Pro Gly Gly
             15                  20                  25

Ser Ala Ser Met Gln Asn Arg His Ile Leu Gln Glu Pro Leu Pro Arg
             30                  35                  40

Gly Val Lys Thr Glu Thr Asp Leu Tyr Asn Trp Leu Leu Trp Gln Arg
         45                  50                  55

Leu Ala Glu Ile Asn Asn Pro Ala Gln Gly Glu Ile Cys Leu Asp Ala
 60                  65                  70                  75

Ala Cys Lys Ile Ala Ala Thr Val Phe Ser Gly Pro Ala Lys Ala Ala
                 80                  85                  90

Ala Gly Thr Pro Val Thr Leu Val Ala Phe Ser Pro Arg Ala Gly Trp
             95                 100                 105

Gln Val Leu Val Gly Pro Leu Pro Gln Ser Asp Asn Pro Pro Arg Gln
        110                 115                 120

Ala Gln Ser Ile Thr Gly Gln Ser Ala Arg Leu Pro Ala Gln Arg Gly
        125                 130                 135

Arg Met Arg Arg Ser Asn Pro Arg Asn Arg Leu Val Leu Asp Ser Gly
140                 145                 150                 155

Arg Thr Pro Ala Ala Asp Ala Ser Ala Ala Arg Met Thr Arg Gln Leu
                160                 165                 170

Arg Arg Ser Ala Ser Ser Thr Asn Ala Ser Arg Ser Arg Arg Ala Lys
            175                 180                 185

Ser Met Ala Arg Cys Gln Lys Ser Gly Cys Val Arg Ser Ala Pro Met
        190                 195                 200

Cys Phe Trp Ala Arg Ser Ser Thr Arg Met Arg Pro Val Ser Arg Ser
205                 210                 215

Asn Ala Thr Tyr Leu Ser Ala Asn Pro Val Pro Ser Ala Glu Ala Met
220                 225                 230                 235

Ala

<210> SEQ ID NO 42
<211> LENGTH: 1130
<212> TYPE: PRT
<213> ORGANISM: Alicyclobacillus sp.
<220> FEATURE:
<221> NAME/KEY: SIGNAL
<222> LOCATION: (1)..(24)
<220> FEATURE:
<221> NAME/KEY: mat_peptide
<222> LOCATION: (25)..(1130)
<223> OTHER INFORMATION: functional polypeptide

<400> SEQUENCE: 42

Met Lys Arg Thr Leu Ser Gly Ile Ala Ser Ala Ala Ile Val Leu Gly
            -20                 -15                 -10

Ala Ile Ser Pro Met Ala Phe Ala Gln Thr Ser Ser Ser Gly Leu Thr
         -5              -1  1               5

Pro Ala Gly Gln Leu Pro Ile Val Val Asn Gly Gln Val Leu Ser Asn
         10                  15                  20

Pro Tyr Glu Met Val Gly Met Asp Ser Gly Asn Lys Thr Gly Phe Phe
 25                  30                  35                  40

Pro Ile Tyr Tyr Phe Asp Gln Ala Leu Glu Lys Ile Gly Ile Thr Ala
                 45                  50                  55

Thr Trp Asn Gly Ala Thr His Thr Trp Ala Leu Thr Asp Ser Asn Val
```

-continued

```
                60                  65                  70
Asn Ala Ser Asn Val Gln Val Ala Gly Gly Met Gly Thr Gly Asn Thr
                75                  80                  85
Thr Val Thr Leu Asn Gly Thr Pro Ile Lys Met Phe Tyr Thr Gln Val
                90                  95                 100
Ala Lys Asp Pro Ala Gly Pro Val Thr Thr Tyr Met Pro Ile Tyr
105                 110                 115                 120
Tyr Ile Asn Asn Ile Leu Ser Ala Leu Gly Ile His Gly Thr Phe Ser
                125                 130                 135
Gly Gln Thr Gly Leu Asn Ile Thr Thr Gly Gln Thr Leu Ala Gly Ser
                140                 145                 150
Leu Ser Ala Ile Thr Val Thr Gly Ala Thr Ser Gly Thr Gly Thr Ser
                155                 160                 165
Ser Ser Pro Ala Val Ala Leu Asn Asn Gly Lys Val Thr Leu Ser Thr
                170                 175                 180
Thr Leu Thr Asp Ser Asn Gly Asn Pro Ile Gly Asn Ala Ala Val Thr
185                 190                 195                 200
Phe Asn Phe Ser Glu Tyr Gly Ala Leu Pro Ser Asn Ala Pro Thr Val
                205                 210                 215
Thr Asn Ala Ser Gly Ala Thr Ile Pro Ala Thr Thr Gly Ser Thr Ala
                220                 225                 230
Tyr Gln Tyr Thr Val Tyr Thr Asn Ser Ser Gly Val Ala Ser Ile Thr
                235                 240                 245
Val Ser Gly Pro Val Gly Leu Thr Tyr Ala Tyr Gln Val Thr Ala Thr
                250                 255                 260
Ala Pro Ile Ser Asn Gly Ser Asn Gln Met Ile Ser Ser Gln Pro Ala
265                 270                 275                 280
Tyr Val Glu Phe Val Ala Asn Asn Gln Ala Gly Ile Ala Pro Tyr Gly
                285                 290                 295
Thr Ala Ser Gln Pro Tyr Ser Ala Ser Leu Gly Thr Ala Val Pro Ile
                300                 305                 310
Thr Val Ile Leu Pro Pro Gly Ala Asn Gly Gln Pro Gln Ala Asn Val
                315                 320                 325
Leu Val Thr Leu Ser Leu Ser Asn Pro Asn Gly Gly Thr Asn Tyr Ala
                330                 335                 340
Tyr Phe Thr Asn Ser Ser Gly Ala Asn Leu Gly Thr Gln Ile Gln Val
345                 350                 355                 360
Thr Thr Asn Ser Ser Gly Val Ala Gln Ala Trp Val Ser Asp Ala Asn
                365                 370                 375
Ala Gln Pro Val Val Thr Ala Asn Val Ser Asn Ala Thr Asn Val
                380                 385                 390
Ser Asn Thr Ser Val Ser Thr Tyr Leu Asn Phe Gly Gln Ala Gly Val
                395                 400                 405
Pro Ala Ser Ile Ala Asn Tyr Asn Asp Pro Tyr Ser Ala Leu Val Ala
                410                 415                 420
Asn Gly Gln Gln Pro Leu Ala Gly Thr Thr Val Thr Ile Thr Gly Thr
425                 430                 435                 440
Leu Val Asp Ala Ala Gly Asn Pro Val Ala Asn Gly Gln Val Leu Val
                445                 450                 455
Thr Gly Ser Ser Ser Gly Asp Phe Gly Tyr Val Thr Thr Ser Asn
                460                 465                 470
Gly Lys Ser Thr Thr Asp Phe Pro Ser Val Gly Leu Gln Pro
                475                 480                 485
```

```
Gly Gln Pro Val Ser Ser Ala Leu Gly Asp Val Ile Thr Ala Asp Ala
    490                 495                 500

Asn Gly Asn Phe Ser Leu Gln Val Thr Asp Thr Gln Asn Glu Gln Ala
505                 510                 515                 520

Ser Leu Thr Phe Tyr Ser Val Ser Asn Gly Val Ile Ser Pro Val Gly
                525                 530                 535

Val Ile Lys Thr Asp Thr Leu Lys Phe Ala Val Asn Asn Gln Leu Ser
            540                 545                 550

Thr Ile Ala Leu Gly Ala Thr Asp Ala Gln Ala Asp Gly Asn Gln Tyr
        555                 560                 565

Thr Asn Leu Thr Gly Leu Thr Gly Ser Asp Asn Ala Pro Val Pro Val
    570                 575                 580

Tyr Val Asp Pro Gln Asn Pro Ser Gly Thr Met Val Thr Asn Gln Ser
585                 590                 595                 600

Ile Thr Tyr Thr Leu Ser Val Ser Ser Gly Asp Ile Val Gly Ile Gly
                605                 610                 615

Ser Gly Ala Tyr Leu Ala Pro Thr Asn Ala Asn Asn Ser Thr Ile Pro
            620                 625                 630

Ile Asn Ser Gly Asn Gly Leu Ser Ser Val Gln Val Thr Val Thr Ala
        635                 640                 645

Leu Gly Asn Asn Gln Tyr Gln Ile Ser Val Pro Gly Gln Gln Gly Val
    650                 655                 660

Leu Thr Thr Ser Ser Pro Asp Phe Thr Val Leu Val Lys Gly Ser Thr
665                 670                 675                 680

Gly Ser Thr Lys Leu Thr Val Ser Ser Gly Ser Leu Ser Ser Thr Ala
                685                 690                 695

Thr Ile Thr Phe Thr Ser Ser Asn Pro Thr Val Val Ala Ser Leu Thr
            700                 705                 710

Pro Val Ser Ser Val Leu Ala Ala Gly Gln Asn Glu Thr Val Thr Phe
        715                 720                 725

Thr Val Glu Asp Ala Asp Gly Asn Pro Val Ser Gly Asn Thr Gln Val
    730                 735                 740

Ala Ile Thr Ala His Asp Ser Asn Asp Pro Leu Trp Ile Thr Ala Val
745                 750                 755                 760

Asn Gly Thr Asn Leu Ser Glu Tyr Glu Thr Ile Asn Gly Ala Ala Thr
                765                 770                 775

Ser Val Ser Thr Pro Ile Pro Leu Gly Thr Ser Ser Tyr Ala Thr Ser
            780                 785                 790

Gly Gly Ser Thr Leu Tyr Pro Ala Tyr Thr Asn Ser Gly Tyr Phe Lys
        795                 800                 805

Asn Gly Val Ser Ile Ser Gly Val Val Ser Trp Asp Gly Thr Val Gly
    810                 815                 820

Asp Pro Ile Tyr Val Thr Thr Asn Ser Gln Gly Gln Val Thr Leu Thr
825                 830                 835                 840

Leu Gln Asn Gly Asn Val Thr Tyr Phe Asp Gly Asn Asn Thr Thr Leu
                845                 850                 855

Ser Asn Gly Ile Ser Val Ala Gly Thr Ser Gly Ser Glu Gly Phe Tyr
            860                 865                 870

Thr Tyr Ser Ser Asp Thr Ala Ala Thr Ala Ser Asp Leu Thr Asn Met
        875                 880                 885

Gly Val Leu Val Ile Gly Gln Ala Asn Gly Asp Ala Ser Thr Ser Leu
    890                 895                 900

Gly Thr Ile Tyr Ile Gly Ser Gly Gly Ala Thr Gln Thr Pro Ala Ala
905                 910                 915                 920
```

-continued

```
Phe Thr Tyr Val Asp Ala Asn Asn His Ser Tyr Thr Tyr Ser Asn Thr
                925                 930                 935

Ser Asp Thr Phe Thr Val Ser Ser Thr Gln Ser Val Ser Gly Gly Asn
                940                 945                 950

Tyr Ala Ile Thr Ser Phe Thr Pro Val Gly Gly Thr Ala Thr Ser Thr
            955                 960                 965

Ile Pro Ser Gly Val Ser Val Asn Ser Ser Thr Gly Thr Val Ser Val
    970                 975                 980

Ser Gln Asn Ala Ala Val Gly Thr Tyr Thr Val Ser Tyr Tyr Leu Asn
985                 990                 995                 1000

Gly Val Thr Glu Ser  Thr Gly Thr Phe Lys  Val Tyr Ser Gly Ser
                1005                1010                 1015

Gly Val Ala Pro Thr  Glu Ile Thr Gly Ser  Ser Val Thr Val Pro
                1020                1025                 1030

Ala Ala Thr Tyr Ser  Gly Thr Leu Lys Val  Thr Val Ser Asn Gly
                1035                1040                 1045

Gly Ser Pro Leu Tyr  Val Asn Val Thr Ala  Gly Glu Ser Ala Asn
                1050                1055                 1060

Ala Val Ala Ala Ala  Ile Tyr Asn Ala Leu  Val Asn Ala Asn Ile
                1065                1070                 1075

Ser Gly Asp Thr Phe  Ser Val Ser Gly Ser  Thr Val Ser Val Thr
                1080                1085                 1090

Ala Ala Ser Gly Ser  Pro Thr Leu Thr Val  Val Asp Ala Thr Asn
                1095                1100                 1105

Phe

<210> SEQ ID NO 43
<211> LENGTH: 248
<212> TYPE: PRT
<213> ORGANISM: Alicyclobacillus sp.
<220> FEATURE:
<221> NAME/KEY: SIGNAL
<222> LOCATION: (1)..(41)
<220> FEATURE:
<221> NAME/KEY: mat_peptide
<222> LOCATION: (42)..(248)
<223> OTHER INFORMATION: functional polypeptide

<400> SEQUENCE: 43

Met Arg Ile Met Lys Val Leu Gly Trp Ile Leu Val Pro Tyr Ile Met
    -40                 -35                 -30

Leu Phe Ile Gln Trp Gly Arg Met Asn Arg Ile Leu Arg Phe Ala Gly
-25                 -20                 -15                 -10

Ser Leu Trp Ala Leu Ile Val Phe Ala Asn Thr Val Tyr Met Ile Arg
            -5                  -1  1                   5

Gly Asn Thr Pro Arg Asn Ala Ser Thr Val Ser Ala Thr Thr Ser Leu
            10                  15                  20

Val Asn Ser Thr Asn Ser Ser Gln Val Ala Lys Gln Glu Gln Asn Ser
        25                  30                  35

Ser Thr Ser Pro Ala His Lys Ser Thr Asn Ser Leu Gln His Ala Gln
40                  45                  50                  55

His Gln Ala Ala Thr Thr Ser Ser Ser Gln Ser Lys Leu Arg Tyr Ile
                60                  65                  70

Pro Phe His Thr Tyr Gly Lys Val Gly Asp Leu Glu Ile Arg Val Asn
            75                  80                  85

Ser Leu Gln Gln Val Lys Ser Val Gly Tyr Asp Gly Ile Gly Glu Thr
        90                  95                  100
```

```
Ala Asn Gly Ala Phe Trp Val Ile Asn Ile Thr Ile Arg Asn Asp Gly
    105                 110                 115

Ser Thr Pro Met Glu Val Val Asp Gly Ile Phe His Leu Gln Asn Leu
120                 125                 130                 135

Asn Gly Asn Val Tyr Gln Pro Asp Ser Thr Ala Glu Ile Tyr Ala Asn
                140                 145                 150

Thr Asn Ser Gly Thr Ile Pro Thr Asp Leu Asn Pro Gly Val Ser Met
            155                 160                 165

Thr Thr Asn Leu Val Phe Asp Met Pro Asp Phe Met Thr Tyr Gly His
        170                 175                 180

Val Gly Gln His Tyr Ser Leu Val Ala Ser Met Gly Phe Phe Gly Ser
    185                 190                 195

Asp Glu Thr Thr Tyr Ala Leu Pro
200                 205

<210> SEQ ID NO 44
<211> LENGTH: 172
<212> TYPE: PRT
<213> ORGANISM: Alicyclobacillus sp.
<220> FEATURE:
<221> NAME/KEY: SIGNAL
<222> LOCATION: (1)..(25)
<220> FEATURE:
<221> NAME/KEY: mat_peptide
<222> LOCATION: (26)..(172)
<223> OTHER INFORMATION: functional polypeptide

<400> SEQUENCE: 44

Met Asn Arg Lys Ser Met Leu Ser Val Leu Gly Val Ala Ala Ala Val
-25                 -20                 -15                 -10

Ala Leu Met Val Thr Gly Cys Gly Thr Ala Asn Ser Thr Asn Asn Thr
            -5                  -1  1                   5

Ala Ser Ser Gly Ala Ala Ser Thr Ala Val Thr Val Lys His Glu His
        10                  15                  20

Lys Gly Ala Asn Ala Ser Lys Thr Glu Thr Lys Gln Thr Glu Ala Lys
    25                  30                  35

Ser Ser Asn Lys Ala Gly Glu Thr Ala Lys Ser Ser Val Lys Leu Thr
40                  45                  50                  55

Ala Pro Val Ala Gly Ala Thr Val Thr Ala Gly Gly Thr Leu Lys Val
                60                  65                  70

Ser Gly Gln Val Ser Ser Asn Leu Ala Lys Lys Asp Val Gln Ile Thr
            75                  80                  85

Leu Thr Asn Ser Ala Lys Lys Val Leu Val Gln Gln Ile Val Gly Thr
        90                  95                  100

Asn Ser Thr Gly Ala Phe Val Asp Thr Leu Lys Leu Pro Lys Tyr Leu
    105                 110                 115

Gly Lys Ala Gly Ser Asp Leu Thr Leu Ser Val Ser Val Val Gly Glu
120                 125                 130                 135

Asn Gly Val Val Ser Thr Leu Ser Leu His Val Lys
                140                 145

<210> SEQ ID NO 45
<211> LENGTH: 242
<212> TYPE: PRT
<213> ORGANISM: Alicyclobacillus sp.
<220> FEATURE:
<221> NAME/KEY: SIGNAL
<222> LOCATION: (1)..(30)
<220> FEATURE:
<221> NAME/KEY: mat_peptide
```

<222> LOCATION: (31)..(242)
<223> OTHER INFORMATION: functional polypeptide

<400> SEQUENCE: 45

```
Met Arg Arg Ala Val Arg Ile Leu Ala Ala Leu Leu Phe Gly Leu Ala
-30                 -25                 -20                 -15
Thr Val Thr Ala Thr Leu Met Phe Val Pro Gln Ala Arg Ala Ala Thr
            -10                  -5                  -1   1
Val Thr Gly Ala Leu Ala Gln Ser Gln Val Val Ser Ile Thr Gly Gly
              5                  10                  15
Tyr Asn Thr Thr Thr Gln Met Tyr Glu Gln Thr Gly Gln Gln Thr Val
         20                  25                  30
Val Thr Asn Trp Thr Phe Ser Leu Gln Gln Thr Val Asn Gln Asn Asn
 35                  40                  45                  50
Glu Asn Pro Ser Tyr Ala Gln Cys Thr Val Leu Ala Gly Asn Gln Gln
                 55                  60                  65
Val Thr Cys Thr Ser Asp Ala Thr Asn Asn Gly Ala Ile Cys Thr Ser
             70                  75                  80
Pro Tyr Pro Gly Ala Ile Asp Lys Gln Cys Thr Asn Leu Ile Gly Phe
         85                  90                  95
Thr Gly Asn Ile Ser Val Ser Ser Gln Asn Gly Asn Pro Thr Phe Thr
        100                 105                 110
Phe Ser Leu Pro Ser Ile Asp Pro Ser Thr Met Lys Pro Val Gly Ile
115                 120                 125                 130
Phe Val Thr Pro Glu Thr Ile Tyr Gly Gln Met Gly Thr Gly Ser Glu
                135                 140                 145
Ser Tyr Leu Ser Ser Gly Gln Ser Gly Gly Trp Ser Phe Asn Phe Ser
            150                 155                 160
Asn Val Ser Asp Pro Gln Asp Trp Tyr Phe Leu Leu Glu Phe Leu Ala
        165                 170                 175
Asn Pro Ile Val Ala Ala Ile Ala Val Pro Thr Thr Gln Thr Val Pro
        180                 185                 190
Ile Tyr Ser Trp Val Thr Thr Thr Val Trp His Pro Val Gln Ile Ser
195                 200                 205                 210
Tyr Ser
```

<210> SEQ ID NO 46
<211> LENGTH: 180
<212> TYPE: PRT
<213> ORGANISM: Alicyclobacillus sp.
<220> FEATURE:
<221> NAME/KEY: SIGNAL
<222> LOCATION: (1)..(24)
<220> FEATURE:
<221> NAME/KEY: mat_peptide
<222> LOCATION: (25)..(180)
<223> OTHER INFORMATION: functional polypeptide

<400> SEQUENCE: 46

```
Val Val Arg Met Arg Lys Arg Leu Gly Leu Val Leu Ser Met Val Thr
                -20                 -15                 -10
Ser Val Leu Val Gly Cys Gly Ala Ser His Pro Ser Pro Leu Asn Gln
         -5                  -1   1                   5
Asp Lys Ser Leu Leu Thr Trp Asn Ala Ala Lys His Glu Val Arg Trp
         10                  15                  20
Lys Val Val Ala Gly Asp Gly Arg Ala Asn Gly Gly Met Asn Phe Asp
 25                  30                  35                  40
Gly Tyr Ala Asn Gly Ser Met Thr Leu Val Val Pro Ile Gly Trp Arg
```

```
                45                  50                  55
Val Val Ile Asp Phe Asp Asn Ala Ser Leu Met Pro His Ser Ala Met
            60                  65                  70

Val Val Pro Tyr Gly Asp Arg Glu Arg Ser Asn Phe Asp Ala Thr Met
            75                  80                  85

Val Ala Phe Pro Gly Ala Glu Thr Pro Asn Pro Ser Gln Gly Asp Pro
            90                  95                 100

Gln Gly Thr His Arg Asp Val Ile Phe Thr Ala Ala Lys Val Gly Thr
105                 110                 115                 120

Tyr Ala Leu Val Cys Gly Val Pro Gly His Ala Leu Ala Gly Met Trp
                125                 130                 135

Asp Gln Leu Val Val Ser Asp Glu Ala Lys His Pro Ser Leu Arg Val
                140                 145                 150

Gln Arg Asp Ser
    155

<210> SEQ ID NO 47
<211> LENGTH: 477
<212> TYPE: PRT
<213> ORGANISM: Alicyclobacillus sp.
<220> FEATURE:
<221> NAME/KEY: SIGNAL
<222> LOCATION: (1)..(25)
<220> FEATURE:
<221> NAME/KEY: mat_peptide
<222> LOCATION: (26)..(477)
<223> OTHER INFORMATION: functional polypeptide

<400> SEQUENCE: 47

Met Ala Val Arg Arg Ala Trp Leu Leu Ala Pro Leu Cys Ala Ser Ser
-25                 -20                 -15                 -10

Leu Val Val Pro Ala Ser Val Gln Ala Gly Leu Ala Gln Gly His Gly
                -5                  -1  1                   5

Ser Phe Ser Thr Val Arg Val Ser Val Gly Thr Ser Ser Ser Leu Ser
            10                  15                  20

Val Pro Ala Leu Ile Gln Gly Asn Glu Thr Tyr Ile Pro Leu Trp Asp
            25                  30                  35

Leu Met Gln Val Leu His Gln Leu Gly Phe Thr Ala Thr Trp Ala Lys
40                  45                  50                  55

Gly Gln Phe Ser Val Ser Ala Pro Pro Ser Val Pro Met Asp Glu Ala
                60                  65                  70

Pro Gly Pro Ala Gly Lys Gly Gly Ala Leu Val Val Leu Asp Gly Gln
            75                  80                  85

Val Val Glu Gln Val Pro Thr Val Ile Ala Thr Pro Pro Gly Ala Ala
            90                  95                 100

Thr Pro Glu Val Phe Leu Pro Leu Thr Asn Ala Glu Glu Ile Leu Gly
            105                 110                 115

Arg Leu Gly Ile Gln Ala Ser Thr Gly Asn Gln Val Asn Leu Asp
120                 125                 130                 135

Ala Ser Ala Val Pro Gln Ala Leu Pro Asn Gln Gln Val Ala Val Trp
                140                 145                 150

Asn Val Leu Ala Ala Val Ala Ser Asp Leu Gly Val Ser Thr Ala Pro
                155                 160                 165

Ala Gly Pro Ser Pro Tyr Ala Asp Leu Pro Thr Ala Ser Pro Ala Trp
            170                 175                 180

Gly Ala Val Glu Ala Ala Ile Arg Leu Gly Trp Tyr Ser Pro Leu Ser
            185                 190                 195
```

```
Ala Ser Ser Ser Gly Ala Phe Gln Pro Ile Thr Trp Ala Gln Thr Ala
200                 205                 210                 215

Ser Ile Leu Trp Asn Ala Leu Gly Ile Ser Gln Gln Asp Ala Ala Tyr
            220                 225                 230

Gln Pro Gly Gly Ser Pro Thr Ala Trp Ala Ser Ala Leu Gly Leu Val
        235                 240                 245

Pro Glu Asn Trp Asp Pro Ala Ser Tyr Met Thr Ala Gln Glu Leu Asp
    250                 255                 260

Thr Leu Ala Ser Asn Leu His Glu Cys Leu Gln Gly Asp Val Glu Thr
265                 270                 275

Gly Ala Asn Thr Trp Arg Leu Trp Tyr Pro Pro Ala Asp Glu Val Glu
280                 285                 290                 295

Ala Thr Leu Gln Ser Gly Gly Gln Ser Leu Phe Thr Ser Thr Ala
                300                 305                 310

Asp Ala Gln Ala Ala Ile Ser Ser Ala Tyr Gln Phe Phe Asn Gln Leu
                315                 320                 325

Val Val Thr Arg Val Gly Gln Gly Tyr Val Val Thr Val Pro Ser Val
            330                 335                 340

Pro Glu Gly Tyr Gly Phe Ala Thr Phe Ser Ala Leu Gly Gly Val Ala
    345                 350                 355

Tyr Gln Thr Thr Pro Gly Gly Pro Trp Thr Val Val Pro Val Leu Asp
360                 365                 370                 375

Thr Arg Asp Val Ser Ile Pro Ala Lys Gly Arg Leu Ser Val Lys Val
                380                 385                 390

Pro Ala Gln Gly Ile Thr Ile Thr Trp Asn Met Met Pro Ser Leu
                395                 400                 405

Gly Gly Thr Val Ala Met Gly Ala Leu Gln Val Ser Pro Gly Pro Ser
            410                 415                 420

Gly Pro Ser Val Glu Arg Leu Asn Ile Val Thr Pro Asn Leu Pro Pro
        425                 430                 435

Val Leu Pro Ser Ser Val Thr Ser Thr Gln Pro Gln Ser
440                 445                 450

<210> SEQ ID NO 48
<211> LENGTH: 340
<212> TYPE: PRT
<213> ORGANISM: Alicyclobacillus sp.
<220> FEATURE:
<221> NAME/KEY: SIGNAL
<222> LOCATION: (1)..(19)
<220> FEATURE:
<221> NAME/KEY: mat_peptide
<222> LOCATION: (20)..(340)
<223> OTHER INFORMATION: functional polypeptide

<400> SEQUENCE: 48

Met Asn Arg Gln Trp Arg Leu Ala Val Ala Thr Ser Ala Val Ala Ala
                -15                 -10                  -5

Ser Leu Ala Gly Cys Gly Ala Pro Asp Leu Ala Ala Met Arg Pro Thr
         -1   1               5                  10

Val Gln Lys Ser Ala Val Leu Val Glu Val Val Gly Ala Pro Pro Phe
         15                  20                  25

Ala Pro Ser Ala Ser Gln Leu Gly Thr Ala Gly Ala Thr Ser Val Glu
30                  35                  40                  45

Val Val His Val Ala Leu Gly Glu Trp Gln Ser Val Ala Ala His Ala
                 50                  55                  60

Leu Ala Lys Gly Gln Leu Thr Gly Val Met Val Val Cys Asp Asp Ala
            65                  70                  75
```

```
Asn Ala Val Ala Ser Gly Leu Asn Gln Leu Ala Ala Asp His Pro Asp
            80                  85                  90

Val Arg Phe Leu Val Val Ser Asn Trp Pro Ala Ser Gln Ile Thr Ser
 95                 100                 105

Gly Asn Val Glu Asp Val Ala Gln Asp Pro Val Ala Val Ala Tyr Ser
110                 115                 120                 125

Ile Gly Ala Leu Cys Gly Asp Trp Ile Ala Ser Ser Thr Ser Thr Ser
                130                 135                 140

Gly Ala Val Tyr Ser Gly Val Pro Ser Ile Val Tyr Ala Pro Arg Gly
                145                 150                 155

Ala Thr Val Ala Glu Gln Lys Ala Phe Phe Thr Gly Leu Tyr Gln Ala
                160                 165                 170

Asn Pro Asn Val Arg Val Ala Leu Pro Gln Pro Ala Ala Gln Ser
        175                 180                 185

Leu Ser Ser Tyr Gly Tyr Ala Val Asp Leu Gly Val Val Gly Gly Ser
190                 195                 200                 205

Pro Ala Ala Gly Glu Leu Ser Ala Leu Arg Ser Ala Ala Pro Ala Trp
                210                 215                 220

Ala Ala Phe Gly Thr Ser Pro Ile Ala Gly Phe Ala Ile Ser Pro Gly
                225                 230                 235

His Leu Ser Ser Ser Glu Ala Val Gln Ala Phe Gln Ala Leu Val Ser
                240                 245                 250

Pro Asp Ala Trp His Ser Gly Glu His Leu Val Leu Asp Leu Ser Ser
        255                 260                 265

Val Ala Phe Asp Asp Lys Gln Val Pro Ala Thr Val Ile Ala Ala Trp
270                 275                 280                 285

Ala Lys Leu Glu Val Asn Ala Ile Ala Ala Ala Gln Ser Asn Ala
                290                 295                 300

Ala Phe Ala Ser Leu Pro Pro Ser Val Arg Ser Asp Leu Ala Asn Ala
                305                 310                 315

Phe His Leu Ser
        320

<210> SEQ ID NO 49
<211> LENGTH: 341
<212> TYPE: PRT
<213> ORGANISM: Alicyclobacillus sp.
<220> FEATURE:
<221> NAME/KEY: SIGNAL
<222> LOCATION: (1)..(29)
<220> FEATURE:
<221> NAME/KEY: mat_peptide
<222> LOCATION: (30)..(341)
<223> OTHER INFORMATION: functional polypeptide

<400> SEQUENCE: 49

Met Val Met Arg Thr Arg Trp Ile Arg Trp Met Ala Leu Ala Leu Ala
            -25                 -20                 -15

Val Cys Val Trp Leu Ser Pro Phe Pro Phe Ser Trp Gly Ala Thr Ser
        -10                  -5                  -1   1

Leu Asp Ala Asp Leu Pro Gln Pro Thr Ile Pro Pro Ser Ala Trp Ser
  5                  10                  15

Asn Leu Asn Gln Asp Trp Lys Asp Leu Gln Arg Leu Ala Gln Asn Thr
 20                  25                  30                  35

Val Pro Pro Ser Lys Glu Ser Ser Gln Thr His Ala Pro Thr His Lys
                 40                  45                  50

Ser Ser Gln Pro Pro Ala Gln Val Pro Gln Gly Pro Leu Val Gly Val
```

```
                55                  60                  65
Gly Asp Thr Gly Glu Ala Ala Arg Trp Leu Asn Glu Ala Leu Ala Val
            70                  75                  80

Leu Gly Tyr Leu Pro Ala Val Phe Ser Pro Ala Ala Gln Thr Ser Thr
        85                  90                  95

Arg Gln Val Arg Leu Ala Leu Ala Ala Ser Ala Glu His Gln Thr Leu
100                 105                 110                 115

Val Pro Ile Pro Gly Ser Phe Gln Leu Leu Tyr His Ala Pro Ser Ser
                120                 125                 130

Trp Val Ala Leu Trp Ser Ala Asp Glu Asp Thr Pro Ile Thr Glu Gly
            135                 140                 145

Ala Val Met Ala Phe Glu Ala Gln His His Leu Gly Val Asp Gly Ile
        150                 155                 160

Ala Gly Pro Asp Val Ile His Ala Leu Ala Gln Ala Leu Ala Gly Asn
    165                 170                 175

Glu Thr Ala Glu Lys Ala Pro Tyr Ser Tyr Ile Leu Val Thr Thr Ser
180                 185                 190                 195

Leu Pro Glu Thr Leu Glu Leu Trp Val Asn Gly Gln Leu Val Leu Lys
                200                 205                 210

Ser Leu Cys Asn Thr Gly Ile Ala Gln Ser Pro Thr Pro Tyr Gly Thr
            215                 220                 225

Tyr Gly Val Tyr Val Gln Tyr Thr Ser Gln Glu Met Lys Gly Lys Asp
        230                 235                 240

Pro Asp Gly Thr Pro Tyr Asp Asp Pro Gly Val Pro Trp Val Ser Tyr
    245                 250                 255

Phe Tyr Lys Gly Cys Ala Val His Gly Phe Leu Arg Ala Lys Tyr Gly
260                 265                 270                 275

Phe Pro Gln Ser Leu Gly Cys Val Glu Leu Pro Tyr Ala Ala Ala Lys
                280                 285                 290

Thr Val Phe Ser Tyr Thr His Ile Gly Thr Leu Val Thr Val Thr Ala
            295                 300                 305

Ser Pro Leu Ser Ala
        310

<210> SEQ ID NO 50
<211> LENGTH: 399
<212> TYPE: PRT
<213> ORGANISM: Alicyclobacillus sp.
<220> FEATURE:
<221> NAME/KEY: SIGNAL
<222> LOCATION: (1)..(28)
<220> FEATURE:
<221> NAME/KEY: mat_peptide
<222> LOCATION: (30)..(399)
<223> OTHER INFORMATION: functional polypeptide

<400> SEQUENCE: 50

Met Asp Arg Leu Leu Asn Asn Lys Val Ala Leu Arg Leu Thr Ala Leu
                -25                 -20                 -15

Val Leu Ala Cys Ile Leu Trp Leu Ala Val His Ala Glu Gln Gly Ser
        -10                 -5                  -1   1

Gly Ser Ser Ala Ser Thr Gly Val Thr Glu Ser Phe Glu Leu Pro Val
     5                  10                  15

Arg Val Glu Thr Ser Ala Asp Glu Val Leu Ser Gln Val Pro Thr
20                  25                  30                  35

Ile Thr Ala Arg Val Thr Thr Asn Leu Leu Ser Leu Pro Thr Leu Ala
            40                  45                  50
```

-continued

```
Ser Asp Met Met Lys Ala Glu Ile Val Ala Asp Ala Glu Asn Leu Gly
            55                  60                  65

Pro Gly Thr Tyr Thr Leu His Val Ala Ala Val Asn Met Pro Ala Gly
        70                  75                  80

Val Arg Ser Tyr Thr Leu Thr Pro Ser Thr Ile Thr Val Thr Leu Glu
    85                  90                  95

Pro Lys Val Thr Val Glu Arg Thr Val Arg Val Asn Val Val Gly Thr
100                 105                 110                 115

Pro Gly Gln Gly Tyr Val Leu Gly Lys Pro Glu Leu Gly Ala Gly Val
                120                 125                 130

Val Glu Val Ser Gly Ala Glu Ser Ser Val Gln Ala Val Ala Glu Val
                135                 140                 145

Ala Gly Val Val Asp Ala Ser Gly Leu Ser Gln Thr Ala Thr Lys Leu
            150                 155                 160

Val Glu Leu Leu Pro Leu Asp Gln Ala Gly Lys Ala Val Pro Gly Val
            165                 170                 175

Thr Val Thr Pro Ser Ala Ile Ser Val Thr Leu Pro Ile Thr Ser Ala
180                 185                 190                 195

Asn Gln Ala Val Lys Leu Thr Pro Ala Val Thr Gly Ser Pro Ala Pro
                200                 205                 210

Gly Tyr Ala Val Ala Ser Val His Leu Glu Pro Ala Ser Ala Val Glu
                215                 220                 225

Gln Gly Leu Ala Ala Ser Gln Leu Pro Gln Arg Gly Leu Leu Val Pro
            230                 235                 240

Ile Asp Val Thr Gly Leu Asn Arg Pro Thr Thr Val Ser Val Pro Val
            245                 250                 255

Pro Leu Leu Pro Gly Met Thr Ser Val Ser Pro Thr Ala Val Thr Ala
260                 265                 270                 275

Val Ile Asp Val Glu Pro Ser Ala Val Tyr Thr Val Ser Asn Val Pro
                280                 285                 290

Val Ala Ile Thr Gly Ala Thr Gly Val Lys Leu Val Thr Pro Arg Thr
            295                 300                 305

Val Asn Val Thr Val Thr Gly Ile Glu Ala Asp Val Arg Ala Val Glu
            310                 315                 320

Arg Asp Pro Ala Ala Val Gln Ala Phe Val Asp Ala Thr Gly Leu Thr
325                 330                 335

His Gly Ser Ala Thr Leu Pro Asp Ser Asn Ser Ala Val Leu Ser
                345                 350                 355

Leu Val Ile Arg Pro Arg Glu Arg Lys Arg Thr His Val Val
            360                 365                 370

<210> SEQ ID NO 51
<211> LENGTH: 34
<212> TYPE: DNA
<213> ORGANISM: Artificial Sequence
<220> FEATURE:
<223> OTHER INFORMATION: Primer SigA2NotU-P

<400> SEQUENCE: 51
tcgcgatccg ttttcgcatt tatcgtgaaa cgct                            34

<210> SEQ ID NO 52
<211> LENGTH: 33
<212> TYPE: DNA
<213> ORGANISM: Artificial Sequence
<220> FEATURE:
<223> OTHER INFORMATION: Primer SigA2NotD-P
```

<400> SEQUENCE: 52
ccgcaaacgc tggtgaaagt aaaagatgct gaa                              33

<210> SEQ ID NO 53
<211> LENGTH: 20
<212> TYPE: DNA
<213> ORGANISM: Artificial Sequence
<220> FEATURE:
<223> OTHER INFORMATION: Primer A2up

<400> SEQUENCE: 53
agcgtttgcg gccgcgatcc                                             20

<210> SEQ ID NO 54
<211> LENGTH: 21
<212> TYPE: DNA
<213> ORGANISM: Artificial Sequence
<220> FEATURE:
<223> OTHER INFORMATION: Primer B

<400> SEQUENCE: 54
ttattcggtc gaaaaggatc c                                           21

<210> SEQ ID NO 55
<211> LENGTH: 282
<212> TYPE: PRT
<213> ORGANISM: Aspergillus niger
<220> FEATURE:
<221> NAME/KEY: SIGNAL
<222> LOCATION: (1)..(18)
<220> FEATURE:
<221> NAME/KEY: PROPEP
<222> LOCATION: (19)..(59)
<220> FEATURE:
<221> NAME/KEY: CHAIN
<222> LOCATION: (60)..(98)
<220> FEATURE:
<221> NAME/KEY: PROPEP
<222> LOCATION: (99)..(109)
<220> FEATURE:
<221> NAME/KEY: CHAIN
<222> LOCATION: (110)..(282)
<220> FEATURE:
<221> NAME/KEY: MOD_RES
<222> LOCATION: (110)..(110)
<220> FEATURE:
<221> NAME/KEY: DISULFID
<222> LOCATION: (115)..(139)
<220> FEATURE:
<221> NAME/KEY: DISULFID
<222> LOCATION: (127)..(210)

<400> SEQUENCE: 55

Met Lys Phe Ser Thr Ile Leu Thr Gly Ser Leu Phe Ala Thr Ala Ala
  1               5                  10                  15

Leu Ala Ala Pro Leu Thr Glu Lys Arg Arg Ala Arg Lys Glu Ala Arg
                 20                  25                  30

Ala Ala Gly Lys Arg His Ser Asn Pro Pro Tyr Ile Pro Gly Ser Asp
             35                  40                  45

Lys Glu Ile Leu Lys Leu Asn Gly Thr Thr Asn Glu Glu Tyr Ser Ser
         50                  55                  60

Asn Trp Ala Gly Ala Val Leu Ile Gly Asp Gly Tyr Thr Lys Val Thr
 65                  70                  75                  80

Gly Glu Phe Thr Val Pro Ser Val Ser Ala Gly Ser Ser Gly Ser Ser
                 85                  90                  95

Gly Tyr Gly Gly Gly Tyr Gly Tyr Trp Lys Asn Lys Arg Gln Ser Glu
            100                 105                 110

```
                    -continued

Glu Tyr Cys Ala Ser Ala Trp Val Gly Ile Asp Gly Asp Thr Cys Glu
        115                 120                 125

Thr Ala Ile Leu Gln Thr Gly Val Asp Phe Cys Tyr Glu Asp Gly Gln
        130                 135                 140

Thr Ser Tyr Asp Ala Trp Tyr Glu Trp Tyr Pro Asp Tyr Ala Tyr Asp
145                 150                 155                 160

Phe Ser Asp Ile Thr Ile Ser Glu Gly Asp Ser Ile Lys Val Thr Val
            165                 170                 175

Glu Ala Thr Ser Lys Ser Ser Gly Ser Ala Thr Val Glu Asn Leu Thr
            180                 185                 190

Thr Gly Gln Ser Val Thr His Thr Phe Ser Gly Asn Val Glu Gly Asp
        195                 200                 205

Leu Cys Glu Thr Asn Ala Glu Trp Ile Val Glu Asp Phe Glu Ser Gly
        210                 215                 220

Asp Ser Leu Val Ala Phe Ala Asp Phe Gly Ser Val Thr Phe Thr Asn
225                 230                 235                 240

Ala Glu Ala Thr Ser Gly Gly Ser Thr Val Gly Pro Ser Asp Ala Thr
            245                 250                 255

Val Met Asp Ile Glu Gln Asp Gly Ser Val Leu Thr Glu Thr Ser Val
            260                 265                 270

Ser Gly Asp Ser Val Thr Val Thr Tyr Val
            275                 280
```

POLYPEPTIDES OF *ALICYCLOBACILLUS* SP. HAVING GLUTAMIC PEPTIDASE ACTIVITY

CROSS-REFERENCE TO RELATED APPLICATIONS

This application is a continuation of U.S. application Ser. No. 11/636,950 filed Dec. 11, 2006 (abandoned), which is a continuation-in-part of U.S. application Ser. No. 10/784,592 filed Feb. 23, 2004 (abandoned), which claims, under 35 U.S.C. 119, priority or the benefit of Danish application Nos. PA 2004 00010, filed Jan. 6, 2004, and PA 2004 00165, filed Feb. 4, 2004, the contents of which are fully incorporated herein by reference.

FIELD OF THE INVENTION

The present invention relates to functional polypeptides encoded by polynucleotides comprised in the genome of *Alicyclobacillus* sp. deposited under deposit accession number DSM 15716. The invention relates further to the polynucleotides and constructs of such polynucleotides encoding such polypeptides or facilitating their expression as well as to method for preparing the polypeptide. Still further the invention relates to compositions comprising the polypeptide and to uses of the polypeptide.

BACKGROUND OF THE INVENTION

Some enzymes from the genus of *Alicyclobacillus* species are known such as described in Matzke et al.; *Gene cloning, nucleotide sequence and biochemical properties of a cytoplasmic cyclomaltodexinase (neopullulanase) from Alicyclobacillus acidocalderius ATCC 2700; reclassification of a group of enzymes*; Submitted (MAR-1999) to the EMBL/GenBank/DDBJ databases or Kolvula et al.; *Cloning and sequencing of a gene encoding acidophilic amylase from Bacillus acidoceldarius*. J. Gen. Microbiol. 139:2399 (1993) or Bartolucci et al.; *Thioradoxin from Bacillus acidocaldarius: characterization, high-level expression in Escherichia coli and molecular modeling*; Biochem. J. 328:277 (1997) or Tsuruoka et al.; *Collagenolytic Serine-Carboxyl Proteinase from Alicyclobacillus sendainensis Strain NTAP-1: Purification, Characterization, Gene Cloning, and Heterologous Expression*; Submitted (MAY-2002) to the EMBL/GenBank/DDBJ databases; Eckert K. & Schneider E., *A thermoacidophilic endoglucanase (celB) from Alicyclobacillus acidocaldarius displays high sequence similarity to arabinofuranosidases belonging to family 51 of glycosyl hydrolases*, Eur. J. Biochem., 270: 3593-3602, 2003.

In the pursuit of novel enzymes it is also known to screen for such new enzymes by subjecting potential candidates to specific enzyme assays. This approach is limited to the availability of enzyme assays and does not allow the identification of functional enzymes or polypeptides for which the activity is still unknown.

Further, whole genome sequencing is a known method to obtain the information on all genes from a given microorganism e.g. as described in Fleischmann et al.; *Whole genome sequences and assembly of Haemophilus influenzae Rd*; Nature 269: 496-512; (1995).

Most enzymes for industrial use are enzymes which are secreted to the medium by a microorganism. However, only a few percent of a microorganisms' genome encodes secreted proteins. For example only approx. 4% of the *Bacillus subtilis* genome or its closest relatives encode secreted proteins (van Diji et al.: *Protein transport pathways in Bacillus subtilis: a genome-based road map*; in "*Bacillus subtilis* and its closest relatives,"—*From genes to cells*; p. 337-355; A. L. Sonenshein (ed.); ASM Press 2002).

One disadvantage of genome sequencing is that the vast majority of the obtained sequences encode non secreted proteins.

Also known is signal trapping which is a method to identify genes including nucleotides encoding a signal peptide using a translational fusion to an extra cellular reporter gene lacking its own signal (WO 01/77315).

SUMMARY OF THE INVENTION

The present inventors have found a strain of *Alicyclobacillus* namely *Alicyclobacillus* sp. DSM 15716 which grows at low pH (approx 4-5) and at high temperature (50-60° C.). This strain is interesting because the phylogenetic distance between the public known strains and strain DSM 15716 is significant and because the growth conditions are similar to conditions for several applications for industrial enzymes.

The genome of a microorganism contains thousands of different genes; some encoding polypeptides some coding for RNAs. Only a limited number of the genes in the genome of a microorganism encode functional polypeptides which are secreted by the microorganism to the surrounding medium serving an external purpose for the microorganism. Such polypeptides are interesting for industry from the point of view that such polypeptides may be produced in considerable amounts in continuous processes without destroying the cells producing the polypeptides.

It is an object of the present invention to Identify and provide polypeptides secreted from *Alicyclobacillus* sp. deposited under deposit accession number DSM 15716 which have functional purpose for the *Alicyclobacillus* sp. because such polypeptides may not only be used for Industrial purposes but they may also be produced in industrially relevant processes and amounts.

The present invention provides in a first aspect an Isolated polypeptide selected from the group consisting of:
(a) a polypeptide comprising an amino acid sequence which has at least 90% identity with a sequence of a mature polypeptide comprised in the group of SEQ ID NO: 26 to SEQ ID NO:50; and
(b) a polypeptide which is encoded by a nucleotide sequence which hybridize under high stringency conditions with a polynucleotide probe selected from the group consisting of
  (i) the complementary strand to a nucleotide sequence selected from the group of regions of SEQ ID NO: 1 to SEQ ID NO: 25 encoding a mature polypeptide.
  (ii) the complementary strand to the cDNA sequence contained in a nucleotide sequences selected from the group of regions of SEQ ID NO: 1 to SEQ ID NO: 25 encoding a mature polypeptide
wherein the polypeptide has a function of the corresponding mature polypeptides comprised in SEQ ID NO:26 to SEQ ID NO:50.

In a further aspect the invention provides an Isolated enzyme selected from the group consisting of:
(a) an enzyme comprising an amino acid sequence which has at least 90% identity with the amino acid sequence of a mature enzyme selected from the group consisting of acid endoglucanase or acid cellulase, aspartyl protease, mufti copper oxidase, serine-carboxyl protease, serine protease or HtrA-like serine protease, disulfide isomerase, gamma-D-glutamyl-L-diamino acid endopeptidase, endo-beta-N-acetylglucosaminidase, peptidyl-prolyl-isomerase, acid phosphatase or phytase or phospholipase C, polysaccharide deacetylase or xylan deacetylase and sulfite oxidase secreted from the strain of *Alicyclobacillus* sp. Deposited under DSM accession No. 15716

(b) a polypeptide which is encoded by a nucleotide sequence which hybridize under high stringency conditions with a polynucleotide probe selected from the group consisting of
  (i) the complementary strand to a nucleotide sequence comprised in the strain of *Alicyclobacillus* sp. Deposited under DSM accession No. 15716 encoding a mature enzyme selected from the group consisting of acid endoglucanase or acid cellulase, aspartyl protease, multi copper oxidase, serine-carboxyl protease, serine protease or HtrA-like serine protease, disulfide isomerase, gamma-D-glutamyl-L-diamino acid endopeptidase, endo-beta-N-acetylglucosaminidase, peptidyl-propyl-isomerase, acid phosphatase or phytase or phospholipase C, polysaccharide deacetylase or xylan deacetylase and sulfite oxidase secreted from that strain;
  (ii) the complementary strand to the cDNA sequence contained in a nucleotide sequences comprised in the strain of *Alicyclobacillus* sp. Deposited under DSM accession No. 15716 encoding a mature enzyme selected from the group consisting of acid endoglucanase or acid cellulase, aspartyl protease, multi copper oxidase, serine-carboxyl protease, serine protease or HtrA-like serine protease, disulfide isomerase, gamma-D-glutamyl-L-diamino acid endopeptidase, endo-beta-N-acetylglucosaminidase, peptidyl-prolyl-isomerase, acid phosphatase or phytase or phospholipase C, polysaccharide deacetylase or xylan deacetylase and sulfite oxidase secreted from that strain wherein the enzyme have a function selected from acid endoglucanase or acid cellulase, aspartyl protease, multi copper oxidase, serine-carboxyl-protease, serine protease or HtrA-like serine protease, disulfide isomerase, gamma-D-glutamyl-L-diamino acid endopeptidase, endo-beta-N-acetylglucosaminidase, peptidyl-prolyl-isomerase, acid phosphatase or phytase or phospholipase C, polysaccharide deacetylase or xylan deacetylase and sulfite oxidase In further aspects the invention provides a polynucleotide encoding the polypeptide of the invention; a nucleotide construct comprising the polynucleotide encoding the polypeptide, operably linked to one or more control sequences that direct the production of the polypeptide in a host cell; a recombinant expression vector comprising the nucleotide construct of the invention and to a recombinant host cell comprising the nucleotide construct of the invention.

In still further aspects the invention provides a method of preparing a polypeptide of the invention comprising:
(a) cultivating a strain comprising a nuclide sequence encoding a polypeptide of the Invention which strain is capable of expressing and secreting the polypeptide and
(b) recovering the polypeptide.

In still further aspects the invention provide a composition comprising a polypeptide of the invention and a method for preparing such a composition comprising admixing the polypeptide of the invention with an excipient.

In still further aspects the invention provides use of the polypeptide of the invention or a composition comprising said polypeptide in various applications.

Sequence Listing

The present application contains information in the form of a sequence listing, which is appended to the application and also submitted on a data carrier accompanying this application. The contents of the data carrier are fully incorporated herein by reference. The regions of SEQ ID NO: 1 to SEQ ID NO: 25 encoding a mature polypeptide encodes the mature polypeptides of SEQ ID NO:26 to SEQ ID NO:50. The region of SEQ ID NO: 1 encoding a mature polypeptide thus encodes the mature polypeptide sequence comprised in SEQ ID NO:26, the region of SEQ ID NO:2 encoding a mature polypeptide encode the mature polypeptide comprised in SEQ ID NO:27 and so on.

DETAILED DESCRIPTION OF THE INVENTION

Definitions

The term "Identity" as used herein, is to be understood as the homology between two amino acid sequences or between two nucleotide sequences. For purposes of the present invention, the degree of identity between two amino acid sequences was determined by using AlignX in the program of Vector NTI ver. 7.1 (Informax Inc., 7600 Wisconsin Avenue, Suite #1100, Bethesda, Md. 20814, USA). Amino acid alignment was created using the Clustal W algorithm (Nucleic Acid Research, 22 (22): 4673-4880, 1994). The following additional parameters are used: Gap opening penalty of 10, Gap extension penalty of 0.05, Gap separation penalty range of 8. Pairwise alignment parameters were Ktuple=1, gap penalty=3, gap length opening penalty a 10, gap extension penalty=0.1, window size=5 and diagonals=5. The degree of identity between two nucleotide sequences is determined using the same algorithm and software package as described above for example with the following settings: Gap penalty of 10, and gap length penalty of 10. Pairwise alignment parameters is Ktuple=3, gap panalty=3 and windows=20.

The term "functional polypeptide" as used herein in the context of the present invention means a polypeptide which can be expressed and secreted by a cell and which constitutes an operational unit capable of operating in accordance with the function it is designed to fulfil by the cell. Optionally, co-factors may be required for the polypeptide to adopt the Intended function. One example of functional polypeptides is catalytically active polypeptides or enzymes which help the cell catalyzing reactions in the environment surrounding the cell. Another example could be polypeptides which serve as signal substance. Further examples are polypeptides which function as sensors (receptors) for environmental parameters (chemicals in the environment surrounding the cell) or polypeptides, which are active against other organisms (antimicrobial (poly)peptides) or polypeptides, which contributes to the structural integrity of the cell.

The term "mature region" as used herein about portion of an amino acid sequences or polypeptide means the portion or region or domain or section of the amino acid sequences or polypeptide which is the mature functional polypeptide.

The term "region of nucleotide sequence encoding a mature polypeptide" as used herein means the region of a nucleotide sequence counting from the triplet encoding the first amino acid of a mature polypeptide to the last triplet encoding the last amino add of a mature polypeptide.

Polypeptides of the Invention

The polypeptides of the invention are polypeptides secreted by *Alicyclobacillus* sp. DSM 15716 with the purpose of serving a function for that particular cell and related polypeptides thereof.

Among the thousands of potential genes in the genome of *Alicyclobacillus* sp. DSM 15716 the polynucleotides of this genome encoded 25 secreted functional mature polypeptides comprised in SEQ ID NO: 26 to SEQ ID NO:50, which were determined to be functional, that is translated into functional polypeptides by the chosen host cell.

Accordingly, *Alicyclobacillus* sp. DSM 15716 expresses and secretes the functional mature polypeptides comprised in SEQ ID NO: 26 to SEQ NO: 50 and in the genome of that particular strain, the regions of SEQ ID NO: 1 to SEQ ID NO: 25 encoding a mature polypeptide are the genes encoding the mature polypeptides comprised in SEQ ID NO: 26 to SEQ NO: 50. Further in a particular embodiment the genes encoding the mature polypeptides comprised in of SEQ ID NO:26 to SEQ NO: 50 can all be expressed and their corresponding mature polypeptides can be secreted when culturing an *E. coli* host transformed with polynucleotides comprising those regions of SEQ ID NO: 1 to SEQ ID NO: 25 encoding a mature polypeptide. By comparing homology or identity of the sequences of the 25 polypeptide sequences to known sequences the particular function of the polypeptides were annotated. At least 15 of the 25 secreted functional polypeptides were determined to be enzymes.

The invention provides an isolated polypeptide selected from the group consisting of,
(a) a polypeptide having an amino acid sequence which has at least 90% identity with an amino acid sequence selected from the group consisting of the mature polypeptides comprised in SEQ ID NO: 26 to SEQ ID NO:50 and
(b) a polypeptide which is encoded by a nucleotide sequence which hybridize under high stringency conditions with a polynucleotide probe selected from the group consisting of
  (i) the complementary strand to a nucleotide sequence selected from the group consisting of regions of SEQ ID NO: 1 to SEQ ID NO: 25 encoding a mature polypeptide,
  (ii) the complementary strand to the cDNA sequence contained in a nucleotide sequences selected from regions of SEQ ID NO: 1 to SEQ ID NO: 25 encoding a mature polypeptide;
wherein the polypeptide exhibits the function of the corresponding mature polypeptide of SEQ ID NO: 26 to SEQ ID NO:50.

In one particular embodiment the polypeptide of the invention is selected among the enzymes secreted by *Alicyclobacillus* sp. deposited under DSM accession No. 15716 and isolated by the present inventors, i.e. the group of enzymes consisting of acid endoglucanase, acid cellulase, aspartyl protease, multi copper oxidase, serine-carboxyl protease serine protease, HtrA-like serine protease, disulfide Isomerase, gamma-D-glutamyl-L-diamino acid endopeptidase, endo-beta-N-acetylglucosaminidase, peptidyl-prolyl-isomerase, acid phosphatase, phytase, phospholipase C, polysaccharide deacetylase, xylan deacetylase and sulfite oxidase.

The invention also provides an isolated enzyme selected from the group consisting of:
(a) an enzyme comprising an amino acid sequence which has at least 90% identity with the amino acid sequence of a mature enzyme selected from the group consisting of acid endoglucanase or acid cellulase, aspartyl protease, multi copper oxidase, serine-carboxyl protease, serine protease or HtrA-like serine protease, disulfide isomerase, gamma-D-glutamyl-L-diamino acid endopeptidase, endo-beta-acetylglucosaminidase, peptidyl-prolyl-isomerase, acid phosphatase or phytase or phospholipase C, polysaccharide deacetylase or xylan deacetylase and sulfite oxidase secreted from the strain of *Alicyclobacillus* sp. Deposited under DSM accession No. 15716 and
(b) a polypeptide which is encoded by a nucleotide sequence which hybridize under high stringency conditions with a polynucleotide probe selected from the group consisting of
  (i) the complementary strand to a nucleotide sequence comprised in the strain of *Alicyclobacillus* sp. Deposited under DSM accession No. 15716 encoding a mature enzyme selected from the group consisting of acid endoglucanase or acid cellulase, aspartyl protease, mufti copper oxidase, serine-carboxyl protease, serine protease or HtrA-like serine protease, disulfide isomerase, gamma-D-glutamyl-L-diamino acid endopeptidase, endo-beta-N-acetylglucosaminidase, peptidyl-prolyl-isomerase, acid phosphatase or phytase or phospholipase C, polysaccharide deacetylase or xylan deacetylase and sulfite oxidase secreted from that strain;
  (ii) the complementary strand to the cDNA sequence contained in a nucleotide sequences comprised in the strain of *Alicyclobacillus* sp. Deposited under DSM accession No. 15716 encoding a mature enzyme selected from the group consisting of acid endoglucanase or acid cellulase, aspartyl protease, multi copper oxidase, serine-carboxyl protease, serine protease or HtrA-like serine protease, disulfide isomerase, gamma-D-glutamyl-L-diamino acid endopeptidase, endo-beta-N-acetylglucosaminidase, peptidyl-prolyl-isomerase, acid phosphatase or phytase or phospholipase C, polysaccharide deacetylase or xylan deacetylase and sulfite oxidase secreted from that strain and
wherein the enzyme have a function selected from acid endoglucanase or acid cellulase, aspartyl protease, multi copper oxidase, serine-carboxyl-protease, serine protease or HtrA-like serine protease, disulfide isomerase, gamma-D-glutamyl-L-diamino acid endopeptidase, endo-beta-N-acetylglucosaminidase, peptidyl-propyl-isomerase, acid phosphatase or phytase or phospholipase C, polysaccharide deacetylase or xylan deacetylase and sulfite oxidase.

In a particular embodiment the enzyme is an isolated enzyme selected from the group consisting of:
(a) an enzyme having an amino acid sequence which has at least 90% identity with an amino acid sequence selected from mature enzymes comprised in SEQ ID NO: 26 to SEQ ID NO:40 and
(b) an enzyme which is encoded by a nucleotide sequence which hybridize under high stringency conditions with a polynucleotide probe selected from the group consisting of
  (i) the complementary strand to a nucleotide sequence selected from the group of regions of SEQ ID NO: 1 to SEQ ID NO: 15 encoding the mature enzyme,
  (ii) the complementary strand to the cDNA sequence contained in a nucleotide sequences selected from regions of SEQ ID NO: 1 to SEQ ID NO: 15 encoding the mature polypeptide and
wherein the enzyme has a function of the corresponding mature polypeptides comprised in SEQ ID NO:26 to SEQ ID NO:40

The polypeptide of the invention is an Isolated polypeptide, preferably the preparation of the polypeptide of the invention contains at the most 90° h by weight of other polypeptide material with which it may be natively associated (lower percentages of other polypeptide material are preferred, e.g. at the most 80% by weight, at the most 60% by weight, at the most 50% by weight, at the most 40% at the most 30% by weight, at the most 20% by weight, at the most 10% by weight, at the most 9% by weight, at the most 8% by weight, at the most 6% by weight, at the most 5% by weight, at the most 4% at the most 3% by weight, at the most 2% by weight, at the most 1% by weight and at the most ½% by weight). Thus, it is preferred that the isolated polypeptide of the invention is at least 92% pure, i.e. that the polypeptide of the invention constitutes at least 92% by weight of the total polypeptide material present in the preparation, and higher percentages are preferred such as at least 94% pure, at least 95% pure, at least 98% pure, at least 96% pure, at least 97% pure, at least 98% pure, at least 99%, and at the most 99.5% pure. In particular, it is preferred that the polypeptide of the invention is in "essentially pure form", i.e. that the polypeptide preparation is essentially free of other polypeptide material with which it is natively associated. This can be accomplished, for example, by preparing the polypeptide of the invention by means of well-known recombinant methods.

The polypeptide of the invention of the invention may be synthetically made, naturally occurring or a combination thereof. In a particular embodiment the polypeptide of the invention may be obtained from a microorganism such as a prokaryotic cell, an archaeal cell or a eukaryotic cell. The cell may further have been modified by genetic engineering In a particular embodiment, the polypeptide of the Invention is an enzyme exhibiting optimum enzyme activity at a temperature within the range from about 10° C. to about 80° C. particularly in the range from about 20° C. to about 60° C.

In a particular embodiment the polypeptide of the invention is an enzyme, which is functionally stabile at a temperature of up to 100° C., in particular up to 80° C., more particularly up to 60° C.

In a particular embodiment the polypeptide of the invention is an enzyme exhibiting at least 20%, in particular at least 40%, such as at least 50%, in particular at least 60%, such as at least 70%, more particularly at least 80%, such as at least 90%, most particularly at least 95%, such as about or at least 100% of the enzyme activity of an enzyme selected from mature enzymes comprised in SEQ ID NO: 26 to SEQ ID NO: 50.

In a particular embodiment the polypeptide of the invention comprises, contains or consists of an amino acid sequence which has at least 900% identity with a polypeptide sequence selected from the group consisting of mature polypeptides comprised in SEQ ID NO: 26 to SEQ ID NO: 60; particularly at least 95%, e.g. at least 96%, such as at least 97%, and even more particularly at least 98%, such as at least 99% or even 100% identity.

In another particular embodiment the polypeptide of the invention comprises, contains or consists of an amino acid sequence, which has at least 50% identity with a polypeptide sequence selected from the group consisting of mature polypeptides comprised in SEQ ID NO: 26 to SEQ ID NO: 50; particularly at least 60%, particularly at least 65%, particularly at least 70%, particularly at least 75%, particularly at least 80%, and even more particularly at least 85% identity.

In a particular embodiment, the amino acid sequence of the polypeptide of the invention differs by at the most ten amino acids (e.g. by ten amino acids), in particular by at the most five amino acids (e.g. by five amino acids), such as by at the most four amino acids (e.g. by four amino acids), e.g. by at the most three amino acids (e.g. by three amino acids), in particular by at the most two amino acids (e.g. by two amino acids), such as by one amino acid from the mature polypeptides comprised in SEQ ID NO: 26 to SEQ ID NO: 50.

The polypeptide of the invention may be a wild-type polypeptide isolated from a natural source such as the strain *Alicyclobacillus* sp. DSM 15716 or another wild type strain, however the present invention also encompass artificial variants, where a polypeptide of the invention has been mutated for example by adding, substituting and/or deleting one or more amino acids from said polypeptide while retaining the function of the polypeptide and/or other properties. Hence, the polypeptide of the invention may be an artificial variant, wherein at least one substitution, deletion and/or insertion of an amino acid has been made to an amino acid sequence comprising or consisting of the mature polypeptide comprised in SEQ ID NO: 26 to SEQ ID NO: 50.

The polypeptides of the invention also include functional fragments of the amino acid sequences described herein and nucleic acids encoding functional fragments of the amino acid sequences described herein, including fragments of the mature enzymes secreted from the strain of *Alicyclobacillus* sp. Deposited under DSM accession No. 15716, as described herein, including fragment of an enzyme selected from the group consisting of acid endoglucanase, acid cellulase, aspartyl protease, multi copper oxidase, serine-carboxyl-protease, serine protease, HtrA-like serine protease, disulfide isomerase, gamma-D-glutamyl-L-diamino acid endopeptidase, endo-beta-N-acetylglucosaminidase, peptidyl-prolyl-isomerase, acid phosphatase, phytase, phospholipase C, polysaccharide deacetylase, xylan deacetylase and sulfite oxidase secreted from the strain of *Alicyclobacillus* sp. Deposited under DSM accession No. 15716.

Artificial variants may be constructed by standard techniques known in the art usually followed by screening and/or characterization. Standard techniques includes classical mutagenesis, e.g. by UV irradiation of the cells or treatment of cells with chemical mutagens as described by Gerhardt et al. (1994); in vivo gene shuffling as described in WO 97/07205; in vitro shuffling as described by Stemmer, (1994) or WO 95/17413, random mutagenesis as described by Eisenstadt E. et al., (1994); PCR techniques as described by Poulsen et al. (1991); family shuffling as described by J. E. Ness, et al, Nature Biotechnology, vol. 17, pp. 893-96 (1999); site-directed mutagenesis as described by Sambrook at al. (1989), Sambrook et al., Molecular Cloning, A Laboratory Manual, Cold Spring Harbor, N.Y. A general description of nucleotide substitution can be found in e.g. Ford et al., 1991, Protein Expression and Purification 2, p. 95-107.

Such standard genetic engineering methods may also be used prepare a diversified library of variant nucleotide sequences from the genes encoding one or more parent enzymes of the invention, expressing the enzyme variants in a suitable host cell and selecting a preferred variant(s). A diversified library can be established by a range of techniques known to the art (Reetz M T; Jaeger K E, in Biocatalysis—from Discovery to Application edited by Fessner W D, Vol. 200, pp. 31-57 (1999); Stemmer, Nature, vol. 370, p. 389-391, 1994; Zhao and Arnold, Proc. Natl. Acad. Sci., USA, vol. 94, pp. 7997-8000, 1997; or Yano et al., Proc. Natl. Aced. Sci., USA, vol. 95, pp 5511-5515, 1998).

In a particular embodiment of the invention, amino acid changes (in the artificial variant as well as in wild-type enzyme) are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine, valine and methionine), aromatic amino acids (phenylalanine, tryptophan and tyrosine), and small amino acids (glycine, alanine, serine and threonine). Amino acid substitutions which do not generally alter and or impair the function of a protein are known in the art and are described, for example, by H. Neurath and R. L Hill, 1979, in, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In a particular embodiment the amino acid changes are of such a nature that the physico-chemical properties of the polypeptides are altered. For example, amino acid changes may be performed, which improve the thermal stability of the enzyme, which alter the substrate specificity, which changes the pH optimum, and the like.

Particularly, the number of such substitutions, deletions and/or insertions in the polypeptide of the invention, particularly in those polypeptides selected from the group consisting of mature polypeptides comprised in SEQ ID NO: 26 to SEQ ID NO: 50 to produce an artificial variant is at the most 10, such as at the most 9, e.g. at the most 8, more preferably at the most 7, e.g. at the most 6, such as at the most 5, most preferably at the most 4, e.g. at the most 3, such as at the most 2, in particular at the most 1.

In a particular embodiment the artificial variant is a variant, which has an altered, preferably reduced, immunogenicity, especially allergenicity, in animals including man as compared to a parent enzyme. The term "immunogenicity" in this context is to be understood as the artificial variant capability of invoking a an altered, in particular reduced, immunological response when administered to an animal, including intravenous, cutaneous, subcutaneous, oral and intratracheal administration. The term "immunological response" in this context means that the administration of the artificial variant causes an alteration in the immunoglobulin levels in the animal body, such as in IgE, IgG and IgM or an alteration in the cytokine level in the animal body. Methods for mapping immunogenic/antigenic epitopes of a protein, preparing variants with altered immunogenicity and methods for measuring an immunological response is well known to the art and are described e.g. in WO 92/10755, WO 00/26230, WO 00/26354 and WO 01/31989, The term "allergenicity" in this context is to be understood as the artificial variant ability of invoking an altered, in particular reduced, production of IgE in an animal as well as the ability to bind IgE from said animal. Particularly allergenicity arising from intratracheal administration of the polypeptide variant to the animal is particularly of interest (also known as respiratory allergenicity).

In a further embodiment, the polypeptide of the invention is a polypeptide which is encoded by nucleotide sequences which hybridize under at least high stringency conditions, particularly under very high stringency conditions with a polynucleotide probe selected from the group consisting of
(i) the complementary strand to a nucleotide sequence selected from the group of regions of SEQ ID NO: 1 to SEQ ID NO: 25 encoding a mature polypeptide,
(ii) the complementary strand to the cDNA sequence contained in a nucleotide sequences selected from regions of SEQ ID NO: 1 to SEQ ID NO: 25 encoding a mature polypeptide
(iii) a fragment of (i) or (ii) encoding a secreted polypeptide having the function of the corresponding mature polypeptide comprised in SEQ ID NO: 26 to SEQ ID NO: 50
(J. Sambrook, E. F. Fritsch, and T. Maniatus, 1989, Molecular Cloning, A Laboratory Manual, 2d edition, Cold Spring Harbor, N.Y.).

In particular, the polypeptide of the invention is encoded by a polynucleotide comprising a nucleotide sequence selected from the group of regions of SEQ ID NO: 1 to SEQ ID NO: 25 encoding a mature polypeptide or a sequences differing there from by virtue of the degeneracy of the genetic code. More particularly, the polypeptide of the invention is encoded by a polynucleotide consisting of a nucleotide sequence selected from the group of regions of SEQ ID NO: 1 to SEQ ID NO: 25 encoding a mature polypeptide or a sequence differing there from by virtue of the degeneracy of the genetic code.

The nucleotide sequences of regions of SEQ ID NO: 1 to SEQ ID NO: 25 encoding a mature polypeptide or a subsequence thereof, as well as the amino acid sequences of the mature polypeptides comprised in SEQ 10 NO: 26 to SEQ ID NO: 50 or a fragment thereof, may be used to design a polynucleotide probe to identify and clone DNA encoding enzymes of the invention from strains of different genera or species according to methods well known in the art in particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, more preferably at least 35 nucleotides in length, such as at least 70 nucleotides in length. It is; however, preferred that the polynucleotide probe is at least 100 nucleotides in length. For example, the polynucleotide probe may be at least 200 nucleotides in length, at least 300 nucleotides in length, at least 400 nucleotides in length or at least 500 nucleotides in length. Even longer probes may be used, e.g., polynucleotide probes which are at least 600 nucleotides in length, at least 700 nucleotides in length, at least 800 nucleotides in length, or at least 900 nucleotides in length. Both DNA and RNA probes can be used. The probes are typically labelled for detecting the corresponding gene (for example, with $^{32}P$, $^{3}H$, $^{35}S$, biotin, or avidin).

Thus, a genomic DNA or cDNA library prepared from such other organisms may be screened for DNA, which hybridizes with the probes described above and which encodes enzymes of the invention. Genomic or other DNA from such other organisms may be separated by agarose or polyacrylamide gel electrophoresis, or other separation techniques. DNA from the libraries or the separated DNA may be transferred to, and immobilized, on nitrocellulose or other suitable carrier materials. In order to identify a done or DNA which has the required homology and/or identity or is homologous and/or identical with of nucleotides selected from regions of SEQ ID NO: 1 to SEQ ID NO: 25 encoding a mature polypeptide, the carrier material with the immobilized DNA is used in a Southern blot.

For purposes of the present invention, hybridization indicates that the nucleotide sequence hybridizes to a labelled polynucleotide probe which again hybridizes to a nucleotide sequence selected from regions of SEQ ID NO: 1 to SEQ ID NO: 25 encoding a mature polypeptide under high to very high stringency conditions. Molecules to which the polynucleotide probe hybridizes under these conditions may be detected using X-ray film or by any other method known in the art. Whenever the term "polynucleotide probe" is used in the present context, it is to be understood that such a probe contains at least 15 nucleotides.

In an interesting embodiment, the polynucleotide probe is the complementary strand of a nucleotide sequence selected from regions of SEQ ID NO: 1 to SEQ ID NO: 25 encoding a mature polypeptide.

In another interesting embodiment, the polynucleotide probe is the complementary strand of a nucleotide sequence which encodes an enzyme selected from the group of SEQ ID NO: 26 to SEQ ID NO: 50. In a further interesting embodiment, the polynucleotide probe is the complementary strand of a mature polypeptide coding region of a nucleotide sequence selected from regions of SEQ ID NO: 1 to SEQ ID NO: 25 encoding a mature polypeptide.

For long probes of at least 100 nucleotides in length, high to very high stringency conditions are defined as pre-hybridization and hybridization at 42° C. in 5×SSPE, 1.0% SDS, 5×Denhardt's solution, 100 microgram/ml sheared and denatured salmon sperm DNA, following standard Southern blotting procedures. Preferably, the long probes of at least 100 nucleotides do not contain more than 1000 nucleotides. For long probes of at least 100 nucleotides in length, the carrier material is finally washed three times each for 15 minutes using 0.1×SSC, 0.1% SDS at 60° C. (high stringency), in particular washed three times each for 15 minutes using 0.1× SSC, 0.1% SDS at 68° C. (very high stringency).

Although not particularly preferred, it is contemplated that shorter probes, e.g. probes which are from about 15 to 99 nucleotides in length, such as from about 15 to about 70 nucleotides in length, may be also be used. For such short probes, stringency conditions are defined as pre-hybridization, hybridization, and washing post-hybridization at 5° C. to 10° C. below the calculated Tm using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to 99 nucleotides in length, the carrier material is washed once in 6×SCC plus 0.1% SDS for 15 minutes and twice each for 15 minutes using 6×SSC at 5° C. to 10° C. below the calculated Tm.

SEQ ID NO: 26 Acid Endoglucanase or Acid Cellulose

In a particular embodiment the polypeptide of the invention is an add endoglucanase or add cellulase comprising or consisting of an amino add sequence which has at least 90%, particularly at least 95%, more particularly at least 96%, more particularly at least 97%, more particularly at least 98%, more particularly at least 99% or most particularly 100% identity with an acid endoglucanase or acid cellulase obtainable from *Alicyclobacillus* sp., in particular that strain of *Alicyclobacillus* sp. Deposited under DSM accession No. 15716, more particularly the mature acid endoglucanase or acid cellulose comprised in SEQ ID NO: 26. More specifically the mature add endoglucanase or add cellulase comprise or consists of the sequences from position 25 to 959 of SEQ 10 NO: 26. In the present context an acid endoglucanase is defined as enzyme, which endohydrolyzes 1,4-beta-D-glucosidic linkages in cellulose, lichenin or cereal beta-D-glucans particularly at acidic conditions. In the present context an acid cellulose is defined as enzyme, which endohydrolyzes 1,4-beta-D-glucosidic linkages in cellulose, particularly at acidic conditions.

SEQ ID NO: 27 Aspartyl Protease

In a particular embodiment the polypeptide of the invention is an aspartyl protease comprising or consisting of an amino acid sequence which has at least 90%, particularly at least 95%, more particularly at least 96%, more particularly at least 97%, more particularly at least 98%, more particularly at least 99% or most particularly 100% identity with an aspartyl protease obtainable from *Alicyclobacillus* sp., in particular that strain of *Alicyclobacillus* sp. Deposited under DSM accession No. 15716, more particularly the mature aspartyl protease comprised in SEQ ID NO: 27. More specifically the mature aspartyl protease comprises or consists of the sequences from position 33 to 272 of SEQ ID NO: 27. In the present context an aspartyl protease is defined as defined as an enzyme, which hydrolyses proteins or peptides, and which contains two aspartyl residues in the catalytic site.

Surprisingly, the aspartyl protease comprised in SEQ ID NO: 27 is the first isolated aspartyl protease, in particular family A4 protease, isolated from a bacterium. Furthermore, surprisingly this aspartyl protease differs from known fungal aspartyl proteases by the absence of disulphide bridges in the molecule. The aspartyl protease comprised in SEQ ID NO: 27 contains only one Cystein and thus no disulphide bridges in the protease structure as compared to e.g. SEQ ID NO: 55 disclosing a known fungal aspartyl protease, which are composed of two peptides cross linked by 2 disulphide bridges. Hence, the aspartyl protease of *Alicyclobacillus* sp. specifically that deposited under DSM accession No. 15716 a second propeptide is missing and thus requires one less maturation step less in its production. This is an advantage for the cellular production. Family A4 proteases are known to the art as proteases having an Asp/Asp Asp/Glu configuration in the active site.

SEQ ID NO: 28 or SEQ ID NO:35 Multi Copper Oxidase

In a particular embodiment the polypeptide of the invention is a multi copper oxidase comprising or consisting of an amino acid sequence which has at least 90%, particularly at least 95%, more particularly at least 96%, more particularly at least 97%, more particularly at least 98%, more particularly at least 99% or most particularly 100% identity with multi copper oxidase obtainable from *Alicyclobacillus* sp., in particular that strain of *Alicyclobacillus* sp. Deposited under DSM accession No. 15716, more particularly the mature multi copper oxidase comprised in SEQ ID NO: 28 or 35. More specifically the mature multi copper oxidase comprises or consists of the sequences from position 26 to 315 of SEQ ID NO: 28 or position 50 to 597 of SEQ ID NO: 35. In the present context a multi-Cu-oxidase is defined as a protein, which possesses at least three spectroscopically different copper centers. Multicopper oxidases can be laccases that oxidizes many different types of phenols and diamines, ascorbate oxidases, ceruloplasmin, that oxidizes a great variety of inorganic and organic substances or part of proteins that have lost the ability to bind copper and thereby mediate heavy metal resistance by sequestration of the heavy metal in the periplasm of the bacterium.

SEQ ID NO: 29 or SEQ ID NO: 30 Serine-Carboxyl Protease

In a particular embodiment the enzyme of the invention is a serine-carboxyl protease comprising or consisting of an amino add sequence which has at least 90%, particularly at least 95%, more particularly at least 96%, more particularly at least 97%, more particularly at least 98%, more particularly at least 99% or most particularly 100% identity with the serine-carboxyl protease obtainable from *Alicyclobacillus* sp., in particular that strain of *Alicyclobacillus* sp. Deposited under DSM accession No. 15716, more particularly the mature serine-carboxyl protease comprised in SEQ ID NO: 29 or 30. More specifically the mature serine-carboxyl protease comprises or consists of the sequences from position 190 to 626 of SEQ ID NO: 29 or position 25 to 533 of SEQ ID NO: 30. In the present context a serine-carboxyl protease is defined as a protease belonging to the Enzyme class EC 3.4.21.100 (pseudomonapepsin) which proteolytic enzymes fold resembles that of subtilisin, with a unique catalytic triad, Ser-Glu-Asp, as well as the presence of an aspartic acid residue in the oxyanion hole. A polypeptide sequence can be classified as a serine-carboxyl peptidase, if the amino acids of the catalytic site are present in the sequence and if it shows peptide sequence similarity to peptide sequences in MEROPS serine protease family 53.

SEQ ID NO: 31 Serine Protease or a HtrA-Like Serine Protease

In a particular embodiment the polypeptide of the invention is a serine protease or a HtrA-like serine protease comprising or consisting of an amino acid sequence which has at least 90%, particularly at least 95%, more particularly at least 96%, more particularly at least 97%, more particularly at least 98%, more particularly at least 99% or most particularly 100% identity with the serine protease or the HtrA-like serine protease obtainable from Alicyclobacillus sp., in particular that strain of Alicyclobacillus sp. Deposited under DSM accession No. 15716, more particularly the mature serine protease carboxyl protease comprised in SEQ ID NO: 31. More specifically the mature serine protease comprises or consists of the sequences from position 42 to 411 of SEQ ID NO: 31. In the present context a serine protease is defined as an enzyme, which hydrolyses proteins or peptides, and which contains a serine residue in the catalytic site. A HtrA-like protease is defined as an enzyme that degrades damaged proteins in the extra cellular compartment of a bacterial cell at elevated temperatures.

SEQ ID NO: 32 Disulfide Isomerase

In a particular embodiment the polypeptide of the invention is a disulfide isomerase comprising or consisting of an amino acid sequence which has at least 90%, particularly at least 95%, more particularly at least 96%, more particularly at least 97%, more particularly at least 98%, more particularly at least 99% or most particularly 100% identity with the disulfide isomerase obtainable from Alicyclobacillus sp., in particular that strain of Alicyclobacillus sp. Deposited under DSM accession No. 15716, more particularly the mature disulfide isomerase comprised in SEQ ID NO: 32. More specifically the mature disulfide isomerase comprises or consists of the sequences from position 31 to 212 of SEQ ID NO: 32. In the present context a disulfide isomerase is defined as enzyme, which catalyses the rearrangement of both intrachain and interchain disulfide bonds in proteins to form the native structures.

SEQ ID NO:33 Gamma-D-glutamyl-L-diamino Acid Endopeptidase

In a particular embodiment the polypeptide of the invention is a gamma-D-glutamyl-L-diamino acid endopeptidase comprising or consisting of an amino acid sequence which has at least 90%, particularly at least 95%, more particularly at least 98%, more particularly at least 97%, more particularly at least 98%, more particularly at least 99% or most particularly 100% identity with the gamma-D-glutamyl-L-diamino acid endopeptidase obtainable from Alicyclobacillus sp., in particular that strain of Alicyclobacillus sp. Deposited under DSM accession No. 15716, more particularly the mature gamma-D-glutamyl-diamino acid endopeptidase comprised in SEQ ID NO: 33. More specifically the mature gamma-D-glutamyl-L-diamino acid endopeptidase comprises or consists of the sequences from position 30 to 266 of SEQ ID NO: 33. In the present 30 context a gamma-D-glutamyl-L-diamino acid endopeptidase is defined as an enzyme that hydrolyses gamma-glutamyl bonds to (L) meso-diaminopimelic acid in L-Ala-gamma-D-Glu-l-(L)meso-diaminopimelic acid-L)-D-Ala. It is required that the omega-amino and omega-carboxyl groups of the (L) meso-diaminopimelic acid group are unsubstituted.

SEQ ID NO: 34 Endo-beta-N-acetylglucosaminidase

In a particular embodiment the polypeptide of the invention is an endo-beta-N-acetylglucosaminidase comprising or consisting of an amino acid sequence which has at least 90%, particularly at least 95%, more particularly at least 96%, more particularly at least 97%, more particularly at least 98%, more particularly at least 99% or most particularly 100% identity with the endo-beta-N-acetylglucosaminidase obtainable from Alicyclobacillus sp., in particular that strain of Alicyclobacillus sp. Deposited under DSM accession No. 15716, more particularly the mature endo-bets-N-acetylglucosaminidase comprised in SEQ ID NO: 34. More specifically the mature endo-beta-N-acetylglucosaminidase comprises or consists of the sequences from position 27 to 768 of SEQ ID NO: 34. In the present context an endo-beta-N-Acetylglucosaminidase is defined as enzyme that hydrolyses the 1,4beta-linkages between N-acetyl-D-glucosamine and N-acetylmuramic acid in peptidoglycan heteropolymers of the prokaryotes cell walls.

SEQ ID NO:36 Peptidyl-prolyl-isomerase

In a particular embodiment the polypeptide of the invention is a peptidyl-prolyl-isomerase comprising or consisting of an amino add sequence which has at least 90%, particularly at least 95%, more particularly at least 96%, more particularly at least 97%, more particularly at least 98%, more particularly at least 99% or most particularly 100% identity with the peptidyl-prolyl-isomerase obtainable from Alicyclobacillus sp., in particular that strain of Alicyclobacillus sp. Deposited under DSM accession No. 15716, more particularly the mature peptidyl-prolyl-isomerase comprised in SEQ ID NO: 38. More specifically the mature peptidyl-prolyl-isomerase comprises or consists of the sequences from position 30 to 246 of SEQ ID NO: 36. In the present context a peptidyl-prolyl-isomerase is defined as an enzyme that accelerates protein folding by catalyzing the cis-trans isomerization of proline imidic peptide bonds in oligopeptides.

SEQ ID NO: 37 Acid Phosphatase or a Phytase or a Phospholipase C

In a particular embodiment the polypeptide of the invention is an acid phosphatase or a phytase or a phospholipase C comprising or consisting of an amino acid sequence which has at least 90%, particularly at least 95%, more particularly at least 96%, more particularly at least 97%, more particularly at least 98%, more particularly at least 99% or most particularly 100% identity with the acid phosphatase or phytase or phospholipase C obtainable from Alicyclobacillus sp., in particular that strain of Alicyclobacillus sp. Deposited under DSM accession No. 15716, more particularly the mature acid phosphatase or phytase or phospholipase C comprised in SEQ ID NO: 37. More specifically the mature acid phosphatase or a phytase or a phospholipase C comprises or consists of the sequences from position 28 to 608 of SEQ ID NO: 37. An acid phosphatase is defined as enzyme hydrolyzing an orthophosphoric monoester into an alcohol and phosphate. In the present context a phytase is defined as an enzyme removing a phosphate group from phytate. A phospholipase C is defined as an enzyme hydrolyzing phosphatidylcholine into 1,2-diacylglycerol and choline.

SEQ ID NO: 38 or SEQ ID NO: 39 Polysaccharide Deacetylase

In a particular embodiment the polypeptide of the invention is a polysaccharide deacetylase or a xylan deacetylase comprising or consisting of an amino add sequence which has at least 90%, particularly at least 95%, more particularly at least 96%, more particularly at least 97%, more particularly at least 98%, more particularly at least 99% or most particularly 100% identity with the polysaccharide deacetylase or the xylan deacetylase obtainable from Alicyclobacillus sp., in particular that strain of Alicyclobacillus sp. Deposited under DSM accession No. 15716, more particularly the mature polysaccharide deacetylase or a xylan deacetylase comprised in SEQ ID NO: 38 or 39. More specifically the mature polysaccharide deacetylase or a xylan deacetylase comprises or consists of the sequences from position 28 to 251 of SEQ ID NO: 38 or position 22 to 324 of SEQ ID NO: 39. In the present context a polysaccharide deacetylase is defined as an enzyme, which removes acetyl residues from a specific acetylated polysaccharide by hydrolysis. A xylan deacetylase is defined as an enzyme removing acetyl groups from acetylated xylan.

SEQ ID NO:40 Sulfite Oxidase

In a particular embodiment the polypeptide of the invention is a sulfite oxidase comprising or consisting of an amino acid sequence which has at least 90%, particularly at least 95%, more particularly at least 98%, more particularly at least 97%, more particularly at least 98%, more particularly at least 99% or most particularly 100% identity with the sulfite oxidase obtainable from *Alicyclobacillus* sp., in particular that strain of *Alicyclobacillus* sp. Deposited under DSM accession No. 15716, more particularly the mature sulfite oxidase comprised in SEQ ID NO: 40. More specifically the mature sulfite oxidase comprises or consists of the sequences from position 30 to 214 of SEQ ID NO: 40. A sulfite oxidase is defined as enzyme that oxidizes sulfite to sulfate.

SEQ ID NO:41 Functional Polypeptide

In a particular embodiment the polypeptide of the invention is a functional polypeptide comprising or consisting of an amino acid sequence which has at least 90%, particularly at least 95%, more particularly at least 96%, more particularly at least 97%, more particularly at least 98%, more particularly at least 99% or most particularly 100% identity with SEQ ID NO:41. In particular with the mature functional polypeptide comprised in SEQ ID NO: 41. More specifically the mature functional polypeptide comprises or consists of the sequences from position 22 to 257 of SEQ ID NO: 41.

SEQ ID NO:42 Functional Polypeptide

In a particular embodiment the polypeptide of the invention is a functional polypeptide comprising or consisting of an amino add sequence which has at least 90%, particularly at least 95%, more particularly at least 986%, more particularly at least 97%, more particularly at least 98%, more particularly at least 99% or most particularly 100% identity with SEQ ID NO:42. In particular with the mature functional polypeptide comprised in SEQ ID NO: 42. More specifically the mature functional polypeptide comprises or consists of the sequences from position 25 to 1130 of SEQ ID NO: 42.

SEQ ID NO:43 Functional Polypeptide

In a particular embodiment the polypeptide of the invention is a functional polypeptide comprising or consisting of an amino acid sequence which has at least 90%, particularly at least 95%, more particularly at least 96%, more particularly at least 97%, more particularly at least 98%, more particularly at least 99% or most particularly 100% identity with SEQ ID NO:43. In particular with the mature functional polypeptide comprised in SEQ ID NO: 43. More specifically the mature functional polypeptide comprises or consists of the sequences from position 42 to 248 of SEQ ID NO: 43.

SEQ ID NO:44 Functional Polypeptide

In a particular embodiment the polypeptide of the invention is a functional polypeptide comprising or consisting of an amino acid sequence which has at least 90%, particularly at least 95%, more particularly at least 96%, more particularly at least 97%, more particularly at least 98%, more particularly at least 99% or most particularly 100% identity with SEQ ID NO:44. In particular with the mature functional polypeptide comprised in SEQ ID NO: 44. More specifically the mature functional polypeptide comprises or consists of the sequences from position 26 to 172 of SEQ ID NO: 44.

SEQ ID NO:45 Functional Polypeptide

In a particular embodiment the polypeptide of the invention is a functional polypeptide comprising or consisting of an amino acid sequence which has at least 90%, particularly at least 95%, more particularly at least 99%, more particularly at least 97%, more particularly at least 98%, more particularly at least 99% or most particularly 100% identity with SEQ ID NO:45. In particular with the mature functional polypeptide comprised in SEQ ID NO: 45. More specifically the mature functional polypeptide comprises or consists of the sequences from position 31 to 242 of SEQ ID NO: 45.

SEQ ID NO:46 Functional Polypeptide

In a particular embodiment the polypeptide of the invention is a functional polypeptide comprising or consisting of an amino acid sequence which has at least 90% h, particularly at least 95%, more particularly at least 96%, more particularly at least 97%, more particularly at least 98%, more particularly at least 99% or most particularly 100% identity with SEQ ID NO:46. In particular with the mature functional polypeptide comprised in SEQ ID NO: 46. More specifically the mature functional polypeptide comprises or consists of the sequences from position 25 to 280 of SEQ ID NO: 46.

SEQ ID NO:47 Functional Polypeptide

In a particular embodiment the polypeptide of the invention is a functional polypeptide comprising or consisting of an amino acid sequence which has at least 90%, particularly at least 95%, more particularly at least 96%, more particularly at least 97%, more particularly at least 98%, more particularly at least 99% or most particularly 100% identity with SEQ ID NO:47. In particular with the mature functional polypeptide comprised in SEQ ID NO: 47. More specifically the mature functional polypeptide comprises or consists of the sequences from position 26 to 478 of SEQ ID NO: 47.

SEQ ID NO:48 Functional Polypeptide

In a particular embodiment the polypeptide of the invention is a functional polypeptide comprising or consisting of an amino acid sequence which has at least 90%, particularly at least 95%, more particularly at least 96%, more particularly at least 97%, more particularly at least 98%, more particularly at least 99% or most particularly 100% identity with SEQ ID NO: 48. In particular with the mature functional polypeptide comprised in SEQ ID NO: 48. More specifically the mature functional polypeptide comprises or consists of the sequences from position 20 to 340 of SEQ ID NO: 48.

SEQ ID NO:49 Functional Polypeptide

In a particular embodiment the polypeptide of the invention is a functional polypeptide comprising or consisting of an amino acid sequence which has at least 90%, particularly at least 95%, more particularly at least 96%, more particularly at least 97%, more particularly at least 98%, more particularly at least 99% or most particularly 100% identity with SEQ ID NO: 49. In particular with the mature functional polypeptide comprised in SEQ ID NO: 49. More specifically the mature functional polypeptide comprises or consists of the sequences from position 30 to 341 of SEQ ID NO: 49.

SEQ ID NO, 50 Functional Polypeptide

In a particular embodiment the polypeptide of the invention is a functional polypeptide comprising or consisting of an amino acid sequence which has at least 90%, particularly at least 95%, more particularly at least 98%, more particularly at least 97%, more particularly at least 98%, more particularly at least 99% or most particularly 100% identity with SEQ ID NO: 50. In particular with the mature functional polypeptide comprised in SEQ ID NO: 50. More specifically the mature functional polypeptide comprises or consists of the sequences from position 29 to 400 of SEQ ID NO: 50.

Polynucleotides

The present invention also relates to polynucleotides comprising or consisting of a nucleotide sequence encoding a polypeptide of the invention. In a particular embodiment, the nucleotide sequence is set forth in SEQ ID NO: 1 to SEQ ID NO: 25 including nucleotide sequences differing there from by virtue of the degeneracy of the genetic code. In a further embodiment the polynucleotide of the invention is a modified nucleotide sequence which comprises or consists of a nucleotides sequence selected from the regions of SEQ ID NO: 1 to SEQ ID NO: 25 encoding a mature polypeptide and which comprises at least one modification/mutation compared with the parent nucleotide sequence comprised in SEQ ID NO: 1 to SEQ ID NO: 25.

The techniques used to isolate and/or clone a nucleotide sequence encoding an enzyme are known in the art and include isolation from genomic DNA, preparation from cDNA, or a combination thereof. The cloning of the nucleotide sequences of the present invention from such genomic DNA can be effected, e.g., by using the well known polymerase chain reaction (PCR) or antibody screening of expression libraries to detect cloned DNA fragments with shared structural features. See, e.g., Innis at al., 1990, *PCR: A Guide to Methods and Application*, Academic Press, New York. Other amplification procedures such as ligase chain reaction (LCR), ligated activated transcription (LAT) and nucleotide sequence-based amplification (NASBA) may be used.

The nucleotide sequence may be obtained by standard cloning procedures used in genetic engineering to relocate the nucleotide sequence from its natural location to a different site where it will be reproduced. The cloning procedures may involve excision and isolation of a desired fragment comprising the nucleotide sequence encoding the polypeptide, insertion of the fragment into a vector molecule, and incorporation of the recombinant vector into a host cell where multiple copies or clones of the nucleotide sequence will be replicated. The nucleotide sequence may be of genomic, cDNA, RNA, semi-synthetic, synthetic origin, or any combinations thereof.

In particular the polynucleotide comprises, preferably consists of, a nucleotide sequence which has at least 50% identity with a nucleotide sequence selected from the regions of SEQ ID NO: 1 to SEQ ID NO: 25 encoding a mature polypeptide. Particularly, the nucleotide sequence has at least 65% identity, more particularly at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with a nucleotide sequence selected from the regions of SEQ ID NO: 1 to SEQ ID NO: 25 encoding a mature polypeptide. Particularly, the nucleotide sequence comprises a nucleotide sequence selected from the regions of SEQ ID NO: 1 to SEQ ID NO: 25 encoding a mature polypeptide. In an even more particular embodiment, the nucleotide sequence consists of a nucleotide sequence selected from the regions of SEQ ID NO: 1 to SEQ ID NO: 25 encoding a mature polypeptide.

In particular the polynucleotide comprises, preferably consists of, a nucleotide sequence which has at least 50% identity, particularly at least 85% identity, more particularly at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with a nucleotide sequence encoding a mature enzyme selected from acid endoglucanase or acid cellulase, aspartyl protease, multi copper oxidase, serine-carboxyl protease, serine protease or HtrA-like serine protease, disulfide isomerase, gamma-D-glutamyl-L-diamino acid endopeptidase, endo-beta-N-acetylglucosaminidase, peptidyl-prolyl-isomerase, acid phosphatase or phytase or phospholipase C, polysaccharide deacetylase or xylan deacetylase and sulfite oxidase secreted from the strain of *Alicyclobacillus* sp. Deposited under DSM accession No. 15716

SEQ ID NO: 1

In a particular embodiment the polynucleotide of the invention encodes an acid endoglucanase or acid cellulase and comprises or consists of an nucleotide sequence which has at least 70% h identity, more particularly at least 60% identity, more particularly at least 90% identity, more particularly at least 95% identity, more particularly at least 98% identity, more particularly at least 97% identity, more particularly at least 98% identity, more particularly at least 99% identity or most particularly 100% identity with the nucleotide sequence of position 73 to 2877 of SEQ ID NO: 1

SEQ ID NO: 2

In a particular embodiment the polynucleotide of the invention encodes an aspartyl protease and comprises or consists of an nucleotide sequence which has at least 70% identity, more particularly at least 80% identity, more particularly at least 90% identity, more particularly at least 95% identity, more particularly at least 98% identity, more particularly at least 97% identity, more particularly at least 98% identity, more particularly at least 99% identity or most particularly 100% identity with the nucleotide sequence of position 97 to 816 of SEQ ID NO: 2

SEQ ID NO: 3 and 10

In a particular embodiment the polynucleotide of the invention encodes an multi copper oxidase and comprises or consists of an nucleotide sequence which has at least 70% identity, more particularly at least 80% identity, more particularly at least 90% identity, more particularly at least 95% identity, more particularly at least 98% identity, more particularly at least 97% identity, more particularly at least 98% identity, more particularly at least 99% identity or most particularly 100% identity with the nucleotide sequence of position 76 to 945 of SEQ ID NO: 1 or 148 to 1791 of SEQ ID NO: 10

SEQ ID NO:4 and 5

In a particular embodiment the polynucleotide of the invention encodes a serine-carboxyl protease and comprises or consists of an nucleotide sequence which has at least 70% identity, more particularly at least 50% identity, more particularly at least 90% identity, more particularly at least 95% identity, more particularly at least 95% identity, more particularly at least 97% identity, more particularly at least 98% identity, more particularly at least 99% identity or most particularly 100% identity with the nucleotide sequence of position 588 to 1878 of SEQ ID NO: 4 or 73 to 1599 of SEQ ID NO: 5.

SEQ ID NO: 6

In a particular embodiment the polynucleotide of the invention encodes a serine protease or a HtrA-like serine protease and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 124 to 1233 of SEQ ID NO: 6.

SEQ ID NO: 7

In a particular embodiment the polynucleotide of the invention encodes a disulfide isomerase and comprises or consists of an nucleotide sequence which has at least 70% identity, more particularly at least 80% identity, more particularly at least 909 identity, more particularly at least 95% identity, more particularly at least 96% identity, more particularly at least 97% identity, more particularly at least 98% identity, more particularly at least 99% identity or most particularly 100% identity with the nucleotide sequence of position 91 to 633 of SEQ ID NO: 7.

SEQ ID NO: 8

In a particular embodiment the polynucleotide of the invention encodes a gamma-D-glutamyl-L-diamino acid endopeptidase and comprises or consists of an nucleotide sequence which has at least 70% identity, more particularly at least 80% identity, more particularly at least 90% identity, more particularly at least 95% identity, more particularly at least 98% identity, more particularly at least 97% identity, more particularly at least 98% identity, more particularly at least 99% identity or most particularly 100% identity with the nucleotide sequence of position 88 to 798 of SEQ ID NO: 8.

SEQ ID NO: 9

In a particular embodiment the polynucleotide of the invention encodes a endo-beta-N-acetylglucosaminidase and comprises or consists of an nucleotide sequence which has at least 70% identity, more particularly at least 80% identity, more particularly at least 90% identity, more particularly at least 95% identity, more particularly at least 98% identity, more particularly at least 97% identity, more particularly at least 98% identity, more particularly at least 99% identity or most particularly 100% identity with the nucleotide sequence of position 79 to 2304 of SEQ ID NO: 9.

SEQ ID NO: 11

In a particular embodiment the polynucleotide of the invention encodes a peptidyl-prolyl-isomerase and comprises or consists of an nucleotide sequence which has at least 70% identity, more particularly at least 80% identity, more particularly at least 90% identity, more particularly at least 95% identity, more particularly at least 98% identity, more particularly at least 97% identity, more particularly at least 98% identity, more particularly at least 99% identity or most particularly 100% identity with the nucleotide sequence of position 88 to 735 of SEQ ID NO: 9.

SEQ ID NO: 12

In a particular embodiment the polynucleotide of the invention encodes a acid phosphatase or a phytase or a phospholipase C and comprises or consists of an nucleotide sequence which has at least 70% identity, more particularly at least 80% identity, more particularly at least 90% identity, more particularly at least 95% identity, more particularly at least 95% identity, more particularly at least 97% identity, more particularly at least 98% identity, more particularly at least 99% identity or most particularly 100% identity with the nucleotide sequence of position 82 to 1824 of SEQ ID NO: 12.

SEQ ID NO: 13 and 14

In a particular embodiment the polynucleotide of the invention encodes a polysaccharide deacetylase or a xylan deacetylase and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 78 to 750 of SEQ ID NO: 13 or position 64 to 972 of SEQ ID NO: 14.

SEQ ID NO: 15

In a particular embodiment the polynucleotide of the invention encodes a sulfite oxidase and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 88 to 642 of SEQ ID NO: 15.

SEQ ID NO: 16

In a particular embodiment the polynucleotide of the invention encodes a mature functional polypeptide and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 84 to 771 of SEQ ID NO: 18.

SEQ ID NO: 17

In a particular embodiment the polynucleotide of the invention encodes mature functional polypeptide and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 73 to 3390 of SEQ ID NO: 17.

SEQ ID NO: 18

In a particular embodiment the polynucleotide of the invention encodes a mature functional polypeptide and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 124 to 744 of SEQ ID NO: 18.

SEQ ID NO: 19

In a particular embodiment the polynucleotide of the invention encodes a mature functional polypeptide and comprises or consists of an nucleotide sequence which has at least 70% Identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 76 to 616 of SEQ ID NO: 19.

SEQ ID NO: 20

In a particular embodiment the polynucleotide of the invention encodes a mature functional polypeptide and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 91 to 726 of SEQ ID NO: 20.

SEQ ID NO: 21

In a particular embodiment the polynucleotide of the invention encodes a mature functional polypeptide and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 73 to 540 of SEQ ID NO: 21.

SEQ ID NO: 22

In a particular embodiment the polynucleotide of the invention encodes a mature functional polypeptide and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 76 to 1431 of SEQ ID NO: 22.

SEQ ID NO: 23

In a particular embodiment the polynucleotide of the invention encodes a mature functional polypeptide and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 58 to 1020 of SEQ ID NO: 23.

SEQ ID NO: 24

In a particular embodiment the polynucleotide of the invention encodes a mature functional polypeptide and comprises or consists of an nucleotide sequence which has at least 70% identity, more particularly at least 80° h identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 88 to 1023 of SEQ ID NO: 24.

SEQ ID NO: 25

In a particular embodiment the polynucleotide of the invention encodes a mature functional polypeptide and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 85 to 1197 of SEQ ID NO: 25.

Modification of a nucleotide sequence encoding a polypeptide of the present invention may be necessary for the synthesis of a polypeptide which comprises an amino acid sequence that has at least one substitution, deletion and/or insertion as compared to an amino acid sequence selected from mature polypeptide comprised in SEQ ID NO: 26 to SEQ ID NO: 50.

It will be apparent to those skilled in the art that such modifications can be made to pre-serve the function of the enzyme i.e. made outside regions critical to the function of the enzyme. Amino acid residues which are essential to the function are therefore preferably not subject to modification, such as substitution. Amino acid residues essential to the function may be identified according to procedures known in the art, such as site-directed mutagenesis or alanine-scanning mutagenesis (see, e.g., Cunningham and Wells, 1989, *Science* 244: 1081-1085). Sites of substrate-enzyme interaction can be determined by analysis of the three-dimensional structure as determined by such techniques as nuclear magnetic resonance analysis, crystallography or photoaffinity labeling (see, e.g., de Vos et al., 1992, *Science* 255: 306-312; Smith et 81., 1992, *Journal of Molecular Biology* 224: 899-904; Wiodaver et al., 1992, *FEBS Letter* 309: 59-64).

Moreover, a nucleotide sequence encoding an enzyme of the invention may be modified by introduction of nucleotide substitutions which do not give rise to another amino acid sequence of the enzyme encoded by the nucleotide sequence, but which correspond to the codon usage of the host organism intended for production of the enzyme.

The introduction of a mutation into the nucleotide sequence to exchange one nucleotide for another nucleotide may be accomplished by site-directed mutagenesis using any of the methods known in the art. Particularly useful is the procedure, which utilizes a super coiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with Dpnl, which is specific for methylated and hemimethylated DNA to digest the parental DNA template and to select for mutation-containing synthesized DNA. Other procedures known in the art may also be used. For a general description of nucleotide substitution, one may consult with e.g., Ford et al., 1991, *Protein Expression and Purification* 2: 95-107.

The present invention also relates to a polynucleotide comprising, preferably consisting of, a nucleotide sequence which encodes a polypeptide of the invention and which hybridizes under high stringency conditions, preferably under very high stringency conditions with a polynucleotide probe selected from the group consisting of:

(i) the complementary strand to a nucleotide sequence selected from the regions of SEQ ID NO: 1 to SEQ ID NO: 25 encoding a mature polypeptide, (ii) the complementary strand to the cDNA sequence contained in a nucleotide sequences selected from the regions of SEQ ID NO: 1 to SEQ ID NO: 25 encoding a mature polypeptide and, (iii) a fragment of (i) or (ii) encoding a secreted mature polypeptide having the function of the corresponding mature polypeptides comprised in SEQ ID NO:26 to SEQ ID NO:50

(J. Sambrook, E. F. Fritsch, and T. Maniatus, 1989, Molecular Cloning, A Laboratory Manual, 2d edition, Cold Spring Harbor, N.Y.).

As will be understood, details and particulars concerning hybridization of the nucleotide sequences will be the same or analogous to the hybridization aspects discussed in the section titled "polypeptides of the invention" herein.

The present invention also encompasses a storage medium suitable for use in an electronic device comprising information of the amino acid sequence of polypeptides of the invention or the nucleotide sequences of the polynucleotide of the invention. The storage medium may suitably be a magnetic or optical disk and the electronic device a computing device and the information may in particular be stored on the storage medium in a digital form.

Nucleotide Constructs

The present invention also relates to nucleic acid constructs comprising a nucleotide sequence of the invention operably linked to one or more control sequences that direct the expression of the coding sequence in a suitable host cell under conditions compatible with the control sequences.

A nucleotide sequence encoding an enzyme of the invention may be manipulated in a variety of ways to provide for expression of the enzyme. Manipulation of the nucleotide sequence prior to its insertion into a vector may be desirable or necessary depending on the expression vector. The techniques for modifying nucleotide sequences utilizing recombinant DNA methods are well known in the art.

The control sequence may be an appropriate promoter sequence, a nucleotide sequence that is recognized by a host cell for expression of the nucleotide sequence. The promoter sequence contains transcriptional control sequences, which mediate the expression of the polypeptide. The promoter may be any nucleotide sequence which shows transcriptional activity in the host cell of choice including mutant, truncated, and hybrid promoters, and may be obtained from genes encoding extra cellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase and *Fusarium oxysporum* trypsin-like protease (WO 96/00787), as well as the NA2-tpI promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enclase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the enzyme. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enclase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a non-translated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Alicyclobacillus oryzae* TAKA amylase and *Aspergillus nidulans* triose phosphate isomerase.

Suitable leaders for yeast host cells are obtained from the genes for *Saccharomyces cerevisiae* enclase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Alicyclobacillus oryzae* TAKA amylase, *Aspergillus niger* glucoamylase, *Alicyclobacillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5988-5990.

The control sequence may also be a signal peptide coding region that codes for an amino acid sequence linked to the amino terminus of a polypeptide and directs the encoded enzyme into the cell's secretory pathway. The 5' end of the coding sequence of the nucleotide sequence may inherently contain a signal peptide coding region naturally linked in translation reading frame with the segment of the coding region which encodes the secreted enzyme. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the enzyme. However, any signal peptide coding region which directs the expressed enzyme into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin. *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Alicyclobacillus niger* neutral amylase, *Aspergillus niger* glucoamylase, *Rhizomucor miehel* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a enzyme. The resultant polypeptide may be denoted a pro-enzyme or propolypeptide. A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophile* laccase (WO 95/33836.

Where both signal peptide and propeptide regions are present at the amino terminus of a polypeptide, the propeptide region is positioned next to the amino terminus of a polypeptide and the signal peptide region is positioned next to the amino terminus of the propeptide region. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences.

Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Recombinant Expression Vectors

The present invention also relates to recombinant expression vectors comprising the nucleic acid construct of the invention. The various nucleotide and control sequences described above may be joined together to produce a recombinant expression vector, which may include one or more convenient restriction sites to allow for insertion or substitution of the nucleotide sequence encoding the polypeptide at such sites. Alternatively, the nucleotide sequence of the present invention may be expressed by inserting the nucleotide sequence or a nucleic add construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about the expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome.

The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers that permit easy selection of transformed cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransforase), hygB (hygromycin phosphotransferase), nlaD (nitrate reductase), pyrG (orotidine-5'-phosphate decarboxylase), sC (sulfate adenyltransferase), trpC (anthranilate synthase), as well as equivalents thereof.

Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cells genome or autonomous replication of the vector in the cell independent of the genome.

For integration into the host cell genome, the vector may rely on the nucleotide sequence encoding the polypeptide or any other element of the vector for stable integration of the vector into the genome by homologous or nonhomologous recombination. Alternatively, the vector may contain additional nucleotide sequences for directing integration by homologous recombination into the genome of the host cell. The additional nucleotide sequences enable the vector to be integrated into the host cell genome at a precise location(s) in the chromosome(s). To increase the likelihood of integration at a precise location, the integrational elements should preferably contain a sufficient number of nucleotides, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6.

The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleotide sequence of the present invention may be inserted into the host cell to increase production of the gene product. An increase in the copy number of the nucleotide sequence can be obtained by integrating at least one additional copy of the sequence into the host cell genome or by including an amplifiable selectable marker gene with the nucleotide sequence where cells containing amplified copies of the selectable marker gene, and thereby additional copies of the nucleotide sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al, 1989, supra).

Recombinant Host Cells

The present invention also relates to recombinant a host cell comprising the nucleic acid construct of the invention, which are advantageously used in the recombinant production of the polypeptides. A vector comprising a nucleotide sequence of the present invention is introduced into a host cell so that the vector is maintained as a chromosomal integrant or as a self-replicating extrachromosomal vector as described earlier.

The host cell may be a unicellular microorganism, e.g., a prokaryote or a non-unicellular microorganism, e.g., a eukaryote.

Useful unicellular cells are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* and *Bacillus thuringlensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is a *Bacillus lentus, Bacillus licheniformis, Bacillus stearothermophilus,* or *Bacillus subtilis* cell. In another preferred embodiment, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may be a eukaryote, such as a mammalian, insect, plant, or fungal cell.

In a preferred embodiment, the host cell is a fungal cell. "Fungi" as used herein includes the phyla Ascomycota, Basidiomycota, Chytridiomycota, and Zygomycota (as defined by Hawksworth et al., in, *Alnsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra). In a more preferred embodiment, the fungal host cell is a yeast cell. "Yeast" as used herein includes ascosporogenous yeast (Endomycetales), basidiosporogenous yeast, and yeast belonging to the *Fungi imperfecti* (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series No.* 9, 1980).

In an even more preferred embodiment, the yeast host cell is a *Candida, Hansenula, Kluyveromyces, Pichia, Saccharomyces, Schizosaccharomyces,* or *Yarrowia* cell.

In a most preferred embodiment, the yeast host cell is a *Saccharomyces carlsbergensia, Saccharomyces cerevisiae, Saccharomyces diastaticus, Saccharomyces douglesii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, *Acremonium, Aspergillus, Fusarium, Humicola, Mucor, Myceliophthora, Neurospora, Penicillium, Thielavia, Tolypocladium,* or *Trichoderma*.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichloides, Fusarium sulphureum, Fusarium torulosum, Fusarium trichothecloides,* or *Fusarium venenatum* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzienum, Trichoderma koningil, Trichoderms longibrachiatum, Trichoderma reesai,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming *Fusarium* species are described by Malardier et al, 1989, *Gene* 78: 147-156 and WO 96/00787. Yeast may be transformed using the procedures described by Becker and Guarente, in Abelson, J. N. and Simon, M. I., editors, *Guide to Yeast Genetics and Molecular Biology, Methods In Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods for Preparing Enzyme Polypeptides

The present invention also relates to methods for producing an enzyme of the invention comprising (a) cultivating a strain comprising a nucleotide sequence encoding an enzyme of the invention which strain is capable of expressing and secreting the enzyme and (b) recovering the enzyme. In a particular embodiment the strain is a wild type strain such as the *Aspergillus* sp. DSM 15716, while in another embodiment the strain is a recombinant host cell as described, supra.

In these methods of the invention, the cells are cultivated in a nutrient medium suitable for production of the enzyme using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). As the enzyme is secreted into the nutrient medium, the enzyme can be recovered directly from the medium.

The resulting enzyme may be recovered by methods known in the art. For example, the enzyme may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophorus procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Transgenic Plants

The present invention also relates to a transgenic plant, plant part, or plant cell that has been transformed with a nucleotide sequence encoding an enzyme of the invention so as to express and produce the enzyme. In one embodiment the plant could be used as host for production of enzyme in recoverable quantities. The enzyme may be recovered from the plant or plant part. Alternatively, the plant or plant part containing the recombinant enzyme may be used as such for improving the quality of a food or feed, e.g., improving nutritional value, palatability, and rheological properties, or to destroy an antinutritive factor. In particular the plant or plant parts expressing the enzyme may be used as an improved starting material for production of fuel-alcohols or bio-ethanol The transgenic plant can be dicotyledonous (a dicot) or monocotyledonous (a monocot). Examples of monocot plants are grasses, such as meadow grass (blue grass, Poa), forage grass such as *festuca*, lollum, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family *Brassicaceae*), such as cauliflower, rape seed, and the closely related model organism *Arabidopsis thaliana*.

Examples of plant parts are stem, callus, leaves, foot, fruits, seeds, and tubers. Also specific plant tissues, such as chloroplast, apoplast, mitochondria, vacuole, peroxisomes, and cytoplasm are considered to be a plant part. Furthermore, any plant cell, whatever the tissue origin, is considered to be a plant part.

Also included within the scope of the present invention are the progeny of such plants, plant parts and plant cells.

The transgenic plant or plant cell expressing an enzyme of the invention may be constructed in accordance with methods known in the art. Briefly, the plant or plant cell is constructed by incorporating one or more expression constructs encoding an enzyme of the invention into the plant host genome and propagating the resulting modified plant or plant cell into a transgenic plant or plant cell.

Conveniently, the expression construct is a nucleic acid construct which comprises a nucleotide sequence encoding an enzyme of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the enzyme is desired to be expressed. For instance, the expression of the gene encoding an enzyme of the invention may be constitutive or inducible, or may be developmental, stage or tissue specific, and the gene product may be targeted to a specific tissue or plant part such as seeds or leaves. Regulatory sequences are, for example, described by Tague at al., 1988, *Plant Physiology* 86: 508.

For constitutive expression, the 35S-CaMV promoter may be used (Franck et al., 1980, *Cell* 21: 285-294). Organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu at al., 1998, *Plant and Cell Physiology* 39: 885-889), a *Vicia feba* promoter from the legumin B4 and the unknown seed protein gene from *Vicia feba* (Conrad et al., 1998, *Journal of Plant Physiology* 152: 708-711), a promoter from a seed oil body protein (Chen et al., 1998, *Plant and Cell Physiology* 39: 935.941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka at al., 1993, *Plant Physiology* 102: 991-1000, the chlorella virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588).

A promoter enhancer element may also be used to achieve higher expression of the enzyme of the invention in the plant. For instance, the promoter enhancer element may be an intron which is placed between the promoter and the nucleotide sequence encoding an enzyme of the present invention. For instance, Xu et al, 1993, supra disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort. 1992, *Plant Molecular Biology* 19: 15-38). However it can also be used for transforming monocots, although other transformation methods are generally preferred for these plants. Presently, the method of choice for generating transgenic monocots is particle bombardment (microscopic gold or tungsten panicles coated with the transforming DNA) of embryonic call or developing embryos (Christou, 1992, *Plant Journal* 2: 275-281; Shimamoto, 1994, *Current Opinion Biotechnology* 5: 158-162; Vasil et al., 1992, *Bio/technology* 10: 667-674). An alternative method for transformation of monocots is based on protoplast transformation as described by Omirulleh et al., 1993, *Plant Molecular biology* 21: 415-428.

Following transformation, the transformants having incorporated therein the expression construct are selected and regenerated into whole plants according to methods well known in the art.

The present invention also relates to methods for producing an enzyme of the invention comprising (a) cultivating a transgenic plant or a plant cell comprising a nucleotide sequence encoding an enzyme of the invention under conditions conducive for production of the enzyme and (b) recovering the enzyme.

Compositions Comprising Polypeptides and Methods for their Preparation

The invention provide a composition comprising a polypeptide of the invention and an excipient and a method for preparing such a composition comprising admixing the polypeptide of the invention with an excipient. In a particular embodiment the polypeptide of the invention is the major (polypeptide) component of the composition, e.g., a mono-component composition. The excipient in this context is to be understood as any auxiliary agent or compound used to formulate the composition and includes solvent, carriers, stabilizers and the like.

The composition may further comprise one or more additional enzymes, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenaloxidase, proteolytic enzyme, ribonuclease, transglutaminase, or xylanase.

The compositions may be prepared in accordance with methods known in the art and may be in the form of a liquid or a solid composition. For instance, the enzyme composition may be formulated using methods known to the art of formulating polypeptides and/or pharmaceutical products, e.g. Into coated or uncoated granules or micro-granules. The polypeptide of the invention may thus be provided in the form of a granule, preferably a non-dusting granule, a liquid, in particular a stabilized liquid, a slurry or a protected polypeptide. For certain applications, immobilization of the polypeptide on a solid matrix may be preferred.

The polypeptide to be included in the composition may be stabilized in accordance with methods known in the art e.g. by stabilizing the polypeptide in the composition by adding and antioxidant or reducing agent to limit oxidation of the polypeptide or n may be stabilized by adding polymers such as PVP, PVA, PEG or other suitable polymers known to be beneficial to the stability of polypeptides in solid or liquid compositions In a further embodiment the composition of the invention is a detergent composition which, in addition to the polypeptide of the invention, comprises a surfactant and optionally compounds selected from the group consisting of builders such as zeolites, bleaching agents such as percarbonate, bleach enhancers such as TAED or NOBS, suds suppressors, fragrants, etc.

In a further embodiment the composition of the invention is a feed composition that in addition to the polypeptide of the invention comprises a cereal or grain product.

In a further embodiment the composition of the invention is a food composition such as a bakers flour composition, a brewed product, a fruit juice, an oil or lard product comprising the polypeptide of the invention.

In a further embodiment the composition of the invention is a pulping composition, which in addition to the polypeptide of the invention, comprises pulp.

In a further embodiment the composition of the invention is a biocidal composition, which comprises in addition to the polypeptide of the invention, an oxidoreductase enhancer.

Use of Polypeptides or Compositions Comprising them

In still further aspects the invention provides use of the polypeptides or polynucleotides of the invention or a composition comprising said polypeptides or polynucleotides in various applications, particularly (technical) processes such as processes performed in industry or house hold, herein under for commercial research purposes. Hence the invention encompasses a process comprising employing a polypeptide of the invention or a polynucleotide of the invention in a (technical) industrial, research or household process.

In one embodiment the polypeptide or the composition of the invention is used for cleaning a cellulosic fabric.

In another embodiment the polypeptide or the composition of the invention is used to prepare a food or feed additive.

In yet another embodiment the polypeptide or the composition of the invention is used for treatment of lignolosic materials and pulp.

Detergent Disclosure

The polypeptide of the invention may be added to and thus become a component of a detergent composition.

The detergent composition of the invention may for example be formulated as a hand or machine laundry detergent composition including a laundry additive composition suitable for pretreatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the polypeptide of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include Alcalase®, Savinase®, Primase®, Duratase®, Esperese®, and Kannase® (Novozymes A/S), Maxatase®, Maxacal®, Maxapem®, Properase®, Purafect®, Purafect OxP®, FN2®, and FN3® (Genencor International Inc.):

Lipases: Suitable lipases include those of bacterial or fungal origin. Chemically modified or protein engineered mutants are included. Examples of useful lipases include lipases from *Humicola* (synonym *Thermomyces*), e.g. from *H. lanuginosa* (*T. lanuginosus*) as described in EP 258 068 and EP 305 216 or from *H. insolens* as described in WO 96/13580, a *Pseudomonas* lipase, e.g. from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 (WO 95/06720 and WO 96/27002), *P. wisconsinensis* (WO 98/12012), a *Bacillus* lipase, e.g. from *B. subtilis* (Dartois et al. (1993), Biochemica et Biophysica Acta, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 98/00292, WO 95/30744, WO 94/25578, WO 95/14783, WO 95/22615, WO 97/04079 and WO 97/07202.

Preferred commercially available lipase enzymes include Lipolase™, Lipolase Ultra™ and Lipex (Novozymes A/S).

Amylases: Suitable amylases (alpha and/or bets) include those of bacterial or fungal origin. Chemically modified or protein engineered mutants are included. Amylases include, for example, alpha-amylases obtained from *Bacillus*, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novozymes A/S), Rapidase™ and Purastar™ (from Genencor International Inc.).

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Myceliophthora thermophila* and *Fusarium oxysporum* disclosed in U.S. Pat. Nos. 4,435,307, 5,648,263, 5,891,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,783,254, WO 95/24471, WO 98/12307 and PCT/DK98/00299.

Commercially available cellulases include Celluzyme®, and Carezyme® (Novozymes), Clazinase®, and Puradax HA® (Genencor International Inc.), and KAC-500(B)® (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257.

Commercially available peroxidases include Guardzyme® (Novozymes A/S).

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,218.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkyl-polyglucoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a H2O2 source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01-100 mg of enzyme protein per litre of wash liquor, preferably 0.05-5 mg of enzyme protein per liter of wash liquor, in particular 0.1-1 mg of enzyme protein per litre of wash liquor.

The enzyme of the invention may additionally be incorporated in the detergent formulations disclosed in WO 97/07202 that is hereby incorporated as reference.

Deposited Microorganisms

The following microorganism were deposited by the applicant according to the Budapest Treaty on the International Recognition of the Deposits of Microorganisms for the Purpose of Patent Procedures at Deutsche Sammlung von Mikroorganismen und Zellkulturen GmbH, Mascheroder Weg 1b, D-38124 Braunschweig, Germany:

Jun. 30, 2003: *Alicyclobacillus* sp. CS81 thermo-acidophile; DSM accession No. 15716

EXAMPLES

Example 1

Identifying Functional Polypeptides Secreted by *Alicyclobacillus* sp. DSM 15716

Genomic Library Construction

Chromosomal DNA from *Alicyclobacillus* sp. DSM 15716 was prepared by using standard molecular biology techniques (Ausuble et al. 1995 "Current protocols in molecular biology" Publ: John Wiley and sons). The prepared DNA was partially cleaved with Sau3A and separated on an agarose gel. Fragments of 3 to 8 kilobases were eluted and precipitated and resuspended in a suitable buffer.

A genomic library was made by using the Stratagene ZAP Express™ predigested Vector kit and Stratagene ZAP Express™ predigested Gigapack® cloning kit (Bam HI predigested) (Stratagene Inc., USA) following the instructions/recommendations from the vendor. The resulting lambdaZAP library comprised 38000 pfu of which 10000 were collected for mass excision. The resulting 70000 *E. coli* colonies were pooled and plasmids were prepared by using the Qiagen Spin Mini prep kit (Qiagen, Germany). The eluate of approx. 1 ml containing the plasmid DNA was precipitated in a centrifuge with 1 volume part of Na-acetate pH5 and 2 volume parts 96% ethanol at 20000 rpm at 4C, washed with 70% v/v ethanol, died at room temperature and resuspended in 200 microl TE buffer. The DNA concentration of the plasmid pool DNA of the *Alicyclobacillus* sp. genomic library was 5.2 microgram/microliter.

Transposon Construction and Preparation

The rationale behind the methology of Transposon Assisted Signal Trapping (TAST) as described in WO 01/77315 A1 is to fuse all genes within a selected genome with a gene encoding a signalless beta-lactamase via a transposon tag. Hence when growing host cell clones comprising the genes of a genome fused with a gene encoding a signalless bet-lactamase via a transposon tag in an ampicillin containing medium only those clones expressing and secreting a beta-lactamase will survive. However the beta-lactamase will only be secreted if the gene to which the beta-lactamase gene is fused has an intact promoter and ribosome binding site (i.e. a gene which is expressed by the cell to produce a polypeptide in real life), which can be recognized in the host strain, and if the beta-lactamase is translated so that the synthesized polypeptide is transported across the cytoplasms membrane and folded correctly. Hence, when inserting the fused gene into a selected host cell, those clones, which are ampicillin resistant contains a gene which encodes a functional secreted polypeptide.

Usually, when employing the TAST methodology it is even not necessary to express the entire gene. When tagging the genes with a transposon, expression of the N-terminal part of the genes as protein fusion shows that the genes contain intact transcription, translation and secretion sequences. Hence expression of the N-terminal part of the genes as protein fusion is usually regarded as sufficient for assuring expression and secretion of the entire gene.

Thus it can be concluded that the genes obtained by the TAST method actually do encode secreted functional polypeptides.

Construction of a SigA4 Transposon Containing the β-Lactamase Reporter Gene:

Following the instructions of WO 01/77315 A1, the construction of a transposon containing a signal-less β-lactamase gene was carried out using standard molecular biology techniques. The signal-less β-lactamase gene was initially PCR amplified from the vector pUC19) using a proofreading polymerase (Pfu Turbo, Stratagene, USA). The resulting PCR fragment contained the restriction sites NotI and EcoRI in order to aid cloning. The plasmid pEntranceposon (Cam') containing the Entranceposon and the antibiotic resistance markers CAT (encoding chloramphencol resistance in the transposon) was obtained from Finnzymes, OY (Espoo Finland). The plasmid was digested with the restriction enzymes NotI and EcoRI, gel purified and ligated with the signal-less β-lactamase containing fragment. The ligation was transformed into electro-competent DH10 cells and the *E. coli* clone containing the recombinant plasmid with the signal-less β-lactamase was identified by restriction analysis and named SigA2.

For transposon preparation, a smaller derivative of SigA2 was constructed, which lacked the bla gene encoding beta-lactamase: Two oligonucleotide primers SigA2NotU-P 5'-TCG CGA TCC GTT TTC GCA TTT ATC GTG AAA CGC T-3' (SEQ ID NO: 51) and SigA2NotD-P 5'-CCG CM ACG CTG GTG AAA GTA AAA GAT GCT GAA-3' (SEQ ID NO: 52), which bind to the start and stop of the bla gene of SigA2 directing outwards were used PCR amplify-SigA2 without the bla gene. An amplificate of approx. 3.6 kb generated in the this PCR reaction was relegated and transformed in to a suitable *E. coli* strain. A plasmid of 3.6 kb was isolated from a transformant which was able to grow on LB chloramphenicol but not on LB ampicillin. This plasmid maintained both BglII sites and lacks the active bla gene and was called pSig4.

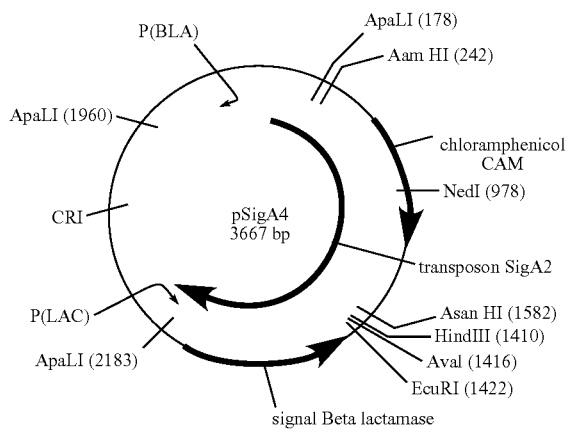

60 microliter of pSigA4 plasmid DNA preparation with a concentration of 0.3 microgram/microliter was digested with BglII and separated on an agarose gel. The SigA2 transposon DNA band of 2 kb was eluted and purified by using the "GFX™PCR, DNA and Gel Band Purification Kit" (Amersham Pharmacia Biotech Inc, USA) according to the instructions of the vender and eluted in 200 microliter EB buffer.

C. Transposon Togging

The transposon prepared from pSigA4 carries a 5'-truncated bla-gene encoding a β-lactamase from which the secretion signal has been removed. The β-lactamase conveys ampicillin resistance on *E. coli* only when the protein is secreted to the periplasm, whereas cytoplasmic expression of β-lactamase does not confer ampicillin resistance. Without a signal sequence, the β-lactamase enzyme will not be transported to the periplasm and therefore the done will not grow on media containing ampicillin. The signal-less β-lactamase gene was contained within the transposon in such a way that there was a continuous open reading frame between the transposon border and the β-lactamase coding region. In this way the modified transposon, when it transposes into a gene encoding a protein that is secreted, could cause an in-frame fusion with the target gene. This resulted in a fusion gene product that is secreted to the periplasm of *E. coli* and conveys resistance to the ampicillin. If the transposon integrated even in-frame into a gene encoding a non-secreted protein, the respective host will not become ampicillin resistance.

For the in vitro transposon tagging of the *Alicyclobacillus* sp. library, 4 or 8 microliter of SigA2 transposon containing approx. 2.6 ug DNA were mixed with 1 microliter of the DNA concentration of the plasmid pool DNA of the *Alicyclobacillus* sp. genomic library, 2 microliter of Finnzymes MuA Transposase (0.22 microgram/microliter) and 5 microliter of 5× buffer from Finnzymes OY, Espoo, Finland) in a total volume of 50 microliter and incubated at 30° C. for 3.5 h and followed by heat inactivation at 75° C. for 10 min. The DNA was precipitated by addition of 5 microliter 3M Na-acetate pH5 and 110 microliter 95% ethanol and centrifugation for 30 min at 20000 rpm. The pellet was washed and dried and resuspended in 10 microliter TE buffer.

D. Transformation and Selection

Electro-competent *E. coli* DH10B cells were transformed by electroporation in a Biorad Gene Pulse device (50 uF, 25 mAmp, 1.8 kV with 5 microliter of the transposon tagged plasmid pool, mixed with 1 ml SOC medium, pro-incubated for 1 h at 37C and plated on LB with 25 microliter/milliliter ampicillin, 50 microliter/milliliter kanamycin, 10 microliter/milliliter chloramphenicol and incubated for 2-3 days. Out of the resistant transformants 1056 colonies were selected and plasmids were prepared by applying the Qiaprep 96 Turbo Biorobot kit according to the instructions of the vender.

E. Plasmid Preparation and Sequencing 1056 transposon tagged plasmids were sequenced in with the A2up primer AGCGTTTGCGGCCGCGATCC (SEQ ID NO: 53) which read upstream into the into the transposon tagged gene, and, in a second reaction, with B primer TTATTCGGTCGAAAAGGATCC (SEQ ID NO: 54) which read downstream into the transposon tagged gene.

F. Sequence Assembly and Annotation

The obtained sequences were assembled into contigs by using the program PhredPhrap (Brent Ewing, LaDeana Hillier, Michael C. Wendl, and Phil Green, Base-calling of automated sequencer traces using phred I. Accuracy assessment (1998) Genome Research 8:175-185; Brent Ewing and Phil Green, Base-calling of automated sequencer traces using phred II. Error probabilities (1998) Genome Research 8:186-194). The obtained contigs were subsequently compared to sequences available in standard public DNA and protein sequences databases by using the program BLASTX 2.0a19MP-WashU [14 Jul. 1998] [Build linux-x86 18:51:44 30 Jul. 19981] (Gish, Warren (1994-1997). Unpublished; Gish, Warren and David J. States (1993). Identification of protein coding regions by database similarity search. Nat. Genet. 3:266-72).

The obtained sequences were functional genes which encoded intact and functional polypeptides, because they were obtained as ampicillin resistant clones as explained supra.

Example 2

Determining Function by Homology

The function of the polypeptides SEQ ID NO: 26 to SEQ ID NO: 60 were annotated by sequences comparison with genes or polypeptides of known function. The polypeptides of the invention were compared to a list of closest related sequences from public and inhouse databases of contig's. The contigs, from which SEQ ID NO: 26 to SEQ ID NO: 50 were derived, were subsequently compared to sequences available in standard public DNA and protein sequences databases by using the program BLASTX 2.0a19MP-WashU [14 Jul. 1998]. A careful analysis of sequence alignments of SEQ ID NO: 26 to SEQ ID NO: 40 to their closest related sequences with known function from other databases made it possible to predict the function of these polypeptides on the basis of the degree of amino acid identity. Even when the overall amino acid identity was below 40%, which usually makes it difficult to make a good prediction, we were able to predict the function of SEQ ID NO: 26 to SEQ ID NO: 40 by carefully analysing and interpreting the amino acid residues in the catalytic sites or in important regions of the polypeptide sequences. If the amino acids of the catalytic site of a known sequences were also present in the polypeptide of the invention, combined with a sufficient overall amino acid identity, it was concluded that the polypeptide from *Alicyclobacillus* sp DSM 15716 had the same function as the known sequence.

Example 3

Preparing Polypeptides of SEQ ID NO: 26 to SEQ ID NO: 50

To prepare the polypeptides of SEQ ID NO: 26 to SEQ ID NO: 50, the genes comprised in SEQ ID NO: 1 to SEQ ID NO: 25 encoding these polypeptides are expressed by fusing the DNA encoding the open reading frame to DNA a promoter, ribosome-binding site and terminator suitable for genes expression in an appropriate host strain, for example *Escherichia coli, Bacillus subtilis, Bacillus licheniformis* or *Bacillus clausii* or a derivative of *Alicyclobacillus* sp. The promoter can either be an inducible promotor or a constitutive promoter. Any signal sequences of SEQ ID NO: 26 to SEQ ID NO: 50 can be exchanged with a suitable signal peptide of another bacterium. The expression construct can either be part of a plasmid or of a linear DNA. It can be integrated into the chromosome of the host stain by recombination or it can be present in the host cell on a plasmid. Then the transformed cells carrying the gene of interest are grown in a suitable medium in the desired volume. If an inducible promoter is used, the gene expression is started by adding the inducer. Otherwise a no inducer is needed and the cells will be grown until a suitable amount of protein from the gene of interest is produced. Then the culture is harvested and the proteins are recovered by standard methods.

Example 4

Determining Serine-Carboxyl Protease Activity

The culture fluid or a cell lysate of a host strain synthesising and secreting a serine-carboxy protease in a suitable buffer may be assayed for that activity. A suitable volume of such a sample is spotted on agarose plates which contain the insoluble chromogenic substrate AZCL-collagen (Megazyme™) or Azocoll (Sigma-Aldrich) and a suitable buffer at acidic pH, e.g. pH is 35. The plate is incubated for an appropriate time, e.g. one day at an appropriate temperature, e.g. 55□C. The activity is visible as blue halos around the spots. As an alternative to AZCL-collagen or Azocoll, non-labelled collagen is added to agar plates, on which enzyme activity can be detected as clearing zones. By addition of pepstatin, the protease activity of a serine carboxyl protease cannot be inhibited. As an alternative, the activity determination of a sample containing a serine-carboxyl protease can be measured as described in Tsuruoka N. Nakayama T. Ashida M, Hemmi H, Nakao M, Minakata H, Oyama H. Oda K, Nishino T; "*Collagenolytic serine-carboxyl proteinase from Alicyclobacillus sendalensis strain NTAP-1: purification, characterization, gene cloning, and heterologous expression*." Appl Environ Microbiol. Vol. 69(1); pp 162-169; 2003 Jan.

Example 5

Determining Multi-Copper Oxidase Activity

The culture fluid or a cell lysate of a host strain synthesising and secreting a multi-copper oxidase in a suitable buffer may be assayed for that activity as described in Schneider et al., Enzyme and Microbial Technology 25, (1999) p. 502-508).

For example a suitable volume, which can be 15 microliter, of such a sample is spotted on agarose plates which contain ABTS (2,2'-Azinobis 3-Ethylbenzthiazolin-6-sulfonic acid) at a suitable concentration, e.g. 1 mM, in a suitable puffer, e.g. 0.1 M sodium acetate buffer for pH 5.5. The plate is incubated for an appropriate time e.g. 16 hours, at an appropriate temperature, e.g. 55° C. The activity is visible as a green zone around the sample. The assay world on supernatants and extracts.

Example 6

Determining Serine Protease Activity

The culture fluid or a cell lysate of a host strain synthesising and secreting a serine protease in a suitable buffer may be assayed for that activity. A suitable volume of such a sample is spotted on agarose plates which contain the insoluble chromogenic substrate AZCL-casein (Megazyme™) or AZCL-collagen (Megazyme™) and a suitable buffer at suitable pH. The plate is incubated for an appropriate time, e.g. one day, at an appropriate temperature, e.g. 55□C. The activity is visible as blue halos around the spots. As an alternative to AZCL-casein and AZCL-collagen (Megazyme™) non-labelled casein or non-labelled collagene can be used. On non-labelled collagen or non-labelled casein spotted on agarose plates, clearing zones form in the presence of a serine protease.

Example 7

Determining Aspartyl Protease Activity

The culture fluid or a cell lysate of a host strain synthesising and secreting an aspartyl protease in a suitable buffer was assayed for that activity. A suitable volume of such a sample can be spotted on agarose plates, which contain the insoluble chromogenic substrate AZCL-collagen (Megazyme™) and a suitable buffer at acidic pH, e.g. pH 113-5. The plate can be incubated for an appropriate time, e.g. one day, at an appropriate temperature, e.g. 55□C. The activity is visible as blue halos around the spots. As an alternative to AZCL-collagen, non-labelled collagen can be used. On non-labelled collagen spotted on agarose plates, clearing zones form in the presence of an aspartyl protease. Upon specifically testing the aspartyl protease of ID NO: 27; the activity was determined as a spot test of 20 microliter culture fluid on 0.1% AZCL-collagen (Megazyme™) spotted on LB-PG agar plates at pH 3.4. The plates were incubated at 55° C. (over night) and the presence of the aspartyl protease was visible as blue halos around the spots.

The aspartyl protease comprised in SEQ ID NO: 27 showed significant sequence similarity to aspartyl peptidases belonging to family M. This family contains peptidase sequences, which have an aspartate and a glutamate residue in their active site. Both residues were conserved in the aspartyl protease comprised in SEQ ID NO: 27. The aspartyl protease comprised in SEQ ID NO: 27 is thus the first bacterial polypeptide showing significant sequence similarity especially at the active sites with sequences from peptidase family A4 and therefore also the first bacterial A4 protease.

SEQ ID NO: 27 was compared to a reference sequence of family A4 peptidases; *Aspergillus niger* aspergillopepsin II (SEQ ID NO: 55; Swissprot P24665; Takcahashi, K.; Inoue, H.; Sakai, K.; Kohama, T. Kitahara, S.; Takishima, K.; Tanji, M.; Athauda, S. B. P.; Takahashi, T.; Akanuma, H.: Mamiya, G.; Yamasaki, M); *The primary structure of Aspergillus niger acid proteinase A.*; J. Biol. Chem.; Vol 286; p. 19480; 1991). This polypeptide contained a signal peptide (aa1-, and two propeptides (aa 19-58 and aa 99-109), which are removed after secretion during maturation. During maturation a heavy and a light chain are formed, which are cross-linked by disulfide bridges between cysteine residues. (Inoue, H.; Kimura, T.; Makabe, O.; Takahashi, K; *The gene and deduced protein sequences of the zymogene of Aspergillus niger acid proteinase A*; J. Biol. Chem.; vol. 286; p. 19484; 1991). The amino acids similar to the second propeptide (aa99-109) and the amino acids corresponding to the cross-linking cysteine residues of SEQ ID NO.55 are missing in SEQ ID 27 (see alignment). Only a fungal A4 peptidase has previously been described to lack cysteine residues (Maita, T.; Nagata, S.; Matsuda, G.; Maruta, S.; Oda, K.; Murao, S.; Tsuru, D.; *Complete amino acid sequence of Scytalidium lignicolum acid protease B*; J. Biochem.; vol. 95; p. 465; 1984).

Example 8

Determining Acid Beta-Glucanase Activity

The culture fluid or a cell lysate of a host strain synthesising and secreting an beta-glucanase in a suitable buffer may be assayed for that activity. A suitable volume of such a sample is spotted on agarose plates which contain the insoluble chromogenic substrate AZCL-beta-glucan (Megazyme™) and a suitable buffer at acidic pH, e.g. pH is 35. The plate is incubated for an appropriate time, e.g. one day, at an appropriate temperature, e.g. 55☐C. The activity is visible as blue halos around the spots.

Example 9

Determining Acid Phosphatase Activity

A suitable volume of the culture fluid or a call lysate of a host strain synthesising and secreting the acid phosphatase in a suitable buffer at a suitable pH at an appropriate temperature, e.g. 55° C. is incubated with para-nitrophenolphosphate (pNPP) for measuring the enzyme activity. The products of the enzymatic reaction are p-nitrophenol and inorganic phosphate or Pi. NaOH is added to end the phosphatase assay after a suitable reaction time and forms p-nitrophenotate. The absorption of p-nitrophenolate is measured optically at 405 nm.

As an alternative, a suitable volume of the culture fluid or a cell lysate of a host strain synthesising and secreting the acid phosphatase in a suitable buffer at a suitable pH at an appropriate temperature, e.g. 55° C. is used for measuring the enzyme activity with the EnzChek™ Acid Phosphatase Assay Kit (E-12020) (Molecular Probes Europe BV: PoortGebouw. Rijnsburgerweg 10; 2333 M Leiden, The Netherlands).

Example 10

Determining Polysaccharide Deacetylase Activity

A suitable volume of the culture fluid or a cell lysate of a host strain synthesising and secreting the polysaccharide

```
                Alignment of SEQ ID NO: 55 with SEQ ID NO: 27

SWISSPROT_P24665   MKFSTILTGS-LFATAALAAPLTEKRRARKEARAAGKRHSNPPYIPGSDKEILKLNGTTN
Seq ID No. 27      MNGTSVWKASGIAAASCLTAAALLAWPHATSTLDASPAIFHAPRHALSPNTSPKPNSVQA

¤¤¤¤¤¤¤¤¤¤   :
SWISSPROT_P24665   EEY---SSNWAGAVLIGDGYTKVTGEFTVPSVSAGSSGSSGYGGGYGYWKNKRQSEEQCA
Seq ID No. 27      QNFGWSASNWSGYAVTGSTYNDITGSWIVPAVSP---------------SKR--STYS-

*       :                        :
SWISSPROT_P24665   SAWVGIDGDTCETAILQTGVDFCYEDGQTSYDAWYEWYPDYAYDFSDITISEGDSIKVTV
Seq ID No. 27      SSWIGIDG-FNNSDLIQTGTEQDYVNGHAQYDAWWEILPAPETVISNMTIAPGDRMSAHI

:                 *
SWISSPROT_P24665   EATSKSSGSATVENLTTGQSVTHTFSGNVEGDLCETNAEWIVEDFESGDSLVAFADFGSV
Seq ID No. 27      MNNGNGTWTITLTDVTRNETFSTTQSYSGPG----SSAEWIQEAPEIGGRIATLANYGET

SWISSPROT_P24665   TFTNAEATSG--GSTVGPSDAT--------------------------------------
Seq ID No. 27      TFDPGTVNGGNPGFTLVPTRATWCRTTRSCLCRPHPTRIPTASTWPTAPTSRAHRPPDFR

SWISSPROT_P24665   -----VMDIEQDGSVLTETSVSGDSVTVTYV------------
Seq ID No. 27      RSRRPCMEAQGPASFFARTLAPSRDVAAHAPQGHRPSALVRRA
```

* = amino acids forming the active site in Swiseprot P24665
: = cysteine residues froming disulfide bonds in Swissprot P24665
¤ = propeptide removed from the Swissprot P24665 zymogene.

deacetylase in a suitable buffer at an appropriate temperature, e.g. 55°C is used for measuring the activity. Bacterial murein, N,N'-diacetylchitobiose (Sigma) or galactose pentaacetate (Sigma) or and cellulose acetate (Sigma) can be used as substrate(s) for this enzyme type. The acetate released from the substrate by the enzyme can be measured with an acetic acid assay kit (Biopharm) adapted for the physical requirements of the enzyme (Kosugi A, Murashima K, and Dol R H; *Xylanese and Acetyl Xylan Esterase Activities of XynA, a Key Sub-unit of the Clostridium cellulovorans Cellulosome for Xylan Degradation*; Appl. Environm. I Microbiol.; vol. 68; pp. 6399-6402; 2002)

Example 11

Determining Endo-Beta-N-Acetylglucosaminidase Activity

A suitable volume of the culture fluid or a cell lysate of a host strain synthesising and secreting the endo-beta-N-acetylglucosaminidase activity in a suitable buffer, e.g. pH 3-5, at an appropriate temperature, e.g. 55° C. can be used for measuring the activity in accordance with MH Rashid, M Mori and J Sekiguchi; *Glucosaminidase of Bacillus subtilis: cloning, regulation, primary structure and biochemical characterization*; Microbiology; vol. 141; pp. 2391-2404; 1995.

Example 12

Determining Peptidyl Poly-Isomerase Activity

A suitable volume of the culture fluid or a cell lysate of a host strain synthesising and secreting the polysaccharide deacetylase in a suitable buffer at an appropriate temperature, e.g. 55° C. is used for measuring the activity. The activity can be determined in accordance to Fischer, G., Bang, H. and Mech, C.; *Determination of enzymatic catalysis for the cis-trans-isomerization of peptide binding in proline-containing peptides*; Biomed. Biochim. Acta; vol. 43; pp. 1101-1111; 1984. This assay may be modified appropriately to suit the specific peptidyl polyisomerase such as that comprised in SEQ ID NO: 36.

Example 13

Determining Acid Cellulase Activity

The culture fluid or a cell lysate of a host strain synthesising and secreting an acid cellulase in a suitable buffer may be assayed for that activity. A suitable volume of such a sample is spotted on agarose plates which contain the insoluble chromogenic substrate AZCL-HE-cellulose (Megazyme™) and a suitable buffer at acidic pH, e.g. pH is 3-5. The plate is incubated for an appropriate time, e.g. one day, at an appropriate temperature, e.g. 55°C. Presence of acid cellulase is visible as blue halos around the spots.

Example 14

Determining Xylan Deacetylase Activity

A suitable volume of the culture fluid or a cell lysate of a host strain synthesising and secreting the polysaccharide deacetylase in a suitable buffer at an appropriate temperature, e.g. 55°C. can be used for measuring xylan deacetylase activity. Xylan deacetylase activity is measured as acetate release from acetylated xylan, which is prepared from birch-wood xylan by the method of Johnson et al. 1988 (Johnson, K. G., J. D. Fontana, and C. R. Mackenzie. 1988. Measurement of acetylxylan esterase in *Streptomyces*. Methods Enzymol. 160:551-580). The acetate released from acetyl xylan is measured with an acetic acid assay kit (Biopharm) adapted for the physical requirements of the enzyme (Kosugi A, Murashima K, and Dol R H; *Xylanese and Acetyl Xylan Esterase Activities of XynA, a Key Subunit of the Clostridium cellulovorans Cellulosome for Xylan Degradation*; Appl. Environm. I Microbiol.; vol. 68; pp. 6399-6402; 2002).

Example 15

Determining Phytase Activity

The culture fluid or a cell lysate of a host strain synthesising and secreting a phytase in a suitable buffer may be assayed for phytase activity. A suitable volume of such a sample is diluted in 0.1 M sodium acetate and 0.01% Tween-20, pH 5.5 in a suitable buffer, which can be —HCl at pH 3.0 to 3.5, sodium acetate at pH 4.0 to 5.5, morpholinethanesulfonlc acid (MES) at pH 6.0 to 6.5, and Tris-HCl at pH 7.0 to 9.0, are further diluted in 20-fold into the substrate solution (5 mM sodium phytate [Sigma] in 0.1 M sodium acetate, and 0.01% Tween-20 [pH 5.5], and preincubated at 37° C.) to start the reaction. After 30 min at 37° C., the reaction is stopped by adding an equal volume of 10% trichloroacetic acid. Free inorganic phosphate is measured by the addition of an equal volume of molybdate reagent containing, in 100 ml, 7.39 of $FeSO_4$. 1.0 g of $(NH_4)_6Mo_7O_{24}.4H_2O$, and 3.2 ml of $H_2SO_4$. Absorbance was measured at 750 nm (Vmax microtiter plate reader, Molecular Devices) (Lassen S F; Breinholt J; Ostergaard P R; Brugger R; Bischoff A; Wyss M; Fugisang C C, *Expression, gene cloning, and characterization of five novel phytases from four basidiomycete fungi: Peniophora lycii, Agrocybe pediades, a Carlporia sp., and Trametes pubescens*; Appl. Environ. Micr.; 67; pp. 4701-4707; 2001).

Example 16

Determining Phospholipase Activity

The culture fluid or a cell lysate of a host strain synthesising and secreting a phospholipase in a suitable buffer may be assayed for phospholipase activity. Lecithin is added to suitable volume of such a sample. The Lecithin is hydrolyzed under constant pH and temperature, and the phospholipase activity is determined as the rate of titrant (0.1N NaOH) consumption during neutralization of the liberated fatty acid. The substrate is soy lecithin (L-α-Phosphotidyl-Choline), and the conditions are pH 8.00, 40.0° C., reaction time 2 min. The unit (LEU) is defined relative to a standard.

Example 17

Expression of Aspartyl Protease Gene (SEQ ID NO; 2) in *Bacillus subtilis*

The signal peptide from the protease SAVINASE™ (also known as subtillsin 309 from *B. Licheniformis* from Novozymes A/S) was fused by PCR in frame to the gene encoding the aspartyl protease (SEQ ID NO: 2). The DNA coding for the resulting coding sequence was integrated by homologous recombination on the *Bacillus subtilis* host cell genome. The gene construct was expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence. The gene coding for Chloramphenicol acetyl transferase was used as maker. (Described e.g. in Diderichsen et al., *A useful cloning vector for Bacillus subtilis*. Plasmid, 30, p. 312, 1993).

Chloramphenicol resistant transformants were analyzed by DNA sequencing to verify the correct DNA sequence of the construct. One such clone was selected.

Fermentations of the aspartyl protease (SEQ ID NO: 2) expression clone was performed on a rotary shaking table in 600 ml baffled Erlenmeyer flasks each containing 100 ml PS-1 media supplemented with 6 mg/l chloramphenicol. The clone was fermented for 6 days at 37° C. and sample was taken at day 3, 4, 5 and 6 and analyzed for proteolytic activity. The activity was determined (se example 7) as a spot test of 20 microliter culture fluid on 0.1% AZCL-collagen (Megazyme™) LB-PG agar plates at pH 3.4. The plates were incubated at 55° C. (over night) and the activity was visible as blue halos around the spots.

Example 18

Purification and Characterization of the Family A4 Protease from *Alicyclobacillus* sp Purification Culture broth was centrifuged (20000×g, 20 min) and the supernatants were carefully decanted from the precipitates. The combined supernatants were filtered through a Seitz EKS plate in order to remove the rest of the *Bacillus* host cells. The EKS filtrate was adjusted to pH 4.0 with citric acid and heated to 70° C. with good stirring on a water bath. When the solution reached 70° C. (it took approx 15 minutes to get from 25° C. to 70° C.), the solution was immediately placed on ice. This heat treatment resulted in some precipitation, which was removed by another Seitz EKS filter plate filtration. Ammonium sulfate was added to the second EKS filtrate to 1.6M final concentration and the pool was applied to a Butyl Toyopearl S column equilibrated in 20 mM $CH_3COOH/NaOH$, 1.6M $(NH_4)_2SO_4$, pH 4.6. After washing the Butyl column extensively with the equilibration buffer, the enzyme was eluted with a linear $(NH_4)SO_4$ gradient (1.6→0M) in the same buffer. Fractions from the column were analysed for protease activity (using the pH 4.0 Assay buffer and 37° C. assay temperature) and fractions with activity were pooled. The pooled fractions were transferred to 20 mM $CH_3COOH/NaOH$, pH 5.5 on a G25 sephadex column and applied to a SOURCE 30Q column equilibrated in the same buffer. After washing the SOURCE 30Q column extensively with the equilibration buffer, the protease was eluted with a linear NaCl gradient (0→0.5M) in the same buffer. Fractions from the column were analysed for protease activity (pH 4.0, 37° C.) and fractions with activity were pooled. The pool, which was slightly coloured, was treated with 1% (w/v) Activated charcoal for 5 minutes and the charcoal was removed by a 0.45 µ filtration. The purity of the filtrate was analysed by SDS-PAGE, where only one band was seen on the coomassie stained gel.

Assay:

A Protazyme OL (cross-linked and dyed collagen) assay was used. A Protazyme OL tablet (from Megazyme) was suspended in 2.0 ml 0.01% Triton X-100 by gentle stirring. 500 microliter of this suspension and 500 microliter assay buffer were mixed in an Eppendorf tube and placed on ice. 20 microliter protease sample (diluted in 0.01% Triton X-100) was added. The assay was initiated by transferring the Eppendorf tube to an Eppendorf thermomixer, which was set to the assay temperature. The tube was incubated for 15 minutes on the Eppendorf thermomixer at its highest shaking rate (1400 rpm). The incubation was stopped by transferring the tube back to the ice bath. Then the tube was centrifuged in an ice-cold centrifuge for a few minutes, 200 microliter supernatant was transferred to a microtiter plate and $OD_{650}$ was read at 650 nm. A buffer blind was included in the assay (instead of enzyme). $OD_{650}$ (enzyme)-$OD_{650}$ (buffer blind) was a measure of protease activity.

| Protease assay: | |
|---|---|
| Substrate: | Protazyme OL tablets (Megazyme T-PROL). |
| Temperature: | Controlled. |
| Assay buffers: | 100 mM succinic acid, 100 mM HEPES, 100 mM CHES, 100 mM CABS, 1 mM $CaCl_2$, 150 mM KCl, 0.01% Triton X-100 adjusted to pH-values 2.0, 3.0, 4.0, 5.0, 6.0, 7.0, 8.0, 9.0, 10.0, 11.0 and 12.0 with HCl or NaOH. |

Characterisation: pH-Activity, pH-Stability, and Temperature-Activity:

The above protease assay was used for obtaining the pH-activity profile, the pH-stability profile as well as the temperature-activity profile at pH 3.0. For the pH-stability profile the protease was diluted 5× in the Assay buffers and incubated for 2 hours at 37° C. After incubation the protease samples were transferred to pH 3.0, before assay for residual activity, by dilution in the pH 3 Assay buffer.

| pH-activity profile at 37° C. | |
|---|---|
| pH | *Alicyclobacillus* protease from EXP00663 |
| 2 | 0.90 |
| 3 | 0.98 |
| 4 | 1.00 |
| 5 | 0.93 |
| 6 | 0.77 |
| 7 | 0.28 |
| 8 | 0.04 |
| 9 | 0.02 |

| pH-stability profile (residual activity after 2 hours at 37° C.) | |
|---|---|
| pH | *Alicyclobacillus* protease from EXP00663 |
| 2.0 | 0.93 |
| 3.0 | 0.97 |
| 4.0 | 0.94 |
| 5.0 | 0.97 |
| 6.0 | 0.93 |
| 7.0 | 0.94 |
| 8.0 | 0.99 |
| 9.0 | 0.94 |
| 10.0 | 0.81 |
| 11.0 | 0.76 |
| 12.0 | 0.46 |
| 3.0 and after 2 hours at 5° C. | 1.00 |

| Temperature activity profile (at pH 3.0) | |
|---|---|
| Temp (° C.) | *Alicyclobacillus* protease from EXP00663 |
| 15 | 0.08 |
| 25 | 0.19 |
| 37 | 0.60 |
| 50 | 0.94 |
| 60 | 1.00 |
| 70 | 0.89 |
| 80 | 0.45 |

Other Characteristics:

The relative molecular weight of the A4 protease as determined by SDS-PAGE was:

$M_r$=26 kDa.

Example 19

Expression of Acid Cellulase Gene (SEQ ID NO: 1) in *Bacillus subtilis*

The signal peptide from Termamyl™ (Novozymes) was fused by PCR in frame to the gene encoding the acid cellulase (SEQ ID NO: 1). The DNA coding for the resulting coding sequence was integrated by homologous recombination on the *Bacillus subtilis* host coding genome. The gene construct was expressed under the control of a triple promoter system (as described in WO 99/43835), consisting of the promoters from *Bacillus licheniformis* alpha-amylase gene (amyL), *Bacillus amyloliquefaciens* alphaamylase gene (amyQ), and the *Bacillus thuringiensis* cryIIIA promoter including stabilizing sequence. The gene coding for Chloramphenicol acetyl-transferase was used as maker (Described e.g. in Diderichsen et al., *A useful cloning vector for Bacillus subtilis*. Plasmid, 30, p. 312, 1993).

Chloramphenicol resistant transformants were analyzed by DNA sequencing to verify the correct DNA sequence of the construct. One such clone was selected.

Fermentations of the acid cellulase (SEQ ID NO: 1) expression clone was performed on a rotary shaking table in 500 ml baffled Erlenmeyer flasks each containing 100 ml PS-1 media supplemented with 6 mg/l chloramphenicol. The cone was fermented for 3 days at 37° C. and sample was taken at day 1, 2 and 3 and analyzed for cellulase activity. The activity was determined as a spot test of 20 microliter culture fluid on 0.1% AZCL-HE-cellulase (Megazyme™) LB-PG agar plates at pH 3.4. The plates were incubated at 55° C. (over night) and the activity was visible as blue halos around the spots.

The invention claimed is:

1. An isolated polypeptide which has an amino acid sequence at least 90% identical with the sequence of SEQ ID NO: 27, and wherein the polypeptide has glutamic peptidase activity.

2. The polypeptide of claim 1, which has an amino acid sequence at least 95% identity with the sequence of SEQ ID NO: 27.

3. The polypeptide of claim 1, which has an amino acid sequence at least 96% identity with the sequence of SEQ ID NO: 27.

4. The polypeptide of claim 1, which has an amino acid sequence at least 97% identity with the sequence of SEQ ID NO: 27.

5. The polypeptide of claim 1, which has an amino acid sequence at least 98% identity with the sequence of SEQ ID NO: 27.

6. The polypeptide of claim 1, which has an amino acid sequence at least 99% identity with the sequence of SEQ ID NO: 27.

7. The polypeptide of claim 1, which comprises the amino acid sequence of SEQ ID NO: 27.

8. The polypeptide of claim 1, which consists of the amino acid sequence of SEQ ID NO: 27.

9. The polypeptide of claim 1, which comprises the amino acid sequence of the mature peptidase from position 1 to position 240 of SEQ ID NO: 27.

10. The polypeptide of claim 1, which consists of the amino acid sequence of the mature peptidase from position 1 to position 240 of SEQ ID NO: 27.

11. A composition comprising the polypeptide of claim 1 and an excipient.

12. The composition of claim 11, further comprising one or more additional enzymes.

13. The composition of claim 11, which is a detergent composition which further comprises a surfactant.

14. The composition of claim 11, which is a feed composition which further comprises a cereal or grain product.

15. The composition of claim 11, which is a food composition.

* * * * *